(12) United States Patent
Cartledge et al.

(10) Patent No.: US 8,864,823 B2
(45) Date of Patent: Oct. 21, 2014

(54) METHODS AND APPARATUS FOR CONTROLLING THE INTERNAL CIRCUMFERENCE OF AN ANATOMIC ORIFICE OR LUMEN

(75) Inventors: Richard G. Cartledge, Ft. Lauderdale, FL (US); Leonard Y. Lee, New York, NY (US); James I. Fann, Portola Valley, CA (US)

(73) Assignee: StJude Medical, Cardiology Division, Inc., St. Paul, MN (US)

( * ) Notice: Subject to any disclaimer, the term of this patent is extended or adjusted under 35 U.S.C. 154(b) by 954 days.

(21) Appl. No.: 11/449,139

(22) Filed: Jun. 7, 2006

(65) Prior Publication Data
US 2007/0016287 A1    Jan. 18, 2007

Related U.S. Application Data

(63) Continuation-in-part of application No. 11/390,984, filed on Mar. 27, 2006.

(60) Provisional application No. 60/665,296, filed on Mar. 25, 2005, provisional application No. 60/688,202, filed on Jun. 7, 2005.

(51) Int. Cl.
*A61F 2/24*    (2006.01)

(52) U.S. Cl.
CPC ............. *A61F 2/2448* (2013.01); *A61F 2/2466* (2013.01); *A61F 2250/0004* (2013.01)
USPC ....................................................... 623/2.37

(58) Field of Classification Search
CPC .... A61F 2/2442; A61F 2/2445; A61F 2/2466
USPC ................................................ 623/2.36–2.41
See application file for complete search history.

(56) References Cited

U.S. PATENT DOCUMENTS

| | | |
|---|---|---|
| 3,875,928 A | 4/1975 | Angelchik |
| 4,042,979 A | 8/1977 | Angell |
| 4,439,902 A | 4/1984 | Huxtable |
| 4,489,446 A | 12/1984 | Reed |
| 4,602,911 A | 7/1986 | Ahmadi et al. |

(Continued)

FOREIGN PATENT DOCUMENTS

| | | |
|---|---|---|
| EP | 0 495 417 A1 | 7/1992 |
| EP | 1 554 990 | 7/2005 |

(Continued)

OTHER PUBLICATIONS

Int'l Search Report received in corresponding Int'l Application No. PCT/US06/11275.

(Continued)

*Primary Examiner* — Howie Matthews
(74) *Attorney, Agent, or Firm* — Lerner, David, Littenberg, Krumholz & Mentlik, LLP

(57) ABSTRACT

An implantable device is provided for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

17 Claims, 45 Drawing Sheets

(56) References Cited

U.S. PATENT DOCUMENTS

| | | |
|---|---|---|
| 4,676,253 A | 6/1987 | Newman et al. |
| 5,064,431 A | 11/1991 | Gilbertson et al. |
| 5,102,417 A | 4/1992 | Palmaz |
| 5,119,674 A | 6/1992 | Nielson |
| 5,201,880 A | 4/1993 | Wright et al. |
| 5,226,429 A | 7/1993 | Kuzmak |
| 5,243,976 A | 9/1993 | Ferek-Petric et al. |
| 5,306,296 A | 4/1994 | Wright et al. |
| 5,405,378 A | 4/1995 | Strecker |
| 5,411,552 A | 5/1995 | Andersen et al. |
| 5,423,851 A | 6/1995 | Samuels |
| 5,443,477 A | 8/1995 | Marin et al. |
| 5,522,884 A | 6/1996 | Wright et al. |
| 5,593,424 A | 1/1997 | Northrup III |
| 5,601,604 A | 2/1997 | Vincent |
| 5,674,279 A | 10/1997 | Wright et al. |
| 5,709,695 A | 1/1998 | Northrup, III |
| 5,709,701 A | 1/1998 | Parodi |
| 5,713,951 A | 2/1998 | Garrison et al. |
| 5,769,812 A | 6/1998 | Stevens et al. |
| 5,814,056 A | 9/1998 | Prosst et al. |
| 5,814,097 A | 9/1998 | Sterman et al. |
| 5,824,055 A | 10/1998 | Spiridigliozzi et al. |
| 5,908,435 A | 6/1999 | Samuels |
| 5,961,539 A | 10/1999 | Northrup, III et al. |
| 5,972,030 A | 10/1999 | Garrison et al. |
| 5,984,959 A | 11/1999 | Robertson et al. |
| 5,989,284 A | 11/1999 | Laufer |
| 6,067,991 A | 5/2000 | Forsell |
| 6,110,200 A | 8/2000 | Hinnenkamp |
| 6,120,525 A | 9/2000 | Westcott |
| 6,152,144 A | 11/2000 | Lesh et al. |
| 6,152,936 A | 11/2000 | Christy et al. |
| 6,168,616 B1 | 1/2001 | Brown, III |
| 6,168,816 B1 | 1/2001 | Hammond |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,561 B1 | 5/2001 | Frazier et al. |
| 6,235,040 B1 | 5/2001 | Chu et al. |
| 6,245,012 B1 | 6/2001 | Kleshinski |
| 6,269,819 B1 | 8/2001 | Oz et al. |
| 6,355,030 B1 | 3/2002 | Aldrich et al. |
| 6,368,348 B1 | 4/2002 | Gabbay |
| 6,402,781 B1 | 6/2002 | Langberg et al. |
| 6,406,493 B1 | 6/2002 | Tu et al. |
| 6,419,696 B1 * | 7/2002 | Ortiz et al. .................. 623/2.37 |
| 6,451,054 B1 | 9/2002 | Stevens |
| 6,464,707 B1 | 10/2002 | Bjerken |
| 6,470,892 B1 | 10/2002 | Forsell |
| 6,514,265 B2 | 2/2003 | Ho et al. |
| 6,524,338 B1 | 2/2003 | Gundry |
| 6,537,314 B2 | 3/2003 | Langberg et al. |
| 6,547,801 B1 | 4/2003 | Dargent et al. |
| 6,551,332 B1 | 4/2003 | Nguyen et al. |
| 6,564,805 B2 | 5/2003 | Garrison et al. |
| 6,569,198 B1 | 5/2003 | Wilson et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,629,534 B1 | 10/2003 | St. Goar et al. |
| 6,641,593 B1 | 11/2003 | Schaller et al. |
| 6,651,671 B1 | 11/2003 | Donlon et al. |
| 6,656,185 B2 | 12/2003 | Gleason et al. |
| 6,685,713 B1 | 2/2004 | Ahmed |
| 6,689,164 B1 | 2/2004 | Seguin |
| 6,706,065 B2 | 3/2004 | Langbergt et al. |
| 6,709,456 B2 | 3/2004 | Langberg et al. |
| 6,716,243 B1 | 4/2004 | Colvin et al. |
| 6,723,038 B1 | 4/2004 | Schroeder et al. |
| 6,749,630 B2 | 6/2004 | McCarthy et al. |
| 6,767,362 B2 | 7/2004 | Schreck |
| 6,776,789 B2 | 8/2004 | Bryant et al. |
| 6,790,229 B1 | 9/2004 | Berreklouw |
| 6,793,673 B2 | 9/2004 | Kowalsky et al. |
| 6,797,002 B2 | 9/2004 | Spence et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 6,840,246 B2 | 1/2005 | Downing |
| 6,872,223 B2 | 3/2005 | Roberts et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,911,035 B1 | 6/2005 | Blomme |
| 6,921,407 B2 | 7/2005 | Nguyen et al. |
| 6,926,715 B1 | 8/2005 | Hauck et al. |
| 6,932,838 B2 | 8/2005 | Schwartz et al. |
| 6,942,694 B2 | 9/2005 | Liddicoat et al. |
| 6,974,476 B2 | 12/2005 | McGuckin, Jr. et al. |
| 6,986,738 B2 | 1/2006 | Glukhovsky et al. |
| 7,011,682 B2 | 3/2006 | Lashinski et al. |
| 7,097,658 B2 | 8/2006 | Oktay |
| 7,175,660 B2 | 2/2007 | Cartledge et al. |
| 7,220,237 B2 | 5/2007 | Gannoe et al. |
| 7,297,150 B2 | 11/2007 | Cartledge et al. |
| 7,329,280 B2 * | 2/2008 | Bolling et al. ................ 623/2.36 |
| 7,361,190 B2 * | 4/2008 | Shaoulian et al. ........... 623/2.36 |
| 7,377,916 B2 | 5/2008 | Rudko et al. |
| 7,381,219 B2 | 6/2008 | Salahieh et al. |
| 7,416,557 B2 | 8/2008 | Drasler et al. |
| 7,455,690 B2 | 11/2008 | Cartledge et al. |
| 7,527,647 B2 | 5/2009 | Spence |
| 7,780,683 B2 | 8/2010 | Roue et al. |
| 7,815,676 B2 | 10/2010 | Greenberg |
| 7,842,098 B2 | 11/2010 | Rioux et al. |
| 8,226,707 B2 | 7/2012 | White |
| 8,236,049 B2 | 8/2012 | Rowe et al. |
| 8,241,351 B2 | 8/2012 | Cabiri |
| 8,449,605 B2 | 5/2013 | Lichtenstein et al. |
| 8,470,023 B2 | 6/2013 | Eidenschink et al. |
| 2001/0049558 A1 | 12/2001 | Liddicoat et al. |
| 2002/0007222 A1 | 1/2002 | Desai |
| 2002/0107540 A1 | 8/2002 | Whalen et al. |
| 2002/0128708 A1 | 9/2002 | Northrup, III et al. |
| 2002/0151967 A1 | 10/2002 | Mikus et al. |
| 2002/0169358 A1 | 11/2002 | Mortier et al. |
| 2002/0173841 A1 | 11/2002 | Ortiz et al. |
| 2003/0018358 A1 | 1/2003 | Saadat |
| 2003/0040791 A1 | 2/2003 | Oktay |
| 2003/0050693 A1 | 3/2003 | Quijano et al. |
| 2003/0074012 A1 | 4/2003 | Nguyen et al. |
| 2003/0083742 A1 | 5/2003 | Spence et al. |
| 2003/0093148 A1 | 5/2003 | Bolling et al. |
| 2003/0130730 A1 | 7/2003 | Cohn et al. |
| 2003/0130731 A1 * | 7/2003 | Vidlund et al. ............... 623/2.37 |
| 2003/0191479 A1 | 10/2003 | Thornton |
| 2003/0199974 A1 | 10/2003 | Lee et al. |
| 2003/0229359 A1 | 12/2003 | Fortier |
| 2003/0233142 A1 | 12/2003 | Morales et al. |
| 2004/0011365 A1 | 1/2004 | Govari et al. |
| 2004/0019378 A1 | 1/2004 | Hlavka et al. |
| 2004/0030382 A1 | 2/2004 | St. Goar et al. |
| 2004/0068276 A1 | 4/2004 | Golden et al. |
| 2004/0088047 A1 | 5/2004 | Spence et al. |
| 2004/0111099 A1 | 6/2004 | Nguyen et al. |
| 2004/0127980 A1 | 7/2004 | Kowalsky et al. |
| 2004/0133147 A1 | 7/2004 | Woo |
| 2004/0138744 A1 * | 7/2004 | Lashinski et al. ........... 623/2.36 |
| 2004/0148019 A1 | 7/2004 | Vidlund et al. |
| 2004/0148021 A1 | 7/2004 | Cartledge et al. |
| 2004/0153144 A1 | 8/2004 | Seguin |
| 2004/0153146 A1 | 8/2004 | Lashinski et al. |
| 2004/0153147 A1 | 8/2004 | Mathis |
| 2004/0161611 A1 | 8/2004 | Mueller et al. |
| 2004/0162611 A1 | 8/2004 | Marquez |
| 2004/0172046 A1 | 9/2004 | Hlavka et al. |
| 2004/0176840 A1 | 9/2004 | Langberg et al. |
| 2004/0181238 A1 | 9/2004 | Zarbatay et al. |
| 2004/0186566 A1 | 9/2004 | Hindrichs et al. |
| 2004/0193191 A1 | 9/2004 | Starksen et al. |
| 2004/0225353 A1 | 11/2004 | McGuckin et al. |
| 2004/0243153 A1 | 12/2004 | Liddicoat et al. |
| 2004/0243229 A1 | 12/2004 | Vidlund et al. |

(56) References Cited

U.S. PATENT DOCUMENTS

| | | |
|---|---|---|
| 2004/0249453 A1 | 12/2004 | Cartledge et al. |
| 2005/0060030 A1 | 3/2005 | Lashinski et al. |
| 2005/0065550 A1 | 3/2005 | Starksen et al. |
| 2005/0070999 A1 | 3/2005 | Spence |
| 2005/0119734 A1 | 6/2005 | Spence et al. |
| 2005/0119735 A1 | 6/2005 | Spence et al. |
| 2005/0131533 A1 | 6/2005 | Alfieri et al. |
| 2005/0149114 A1 | 7/2005 | Cartledge et al. |
| 2005/0192601 A1 | 9/2005 | Demarais |
| 2005/0216079 A1 | 9/2005 | MaCoviak |
| 2006/0058817 A1 | 3/2006 | Starksen et al. |
| 2006/0074485 A1 | 4/2006 | Realyvasquez |
| 2006/0100697 A1 | 5/2006 | Casanova |
| 2006/0106405 A1 | 5/2006 | Fann et al. |
| 2006/0135964 A1 | 6/2006 | Vesely |
| 2007/0016287 A1 | 1/2007 | Cartledge et al. |
| 2007/0051377 A1 | 3/2007 | Douk et al. |
| 2007/0118215 A1 | 5/2007 | Moaddeb |
| 2007/0233239 A1 | 10/2007 | Navia et al. |
| 2007/0244556 A1 | 10/2007 | Rafiee et al. |
| 2007/0299543 A1 | 12/2007 | Cartledge et al. |
| 2008/0004697 A1 | 1/2008 | Lichtenstein et al. |
| 2008/0027483 A1 | 1/2008 | Cartledge et al. |
| 2008/0097496 A1 | 4/2008 | Chang et al. |
| 2008/0109076 A1 | 5/2008 | Cartledge et al. |
| 2008/0306586 A1 | 12/2008 | Cartledge et al. |
| 2009/0005760 A1 | 1/2009 | Cartledge et al. |
| 2009/0054974 A1 | 2/2009 | McGuckin, Jr. et al. |
| 2009/0125102 A1 | 5/2009 | Cartledge et al. |
| 2009/0210052 A1 | 8/2009 | Forster et al. |
| 2009/0234404 A1 | 9/2009 | Fitzgerald et al. |
| 2009/0248148 A1 | 10/2009 | Shaolian et al. |
| 2010/0161047 A1 | 6/2010 | Cabiri |
| 2010/0168835 A1 | 7/2010 | Dorn |
| 2010/0211166 A1 | 8/2010 | Miller et al. |
| 2010/0217385 A1 | 8/2010 | Thompson et al. |
| 2010/0305609 A1 | 12/2010 | Cartledge et al. |
| 2010/0331949 A1 | 12/2010 | Habib |
| 2011/0009956 A1 | 1/2011 | Cartledge et al. |
| 2011/0022168 A1 | 1/2011 | Cartledge |
| 2011/0066231 A1 | 3/2011 | Cartledge et al. |
| 2011/0093060 A1 | 4/2011 | Cartledge et al. |
| 2011/0093062 A1 | 4/2011 | Cartledge et al. |
| 2011/0118828 A1 | 5/2011 | Thompson |
| 2011/0196480 A1 | 8/2011 | Cartledge |
| 2011/0202130 A1 | 8/2011 | Cartledge et al. |
| 2011/0208283 A1 | 8/2011 | Rust |
| 2011/0208295 A1 | 8/2011 | Cartledge et al. |
| 2011/0257633 A1 | 10/2011 | Cartledge et al. |
| 2011/0257737 A1 | 10/2011 | Fogarty et al. |
| 2011/0264191 A1 | 10/2011 | Rothstein |
| 2012/0022633 A1 | 1/2012 | Olson et al. |
| 2012/0022640 A1 | 1/2012 | Gross et al. |
| 2012/0059458 A1 | 3/2012 | Buchbinder et al. |
| 2012/0123531 A1 | 5/2012 | Tsukashima et al. |
| 2012/0136436 A1 | 5/2012 | Cabiri et al. |
| 2012/0158115 A9 | 6/2012 | Arnault De La Menardiere et al. |
| 2012/0197379 A1 | 8/2012 | Laske et al. |
| 2012/0277842 A1 | 11/2012 | Kunis |
| 2013/0006352 A1 | 1/2013 | Yaron |
| 2013/0144371 A1 | 6/2013 | Kavteladze |
| 2013/0172977 A1 | 7/2013 | Forde et al. |

FOREIGN PATENT DOCUMENTS

| | | | |
|---|---|---|---|
| EP | 1611868 A2 | | 1/2006 |
| JP | 61013818 | | 1/1986 |
| JP | 05-049655 | | 3/1993 |
| JP | 10-503399 A | | 3/1998 |
| JP | 3049359 B2 | | 6/2000 |
| JP | 3180136 B2 | | 4/2001 |
| JP | 3180136 B2 | | 6/2001 |
| JP | 2002509448 A | | 3/2002 |
| JP | 2002523172 A | | 7/2002 |
| JP | 2002526194 A | | 8/2002 |
| JP | 2003533275 A | | 11/2003 |
| JP | 2004535851 A | | 12/2004 |
| JP | 2005537067 A | | 12/2005 |
| JP | 2006507104 A | | 3/2006 |
| JP | 2006520651 A | | 9/2006 |
| JP | 2006520670 A | | 9/2006 |
| JP | 2007-502689 | | 2/2007 |
| JP | 2008534086 A | | 8/2008 |
| WO | 9101697 A1 | | 2/1991 |
| WO | 9315690 A2 | | 8/1993 |
| WO | 9603938 A1 | | 2/1996 |
| WO | 97/16135 | | 5/1997 |
| WO | 9719655 A1 | | 6/1997 |
| WO | 99/04730 | | 2/1999 |
| WO | 99/30647 | | 6/1999 |
| WO | 99/30647 A1 | | 6/1999 |
| WO | 9960952 A1 | | 12/1999 |
| WO | 00/03759 | | 1/2000 |
| WO | 0015158 A1 | | 3/2000 |
| WO | 0016700 A1 | | 3/2000 |
| WO | 01/26586 | | 4/2001 |
| WO | 01/50985 | | 7/2001 |
| WO | 2004/012583 | | 2/2004 |
| WO | 2004/019816 A2 | | 3/2004 |
| WO | 2004019826 A1 | | 3/2004 |
| WO | 2004047677 A2 | | 6/2004 |
| WO | 2004/060217 | | 7/2004 |
| WO | 2004080336 A2 | | 9/2004 |
| WO | 2004084746 A2 | | 10/2004 |
| WO | 2004100803 | | 11/2004 |
| WO | 2004/112585 | | 12/2004 |
| WO | 2004/112651 | | 12/2004 |
| WO | 2004/112658 | | 12/2004 |
| WO | 2005/007036 | | 1/2005 |
| WO | 2005/007037 | | 1/2005 |
| WO | 2005/007219 | | 1/2005 |
| WO | 2005/009285 | | 2/2005 |
| WO | 2005/025644 | | 3/2005 |
| WO | 2005018507 A2 | | 3/2005 |
| WO | 2005/046488 | | 5/2005 |
| WO | 2005/055883 | | 6/2005 |
| WO | 2005/062931 | | 7/2005 |
| WO | 2005084592 A2 | | 9/2005 |
| WO | 2006/105084 A2 | | 10/2006 |
| WO | 2005/007037 | | 1/2007 |
| WO | 2007/136783 A2 | | 11/2007 |
| WO | 2008/085814 A2 | | 7/2008 |
| WO | 2009/052509 A1 | | 4/2009 |
| WO | 2010/085649 A1 | | 7/2010 |
| WO | 2010/085659 A1 | | 7/2010 |

OTHER PUBLICATIONS

Extended European Search Report for Application No. 10733913 dated Dec. 11, 2012.
Letter dated Jan. 27, 2011 from Richard H. Levinstein, Esq.
Extended European Search Report for Application No. EP13166640 dated Jul. 1, 2013.
Canadian Office Action for Application No. 2,674,485 dated Dec. 12, 2013.
International Search Report for Application No. PCT/US07/11961 dated Aug. 25, 2008.
Japanese Office Action for Application No. 2011-548135 dated Dec. 6, 2013.
International Search Report for Application No. PCT/US2008/000014 dated Jul. 2, 2008.
International Search Report, PCT/US2010/021810, dated Mar. 24, 2010.
International Search Report, PCT/US2010/021822, dated Mar. 17, 2010.
Supplementary European Search Report for Application No. EP 08712925 dated Feb. 26, 2014.
Supplementary European Search Report, EP 08754396, dated Jan. 26, 2011.
Supplementary European Search Reported dated May 20, 2010.

* cited by examiner

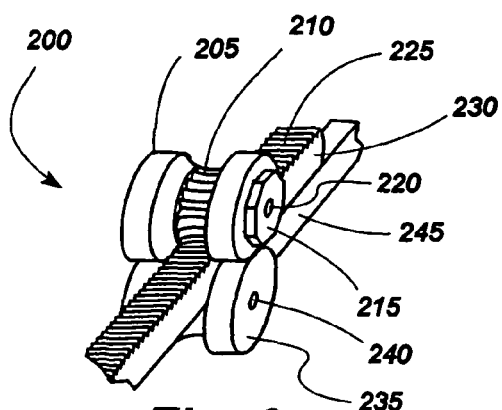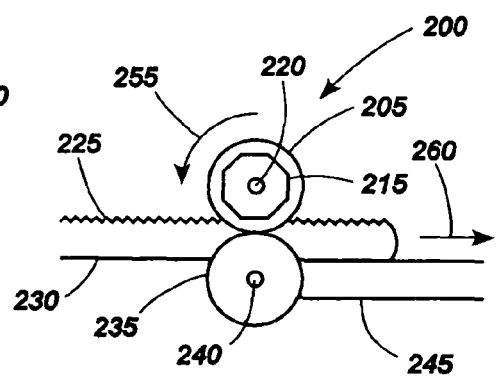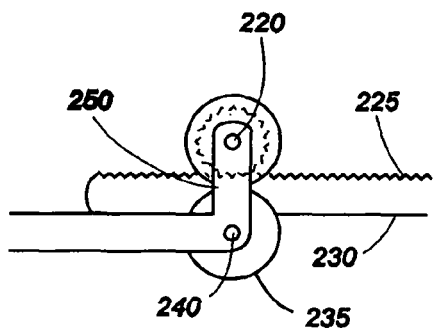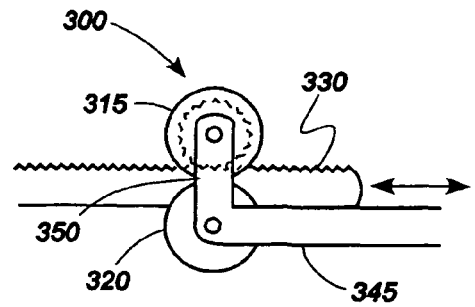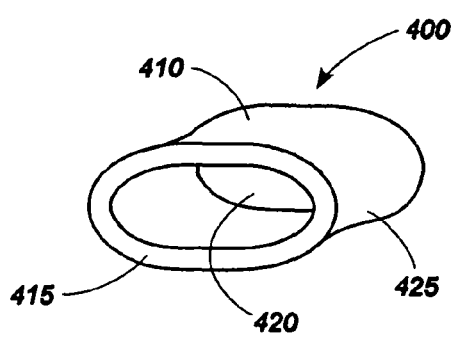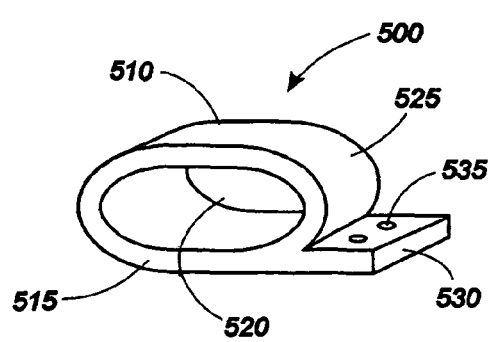

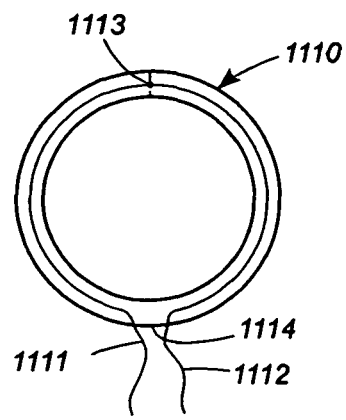
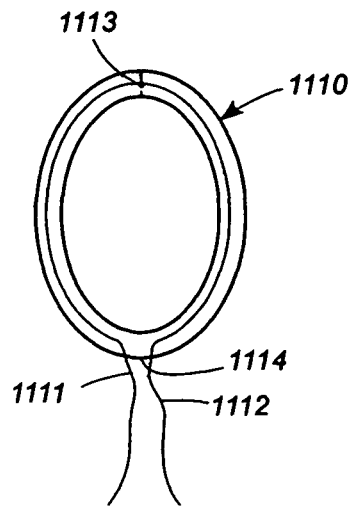
Fig. 40  Fig. 41
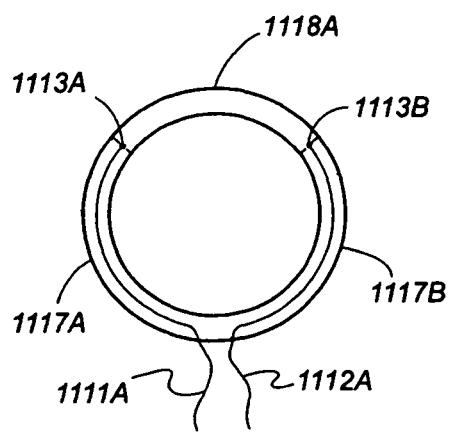
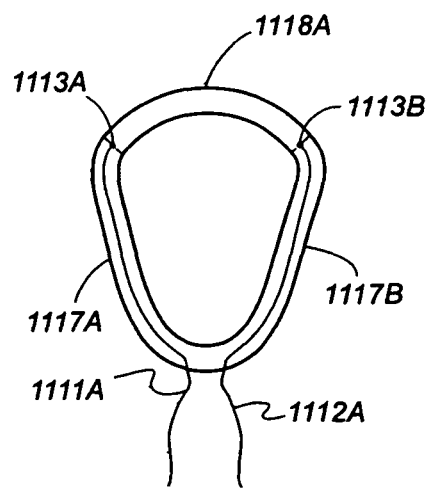
Fig. 42  Fig. 43

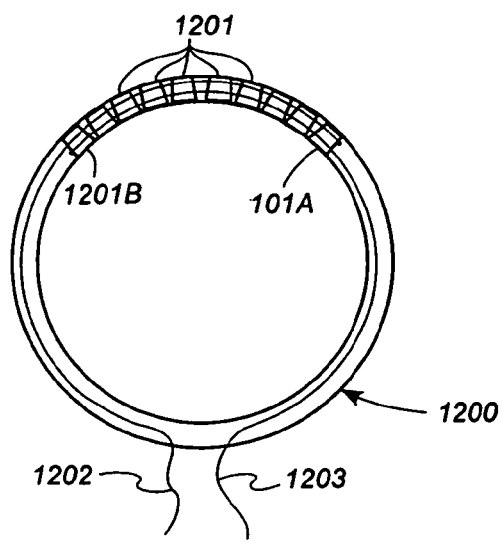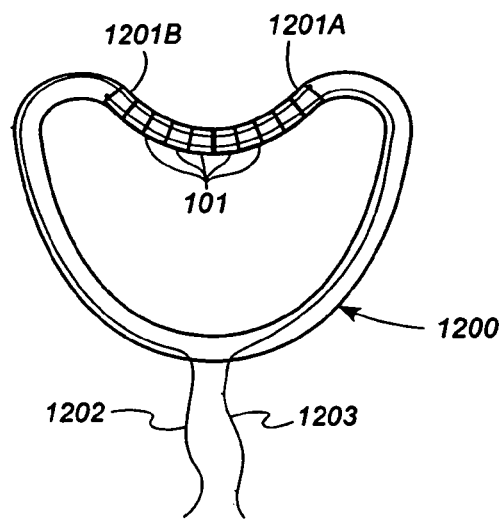
Fig. 48  Fig. 49
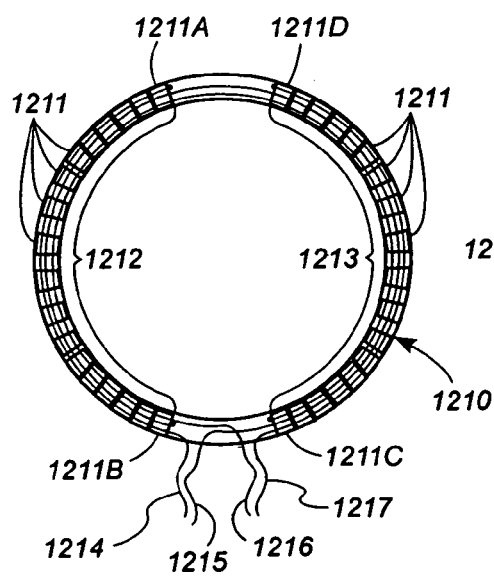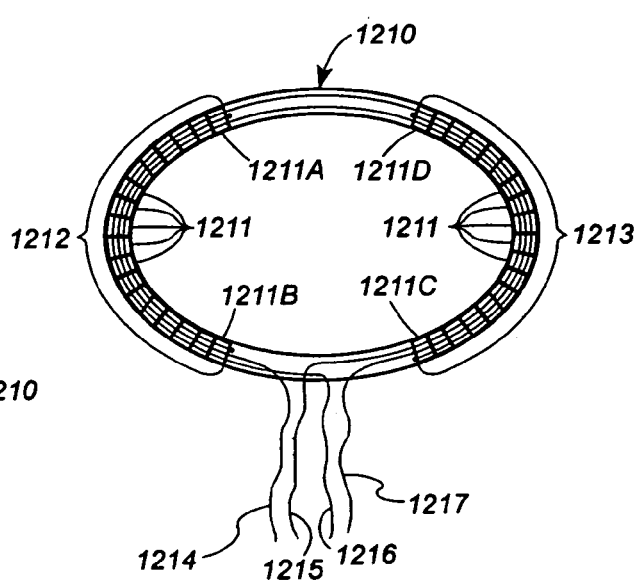
Fig. 50  Fig. 51

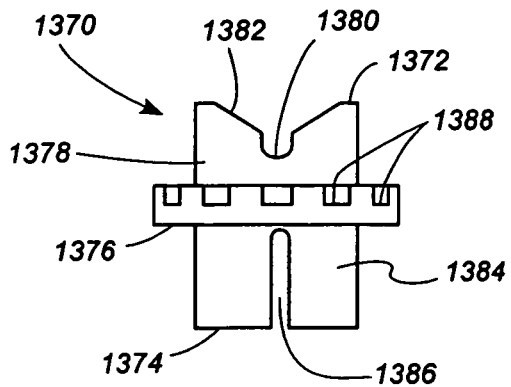
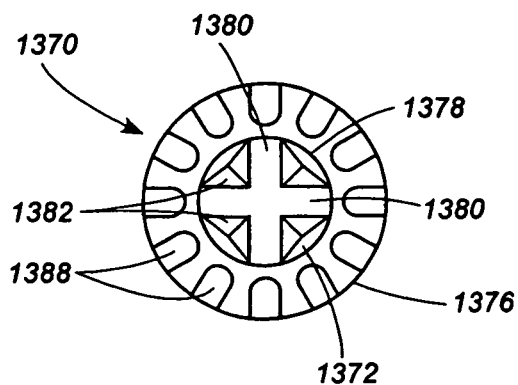
Fig. 63    Fig. 64
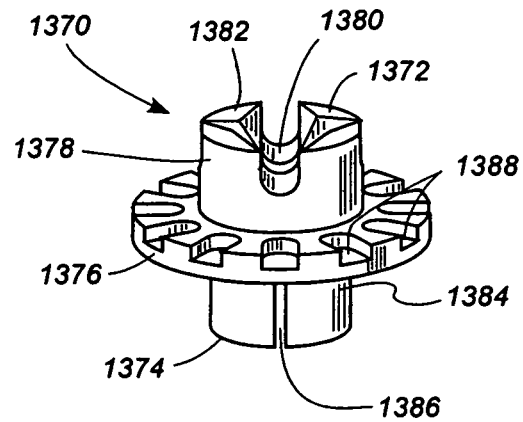
Fig. 65
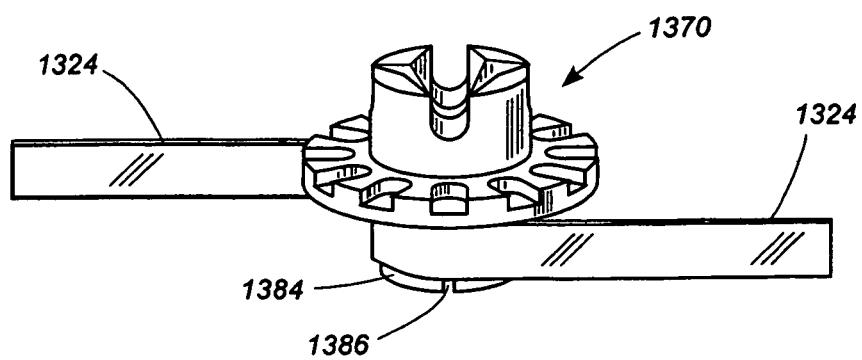
Fig. 66

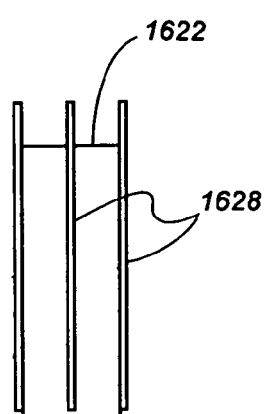
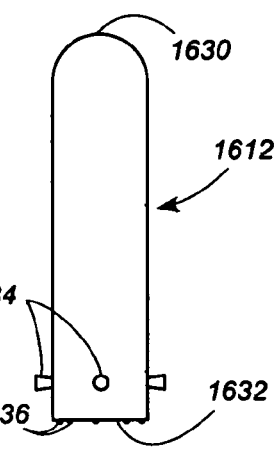
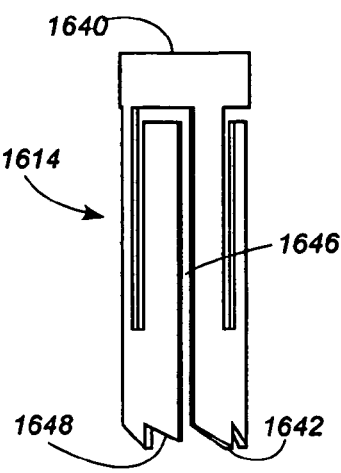
Fig. 74
Fig. 76
Fig. 78
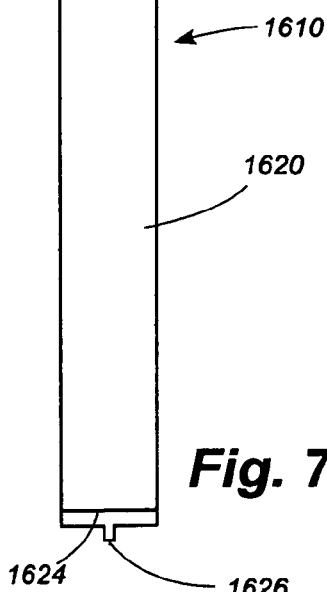
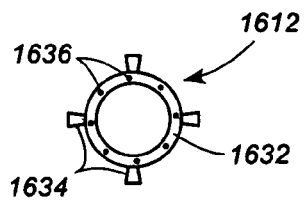
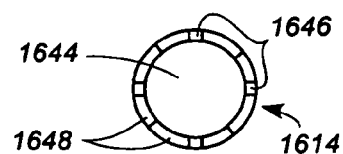
Fig. 77
Fig. 79
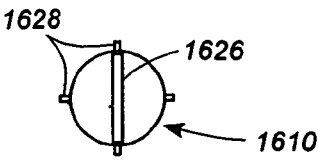
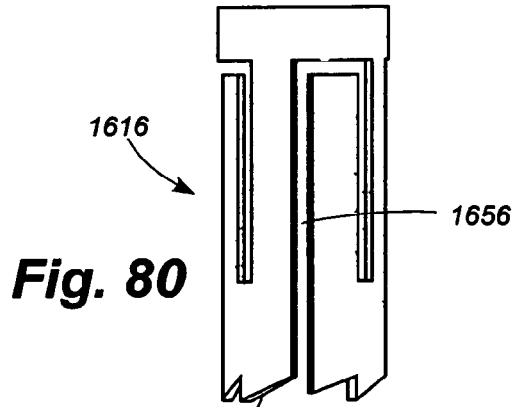
Fig. 75
Fig. 80
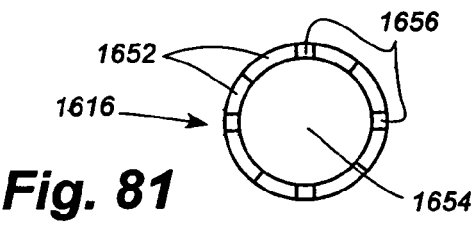
Fig. 81

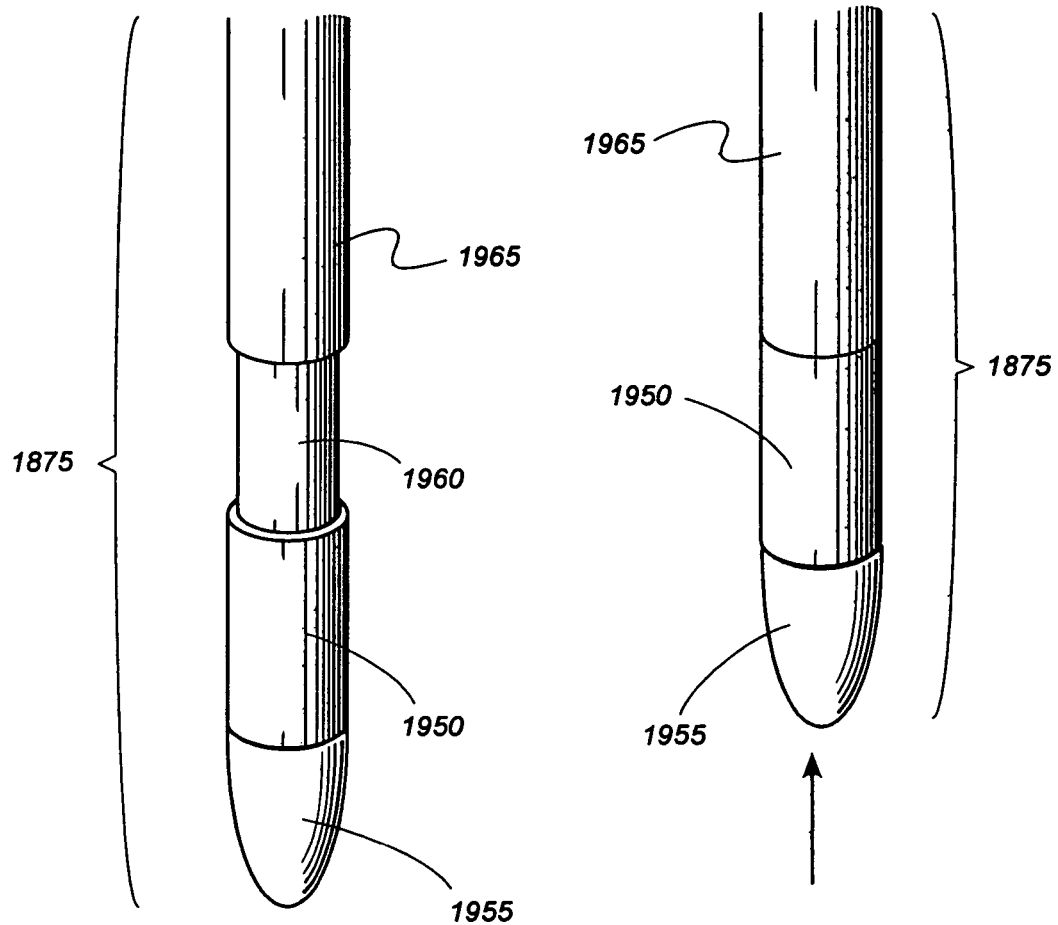
*Fig. 97*    *Fig. 98*

METHODS AND APPARATUS FOR CONTROLLING THE INTERNAL CIRCUMFERENCE OF AN ANATOMIC ORIFICE OR LUMEN

CROSS-REFERENCE TO RELATED APPLICATION

This application is a continuation-in-part of U.S. patent application Ser. No. 11/390,984, filed Mar. 27, 2006, which application claims priority under 35 U.S.C. §119(e) from U.S. Provisional Patent Application No. 60/665,296, filed Mar. 25, 2005, which applications are fully incorporated herein by reference. This application also claim priority under 35 U.S.C. §119(e) from U.S. Provisional Patent Application No. 60/688,202, filed Jun. 7, 2005, which is also incorporated herein by reference.

BACKGROUND

1. Field of the Invention

The present invention relates generally to implantable devices and associated delivery systems, and more particularly to an implantable device and an associated delivery system that controls shape and/or size of an anatomical structure or lumen.

2. Description of the Related Art

Many anatomic structures in the mammalian body are hollow passages in which walls of tissue define a central lumen, which serves as a conduit for blood, other physiologic fluids, nutrient matter, or waste matter passing within the structure. In many physiologic settings, dysfunction may result from a structural lumen, which is either too large or too small. In most such cases, dysfunction can be relieved by interventional changes in the luminal size.

Thus in surgery, there is often a need to reduce the internal circumference of an orifice or other open anatomic structure to narrow the size of the orifice or opening to achieve a desired physiologic effect. Often, such surgical procedures require interruption in the normal physiologic flow of blood, other physiologic fluids, or other structural contents through the orifice or structure. The exact amount of the narrowing required for the desired effect often cannot be fully appreciated until physiologic flow through the orifice or structure is resumed. It would be advantageous, therefore, to have an adjustable means of achieving this narrowing effect, such that the degree of narrowing could be changed after its implantation, but after the resumption of normal flow in situ.

One example of a dysfunction within an anatomic lumen is in the area of cardiac surgery, and specifically valvular repair. Approximately one million open-heart surgical procedures are now performed annually in the United States, and twenty percent of these operations are related to cardiac valves.

The field of cardiac surgery was previously transformed by the introduction of the pump oxygenator, which allowed open-heart surgery to be performed. Valvular heart surgery was made possible by the further introduction of the mechanical ball-valve prosthesis, and many modifications and different forms of prosthetic heart valves have since been developed. However, the ideal prosthetic valve has yet to be designed, which attests to the elegant form and function of the native heart valve. As a result of the difficulties in engineering a perfect prosthetic heart valve, there has been growing interest in repairing a patient's native valve. These efforts have documented equal long-term durability to the use of mechanical prostheses, with added benefits of better ventricular performance due to preservation of the subvalvular mechanisms and obviation of the need for chronic anticoagulation. Mitral valve repair has become one of the most rapidly growing areas in adult cardiac surgery today.

Mitral valve disease can be subdivided into intrinsic valve disturbances and pathology extrinsic to the mitral valve ultimately affecting valvular function. Although these subdivisions exist, many of the repair techniques and overall operative approaches are similar in the various pathologies that exist.

Historically, most valvular pathology was secondary to rheumatic heart disease, a result of a streptococcal infection, most commonly affecting the mitral valve, followed by the aortic valve, and least often the pulmonic valve. The results of the infectious process are mitral stenosis and aortic stenosis, followed by mitral insufficiency and aortic insufficiency. With the advent of better antibiotic therapies, the incidence of rheumatic heart disease is on the decline, and accounts for a smaller percentage of valvular heart conditions in the developed world of the present day. Commissurotomy of rheumatic mitral stenosis was an early example of commonly practiced mitral valve repair outside of the realm of congenital heart defects. However, the repairs of rheumatic insufficient valves have not met with good results due to the underlying valve pathology and the progression of disease.

Most mitral valve disease other than rheumatic results in valvular insufficiency that is generally amenable to repair. Chordae rupture is a common cause of mitral insufficiency, resulting in a focal area of regurgitation. Classically, one of the first successful and accepted surgical repairs was for ruptured chordae of the posterior mitral leaflet. The technical feasibility of this repair, its reproducible good results, and its long-term durability led the pioneer surgeons in the field of mitral valve repair to attempt repairs of other valve pathologies.

Mitral valve prolapse is a fairly common condition that leads over time to valvular insufficiency. In this disease, the plane of coaptation of the anterior and posterior leaflets is "atrialized" relative to a normal valve. This problem may readily be repaired by restoring the plane of coaptation into the ventricle.

The papillary muscles within the left ventricle support the mitral valve and aid in its function. Papillary muscle dysfunction, whether due to infarction or ischemia from coronary artery disease, often leads to mitral insufficiency (commonly referred to as ischemic mitral insufficiency). Within the scope of mitral valve disease, this is the most rapidly growing area for valve repair. Historically, only patients with severe mitral insufficiency were repaired or replaced, but there is increasing support in the surgical literature to support valve repair in patients with moderate insufficiency that is attributable to ischemic mitral insufficiency. Early aggressive valve repair in this patient population has been shown to increase survival and improve long-term ventricular function.

In addition, in patients with dilated cardiomyopathy the etiology of mitral insufficiency is the lack of coaptation of the valve leaflets from a dilated ventricle. The resultant regurgitation is due to the lack of coaptation of the leaflets. There is a growing trend to repair these valves, thereby repairing the insufficiency and restoring ventricular geometry, thus improving overall ventricular function.

The two essential features of mitral valve repair are to fix primary valvular pathology (if present) and to support the annulus or reduce the annular dimension using a prosthesis that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using transesophageal echocardiography (TEE). If significant residual valvular insufficiency is then documented, the surgeon must re-arrest the heart, re-open the heart, and then re-repair or replace the valve. This increases overall operative, anesthesia, and bypass times, and therefore increases the overall operative risks.

If the prosthesis used to reduce the annulus is larger than the ideal size, mitral insufficiency may persist. If the prosthesis is too small, mitral stenosis may result. The need exists, therefore, for an adjustable prosthesis that would allow a surgeon to adjust the annular dimension in situ in a beating heart under TEE guidance or other diagnostic modalities to achieve optimal valvular sufficiency and function.

Cardiac surgery is but one example of a setting in which adjustment of the annular dimension of an anatomic orifice in situ would be desirable. Another example is in the field of gastrointestinal surgery, where the Nissen fundoplication procedure has long been used to narrow the gastro-esophageal junction for relief of gastric reflux into the esophagus. In this setting, a surgeon is conventionally faced with the tension between creating sufficient narrowing to achieve reflux control, but avoiding excessive narrowing that may interfere with the passage of nutrient contents from the esophagus into the stomach. Again, it would be desirable to have a method and apparatus by which the extent to which the gastro-esophageal junction is narrowed could be adjusted in situ to achieve optimal balance between these two competing interests.

Aside from the problem of adjusting the internal circumference of body passages in situ, there is often a need in medicine and surgery to place a prosthetic implant at a desired recipient anatomic site. For example, existing methods proposed for percutaneous mitral repair include approaches through either the coronary sinus or percutaneous attempts to affix the anterior mitral leaflet to the posterior mitral leaflet. Significant clinical and logistical problems attend both of these existing technologies. In the case of the coronary sinus procedures, percutaneous access to the coronary sinus is technically difficult and time consuming to achieve, with procedures which may require several hours to properly access the coronary sinus. Moreover, these procedures employ incomplete annular rings, which compromise their physiologic effect. Such procedures are typically not effective for improving mitral regurgitation by more than one clinical grade. Finally, coronary sinus procedures carry the potentially disastrous risks of either fatal tears or catastrophic thrombosis of the coronary sinus.

Similarly, percutaneous procedures which employ sutures, clips, or other devices to affix the anterior mitral leaflets to the posterior mitral leaflets also have limited reparative capabilities. Such procedures are also typically ineffective in providing a complete repair of mitral regurgitation. Furthermore, surgical experience indicates that such methods are not durable, with likely separation of the affixed valve leaflets. These procedures also fail to address the pathophysiology of the dilated mitral annulus in ischemic heart disease. As a result of the residual anatomic pathology, no ventricular remodeling or improved ventricular function is likely with these procedures.

The need exists, therefore, for a delivery system and methods for its use that would avoid the need for open surgery in such exemplary circumstances, and allow delivery, placement, and adjustment of a prosthetic implant to reduce the diameter of such a mitral annulus in a percutaneous or other minimally invasive procedure, while still achieving clinical and physiologic results that are at least the equivalent of the yields of the best open surgical procedures for these same problems.

The preceding cardiac applications are only examples of some applications according to the present invention. Another exemplary application anticipated by the present invention is in the field of gastrointestinal surgery, where the aforementioned Nissen fundoplication procedure has long been used to narrow the gastro-esophageal junction for relief of gastric reflux into the esophagus. In this setting, a surgeon is conventionally faced with the tension between creating sufficient narrowing to achieve reflux control, but avoiding excessive narrowing that may interfere with the passage of nutrient contents from the esophagus into the stomach. Additionally, "gas bloat" may cause the inability to belch, a common complication of over-narrowing of the GE junction. An adjustable prosthetic implant according to the present invention could allow in situ adjustment in such a setting under physiologic assessment after primary surgical closure. Such an adjustable prosthetic implant according to the present invention could be placed endoscopically, percutaneously, or with an endoscope placed within a body cavity or organ, or by trans-abdominal or trans-thoracic approaches. In addition, such an adjustable prosthetic implant according to the present invention could be coupled with an adjustment means capable of being placed in the subcutaneous or other anatomic tissues within the body, such that remote adjustments could be made to the implant during physiologic function of the implant. This adjustment means can also be contained within the implant and adjusted remotely, i.e. remote control adjustment. Such an adjustment means might be capable of removal from the body, or might be retained within the body indefinitely for later adjustment.

There is a need for an implantable device for controlling at least one of shape and size of an internal structure or lumen. There is a further need for an implantable device that an adjustable member configured to adjust the dimensions of the implantable device. There is still a further need for an implantable device configured to be coupled to an adjustment tool device that provides for adjustment before, during and after the organ resumes near normal-to-normal physiologic function. A further need exists for an implantable device configured to coupled to an adjustment tool that can be attached and re-attached to the implantable device.

SUMMARY

Accordingly, an object of the present invention is to provide an implantable device for controlling shape and/or size of an anatomical structure or lumen.

Another object of the present invention is to provide an implantable device for controlling shape and/or size of an anatomical structure or lumen that is insertable from a minimally invasive surgical entry.

Yet another object of the present invention is to provide a coaxial catheter delivery system for an implantable device that is insertable from a minimally invasive surgical entry.

A further object of the present invention is to provide an implantable device delivery system for percutaneous delivery of the implantable device to an anatomical structure or lumen.

These and other objects of the present invention are achieved in an implantable device for controlling at least one of shape and size of an anatomical structure or lumen. The implantable device has an adjustable member configured to adjust the dimensions of the implantable device. The implantable device is housed in a coaxial catheter and insertable from a minimally invasive surgical entry. An adjustment tool actuates the adjustable member and provide for adjustment before, during or after the anatomical structure or lumen resumes near normal-to-normal physiologic function.

In another embodiment of the present invention, an implantable device delivery system has a housing sheath and a coaxial catheter assembly that includes an actuating catheter slidably disposed within the housing sheath and a core catheter slidably located within the actuating catheter. An implantable device is provided that has an adjustable member configured to adjust the dimensions of the implantable device. The implantable device is housed in the coaxial catheter assembly and insertable from a minimally invasive surgical entry.

In another embodiment of the present invention, an implantable device delivery system includes an implantable device with an adjustable member configured to adjust the dimensions of the implantable device. A delivery system is configured to provide for percutaneous delivery of the implantable device to an anatomical structure or lumen.

In another embodiment of the present invention, a method is provided for controlling shape and/or size of an anatomical structure or lumen of a patient. An implantable device is implanted to the anatomical structure or lumen of the patient. The implantable device has an adjustable member configured to adjust the dimensions of the implantable device. The patient's heart rate and blood pressure are brought back to normal while the patient is still in the operating room. An adjustment tool is used to provide adjustment of the implantable device after the patient's heart rate and blood pressure are brought substantially to normal levels.

BRIEF DESCRIPTION OF THE DRAWINGS

FIG. 6 is a perspective view of a first embodiment of an adjustment means for adjusting the circumference of an implant for reducing the circumference of an anatomic orifice.

FIG. 7 is a right side view of the adjustment means of FIG. 6.

FIG. 8 is a left side view of the adjustment means of FIG. 6.

FIG. 9 is a right side view of a second embodiment of an adjustment means for adjusting the circumference of an implant for reducing the circumference of an anatomic orifice.

FIG. 10 is a perspective view of a first alternate embodiment of an attachment means for the implant of FIG. 1.

FIG. 11 is a perspective view of a second alternate embodiment of an attachment means for the implant of FIG. 1.

FIG. 17 shows the implant in the folded position, and FIG. 18 shows the implant in the unfolded position.

FIG. 40 is a schematic view of the drawstring implant of FIG. 31 showing the drawstring and internal attachment locations.

FIG. 41 is a schematic view of the drawstring implant of FIG. 40 in a cinched state.

FIG. 42 is a schematic view of a variation on the drawstring implant of FIG. 31 showing the drawstring and internal attachment locations.

FIG. 43 is a schematic view of the drawstring implant of FIG. 42 in a cinched state.

FIG. 48 is a schematic view of a first embodiment of a drawstring implant comprising internal shaping members depicting the implant in its normal state.

FIG. 49 is a schematic view of the drawstring implant of FIG. 48 depicting the implant in its cinched state.

FIG. 50 is a schematic view of a second embodiment of a drawstring implant comprising internal shaping members depicting the implant in its normal state.

FIG. 51 is a schematic view of the drawstring implant of FIG. 50 depicting the implant in its cinched state.

FIG. 63 is a side view of a spindle of a winch of the implant of FIG. 56.

FIG. 64 is a top view of the spindle of FIG. 63.

FIG. 65 is an isometric view of the spindle of FIG. 63.

FIG. 66 is an isometric view of the spindle of FIG. 63 showing a section of a band of the implant wrapped around the spindle.

FIG. 74 is a side view of the drive shaft of the drive unit of FIG. 73.

FIG. 75 is a bottom view of the drive shaft of FIG. 74.

FIG. 76 is a side view of the actuator button of the drive unit of FIG. 73.

FIG. 77 is a bottom view of the actuator button of FIG. 76.

FIG. 78 is a side view of the inner cam sleeve of the drive unit of FIG. 73.

FIG. 79 is a bottom view of the inner cam sleeve of FIG. 78.

FIG. 80 is a side view of the outer cam sleeve of the drive unit of FIG. 73.

FIG. 81 is a bottom view of the outer cam sleeve of FIG. 80.

FIG. 97 is a perspective view of the lower end of a touchdown sensor of the implant of FIG. 90, showing the sensor in an uncompressed condition.

FIG. 98 is a perspective view of the lower end of the touchdown sensor of FIG. 97, showing the sensor in a compressed condition.

DETAILED DESCRIPTION

Figure 1:
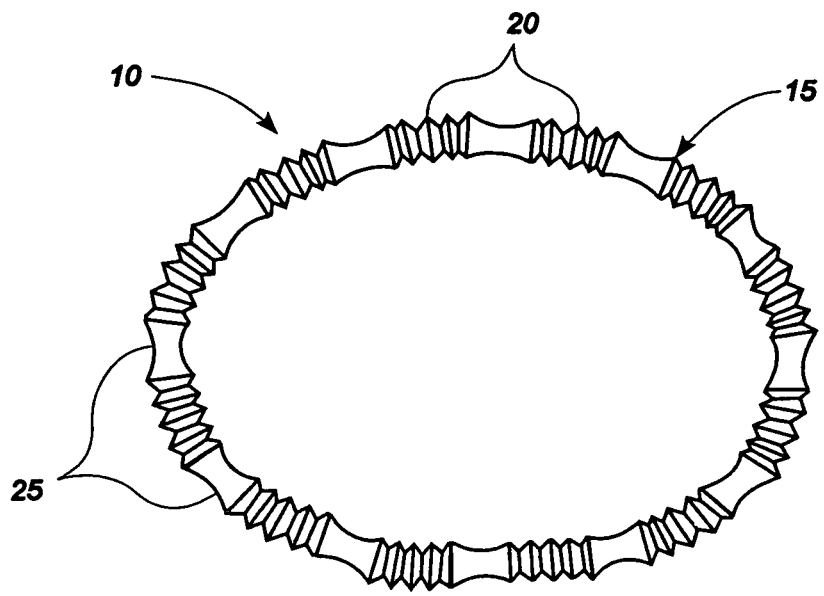
FIG. 1 is a front view of a first embodiment of an implant for reducing the circumference of an anatomic orifice.

Referring now to the drawings, in which like numerals indicate like elements throughout the several views, an exemplary implant 10 comprising an implant body 15 is shown in FIG. 1. The implant body 10 may be provided in a shape and size determined by the anatomic needs of an intended native recipient anatomic site within—a mammalian patient. Such a native recipient anatomic site may be, by way of illustration and not by way of limitation, a heart valve, the esophagus near the gastro-esophageal junction, the anus, or other anatomic sites within a mammalian body that are creating dysfunction that might be relieved by an implant capable of changing the size and shape of that site and maintaining a desired size and shape after surgery. In various embodiments, the implant can be used for positioning an aortic valve, a triple A device positioning, aortic stent grafting applications, aortic endograph applications, aortic triple A stent graphs, ascending aortic aneurysm repair, for stomach applications to control obesity and the like.

Figure 2:
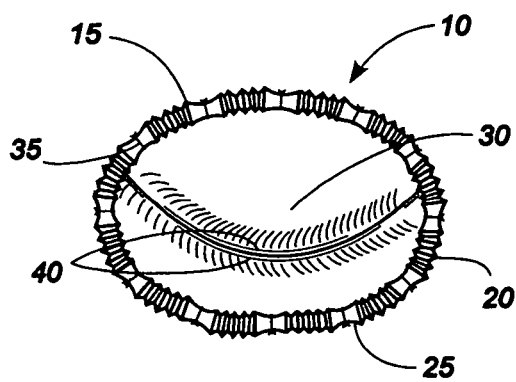
FIG. 2 is a front view of the implant of FIG. I secured to the annulus of a mitral valve, with the implant in an expanded position.
Figure 3:
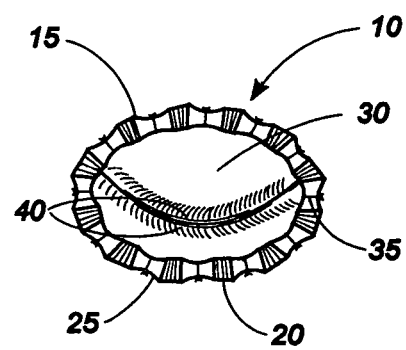
FIG. 3 is a front view of the implant of FIG. I secured to the annulus of a mitral valve, with the implant in a contracted position to reduced the size of the heart valve opening.

The implant 10 of FIG. I comprises a circular implant body 15 which is provided with adjustable corrugated sections 20 alternating with intervening grommet-like attachment means 25 having narrowed intermediate neck portions. As can be seen in FIGS. 2 and 3, the implant body 15 may be secured to the annulus of a heart valve 30 by a fixation means such as a suture 35 secured over or through the attachment means 25. The corrugated sections 20 fold and unfold as the circumference of the implant body 15 shortens or lengthens. Adjustment of the implant 10 in situ may decrease the overall size of the heart valve 30, increasing the coaptation of the valve leaflets 40, and changing the configuration from that shown in FIG. 2 to that shown in FIG. 3.

Figure 4:
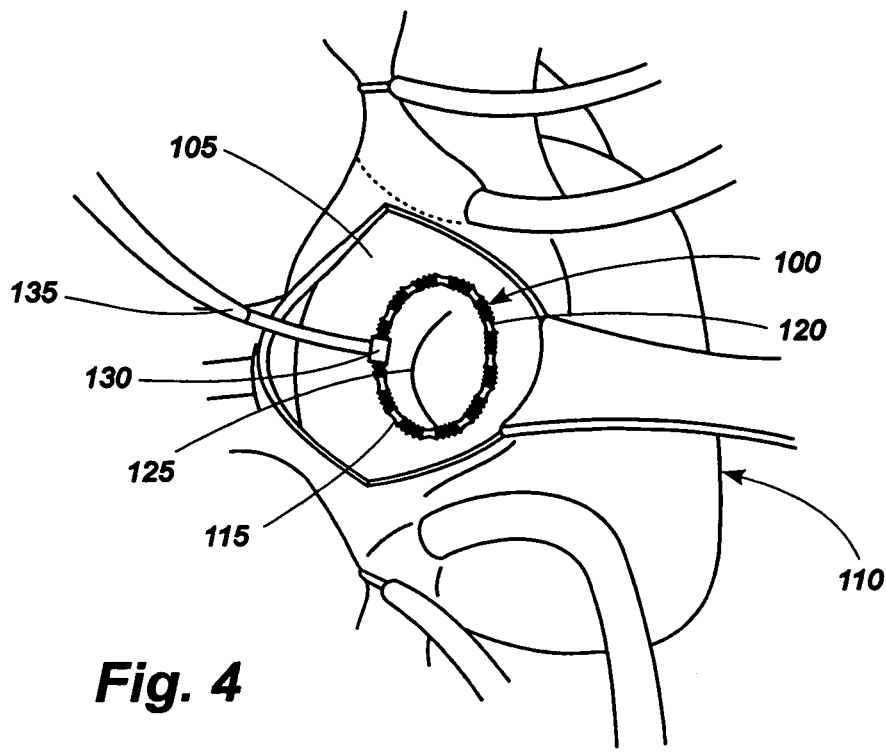
FIG. 4 is a perspective view of a second embodiment of an implant for reducing the circumference of an anatomic orifice, inserted through an open operative cardiac incision and secured around the mitral valve.
Figure 5:
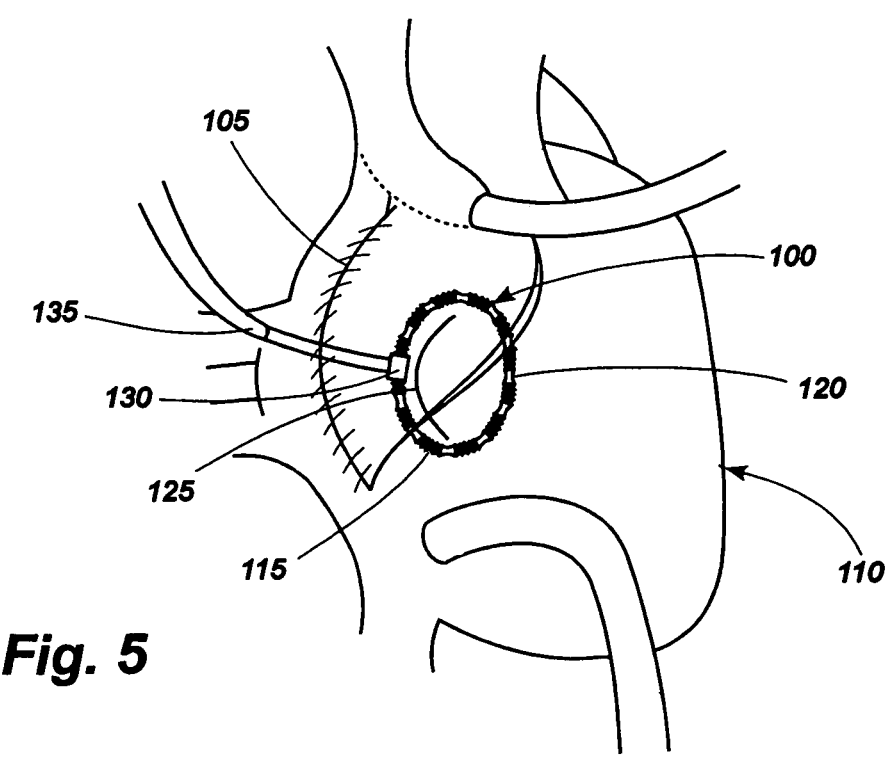
FIG. 5 is a perspective view of the implant of FIG. 4, showing the cardiac incision closed, an adjustment tool extending through the closed incision, and adjustment of the implant possible after the patient has been taken "off pump."
Figure 12:
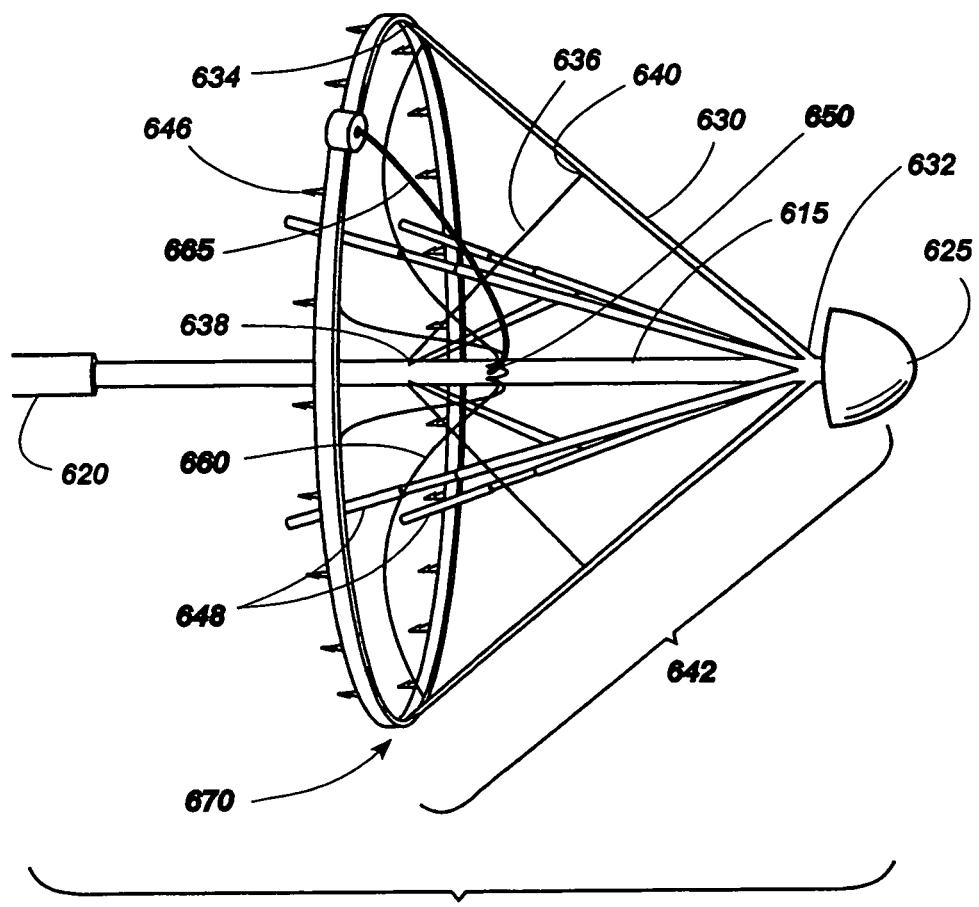
FIG. 12 is a perspective view of a third embodiment of an implant for reducing the circumference of an anatomic orifice.

An additional exemplary embodiment 100 of the present invention is shown in FIGS. 4 and 5, with an open operative cardiac incision 105 in a heart 110 shown in FIG. 4, and closure of the cardiac incision 105 in FIG. 5. As shown in FIG. 49 the exemplary adjustable implant 100 according to the present invention comprises an implant body 115 with attachment means 120 that allows fixation to the annulus of a mitral valve 125. The exemplary adjustable implant 100 is further provided with an adjustment means 130 that is controlled boy an attached or coupled adjustment tool 135. After closure of the myocardial incision 105 in FIG. 5, the adjustment tool 135 remains attached or coupled to the adjustment means 130, so that the size and shape of the implant 100 may further be affected after physiologic flow through the heart 110 is resumed, but with the chest incision still open. Once the desired shape and function are achieved, the adjustment tool 135 may be disengaged from the adjustment means 130 and withdrawn from the myocardial incision 105. In various embodiments according to the present invention, the adjustment means 130 may be configured and placed to allow retention by or re-introduction of the adjustment tool 135 for adjustment following closure of the chest incision.

To use the implant 100 of FIGS. 4 and 5, the physician makes the open operative incision 105 in the heart 110, as shown in FIG. 4, in the conventional manner. The implant 100, mounted at the forward end of adjustment tool 135, is then advanced through the incision 105 and sutured to the annulus of the mitral valve 125. The adjustment tool 135 is then manipulated, e.g., rotated, depending upon the design of the adjustment means 130, to cause the adjustment means to reduce the size of the implant body 115, and hence the underlying mitral valve 125 to which it is sutured, to an approximate size. The myocardial incision 105 can now be closed, as shown in FIG. 5, leaving the adjustment tool extending through the incision for post-operative adjustment.

Once the patient has been taken "off pump" and normal flow of blood through the heart 110 has resumed, but before the chest incision has been closed, further adjustments to the size of the mitral valve 125 can be made by manipulating the adjustment tool 135.

FIGS. 6-8 show an exemplary adjustment means 200 for adjusting the circumference of an annular implant such as the implant 100 previously described. The adjustment means 200 comprises a rack and pinion system in which a first cam 205 with geared teeth 210 and an engagement coupler 215 turns on a first axel 220. In this example, the first cam 205 engages a geared rack 225 on one or more surfaces of a first band 230. The first band 230 passes between the first cam 205 and a second cam 235 that turns on a second axel 240 that is joined to a second band 245. As shown in FIG. 8, the first and second axels 220, 240 are maintained in suitable spaced-apart relation by means of a bracket 250 formed at the end of the second band 245.

The adjustment means 200 is preferably set within a hollow annular implant 100 of the type previously described, though it is possible to use the adjustment means in a stand-alone configuration wherein the first and second bands 230, 245 are opposing ends of the same continuous annular structure. In either event to adjust the length of an implant comprising the adjustment means 200, a tool such as a hex wrench engages the engagement coupler 215 on the first cam 205 and rotates the first cam in a counterclockwise direction as shown in FIG. 7, as indicated by the arrow 255. Rotation of the first cam 205 causes' the teeth 210 to drive the rack 225 to move the first band 230 toward the right, as indicated by the arrow 260 in FIG. 7. This movement of the first band tightens the circumference of the annular implant. If the physician inadvertently adjusts the implant too tight, reversing direction of the engagement coupler 215 will loosen the implant.

In various embodiments according to the present invention, the first and second bands 230, 245 may be separate structures, or they may be opposing ends of the same continuous structure. In such an embodiment, when motion is imparted to the engagement coupler 215, the first cam 205 is rotated, causing the geared teeth 210 to engage the geared rack 225, and causing the first band 239 to move with respect to the second band 245 to adjust the circumference of an implant.

FIG. 9 shows a somewhat different configuration of an exemplary engagement means 300 according to the present invention, in which there is no engagement coupler, and a bracket 350 is provided on both sides of the cams to maintain the first cam 315 and the second cam 320 in close approximation. In one proposed embodiment, the bracket is designed with close tolerances so as to press the first band 330 closely against the second band 345, thereby to hold the bands in fixed relative position by friction. In another proposed embodiment, the brackets 350 are fabricated from an elastic material such that the cams 315, 320 can be spread apart to insert the first band 330 between the cams, whereupon the cams are pulled back together with sufficient force to hold the bands 330, 345 in fixed relative position by friction. In still another proposed embodiment involving an elastic mounting arrangement between the cams 315, 320, the lower edge of the first band 330 and the upper edge of the second band 345 have mating frictional or mechanical surfaces, whereby the cams 315, 320 can be spread apart to permit relative movement between the bands or released to clamp the bands together in fixed relation.

FIG. 10 shows an exemplary attachment means 400 for an implant according to the present invention. The attachment means 400 could be used, for example, in place of the attachment means 25 of the implant 10. The attachment means 400 takes the form of a grommet 410 comprising a wall 415 defining a lumen 420 and an attachment surface 425. Such an attachment means would be used with the implant body extending through the lumen 420 and with fixation devices such as sutures or wires either tied over or affixed through the attachment surface 425.

FIG. 11 shows another alternate embodiment of an attachment means 500 for an implant according to the present invention. The attachment means 500 could also be used, for example, in place of the attachment means 25 of the implant 10. FIG. 11 shows an attachment means 500 in the form of a hollow tube or tube segment 510 comprising a wall 515 defining a lumen 520, an outer surface 525, and an attachment tab 530. Such an attachment means would be used with the implant body extending through the lumen 520 and with fixation devices such as sutures or wires either tied or otherwise affixed over or through the attachment tab 530. Such fixation devices might be placed through holes 535 provided in the attachment tab 530. Alternately a solid attachment tab 530 might be provided, and the fixation devices might be passed through the solid tab. Modifications of these attachment means may be used in conjunction with a sutureless attachment system.

Figure 13:
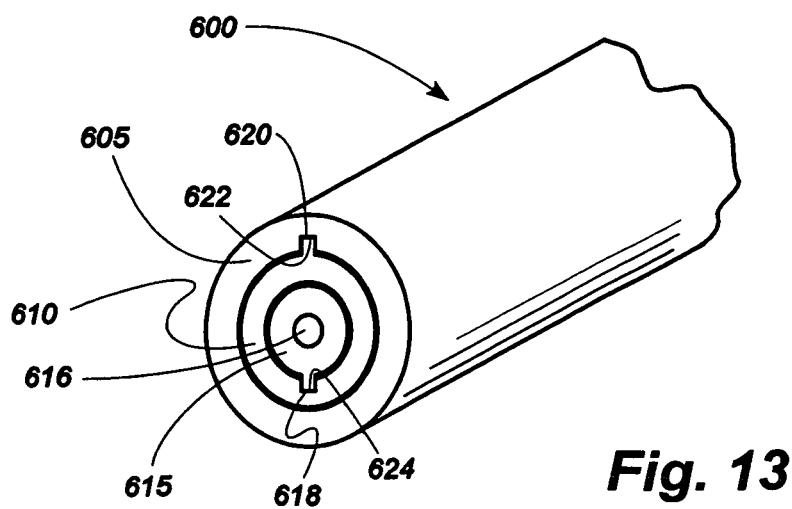
FIG. 13 is a perspective view of one end of the implant of FIG. 12 stowing an optional keyed relationship between three coaxial cannulae to prevent relative rotation between the three components.

FIGS. 12-18 show another embodiment of a percutaneous annuloplasty device according to the present invention, in which an implant/delivery system array 600 includes a housing sheath 605 (not seen in FIG. 12), an actuating catheter 610 coaxially slidably mounted within the housing sheath 605, and a core catheter 615 coaxially slidably mounted within the actuating catheter 610. The core catheter has a central lumen 616 (FIG. 13). The actuating catheter 610 and core catheter 615 may be round tubular structures, or as shown in FIG. 13, either or both of the actuating and core catheters may be provided with one or more keyed ridges 618, 620 respectively to be received by one or more reciprocal slots 622, 624 within the inner lumen of either the housing sheath 665 or the actuating catheter 610, respectively. Such keyed ridges 618, 620 would limit internal rotation of an inner element within an outer element, should such restriction be desirable to maintain control of the inner contents from inadvertent displacement due to undesired rotational motion during use.

The implant/delivery system array 600 includes a distal tip 625 at the forward end of the core catheter 615. One or more radial implant support arms 630 have their distal ends 632 pivotably or bendably mounted to the core catheter 615 adjacent its distal tip 625. The proximal ends 634 of the radial implant support arms 630 normally extend along the core catheter 615 but are capable of being displaced outward away from the core catheter.

One or more radial support struts 636 have their proximal ends 638 pivotably or bendably mounted to the distal end of the actuating catheter 610. The distal end 640 of each radial support strut is 636 pivotably or bendably attached to a midpoint of a corresponding radial implant support arm 630. As the actuating catheter 610 is advanced with respect to the core catheter 615, the radial support struts 636 force the radial implant support arms 630 upward and outward in the fashion of an umbrella frame. Thus the actuating catheter 610, core catheter 615, radial support struts 636, and radial support arms 630 in combination form a deployment umbrella 642.

Figure 14:
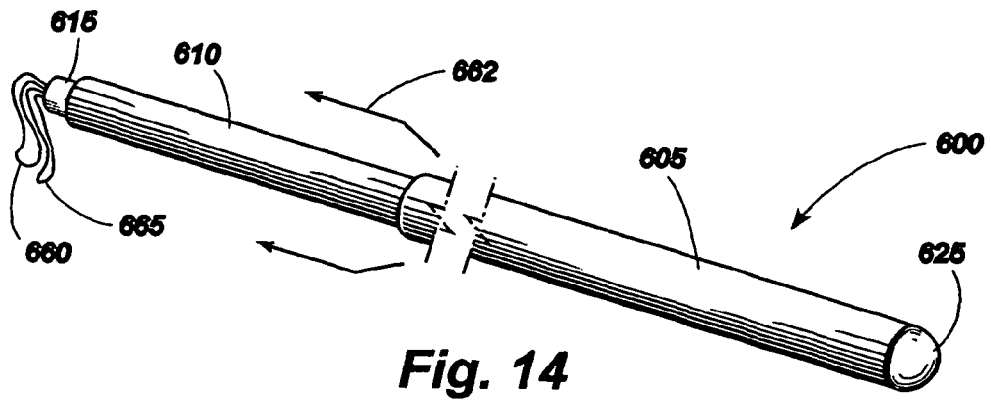
FIG. 14 is a perspective view of the implant of FIG. 12 showing the outer cannula extended to cover the implant.
Figure 15:
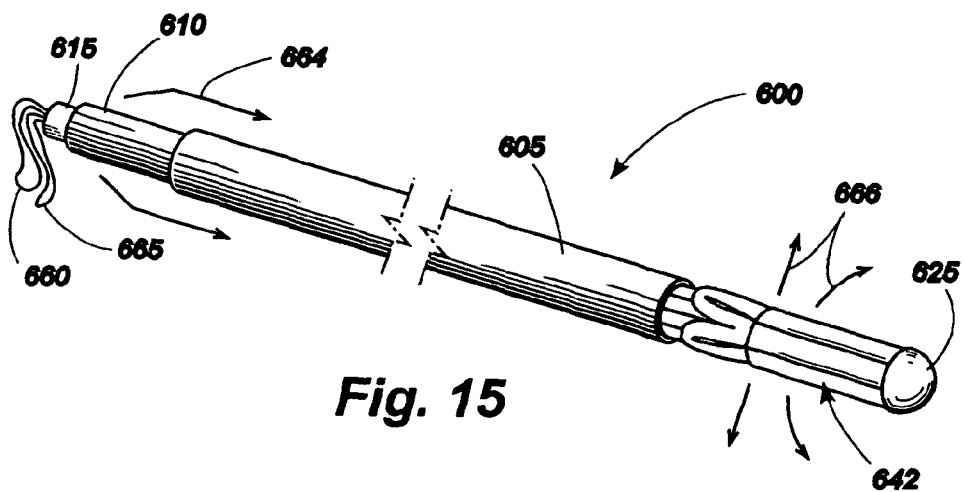
FIG. 15 is a perspective view of the implant of FIG. 12 showing the outer cannula retracted to expose the implant.
Figure 16:
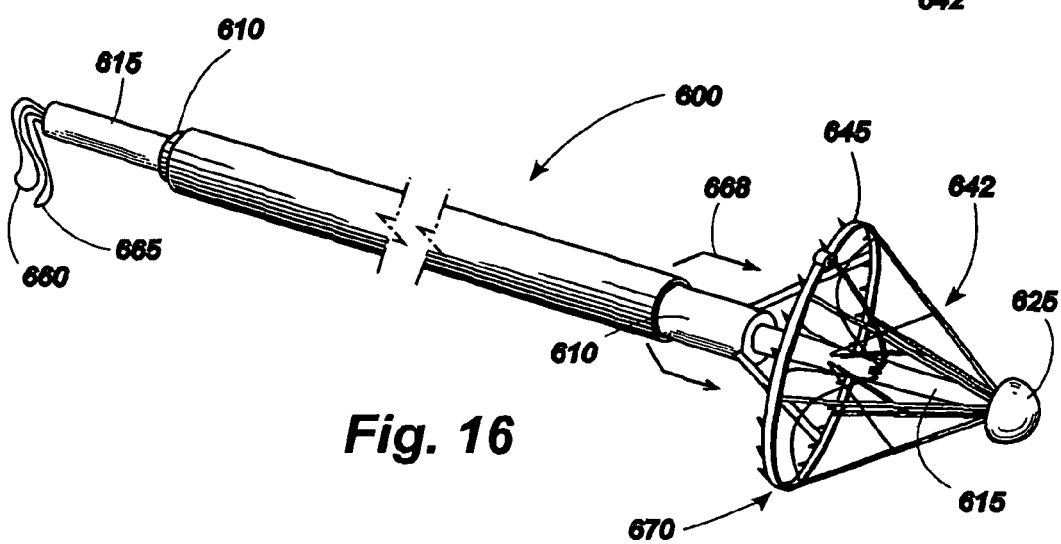
FIG. 16 is a perspective view of the implant of FIG. 12 showing the middle cannula extended to unfold the implant.

A prosthetic implant 645 is releasably attached to the proximal ends 634 of the radial implant support arms 630. Around the periphery of the prosthetic implant 645 and extending proximally there from are a plurality of retention barbs 646. In addition, one or more of the radial implant support arms 630 comprise touchdown sensors 648 whose proximal ends extend proximal to the implant 645. Extending through the central lumen 616 (FIG. 13) of the core catheter 615 in the exemplary embodiment 600 and out lateral ports 650 (FIG. 12) spaced proximally from the distal tip 625 are one or more release elements 660, which serve to release the implant 645 from the delivery system, and one or more adjustment elements 665 which serve to adjust the implant's deployed size and effect. Because the release elements 660 and adjustment elements 665 extend through the proximal end of the core catheter 615, as seen in FIGS. 14-16, these elements can be directly or indirectly instrumented or manipulated by the physician. A delivery interface 670 (FIGS. 12,16) is defined in this example by the interaction of the deployment umbrella 642, the release elements 660, and the implant 645. In the disclosed embodiment, the release elements 660 may be a suture, fiber, or wire in a continuous loop that passes through laser drilled bores in the implant 645 and in the radial implant support arms 630, and then passes through the length of the core catheter 615. In such an embodiment, the implant 645 may be released from the delivery system at a desired time by severing the release element 660 at its proximal end, outside the patient, and then withdrawing the free end of the release element 660 through the core catheter 610.

FIGS. 14-16 show the operation of the implant/delivery system array 600, in which an umbrella-like expansion of the prosthetic implant 645 is achieved by sliding movement of the housing sheath 605, the actuating catheter 610, and the core catheter 615. Referring first to FIG. 14, the housing sheath 605 is extended to cover the forward ends of the actuating catheter 610 and core catheter 615 for intravascular insertion of the implant/delivery system array 600. From this starting position, the housing sheath 605 is retracted in the direction indicated by the arrows 662. In FIG. 15 the housing sheath 605 has been retracted to expose the forward end of the actuating catheter 610 and the collapsed deployment umbrella 642. From this position the actuating catheter 610 is advanced in the direction indicated by the arrows 664. This will cause the deployment umbrellas to expand in the directions indicated by the arrows 666. FIG. 16 shows the expansion of the deployment umbrella 642 produced by distal motion of the actuating catheter 610 relative to the core catheter 615. After the implant 645 has been positioned and adjusted to the proper size, the housing sheath 605 is advanced in the direction indicated by the arrows 668 to collapse and to cover the deployment umbrella 642 for withdrawal of the device from the patient.

Figure 17:
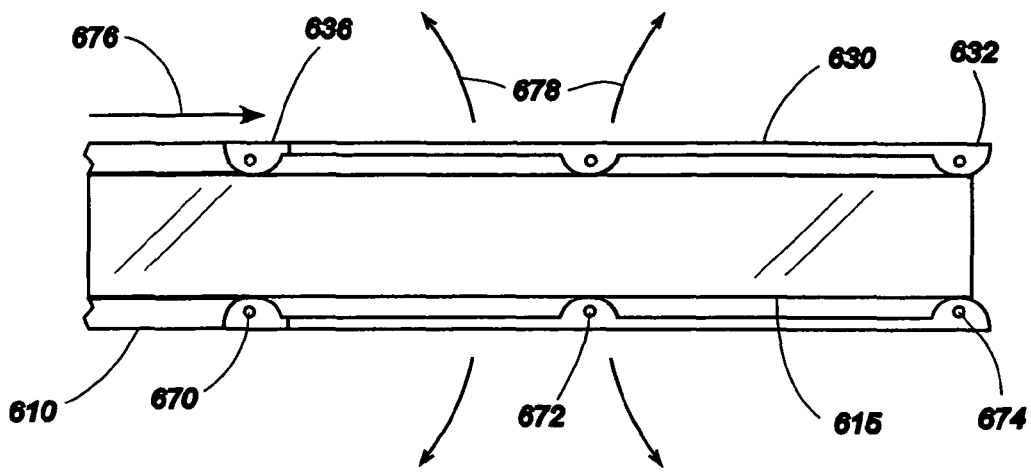
FIGS. 17 and 18 are schematic views illustrating how extension of the middle cannula causes the implant to unfold, where
Figure 18:
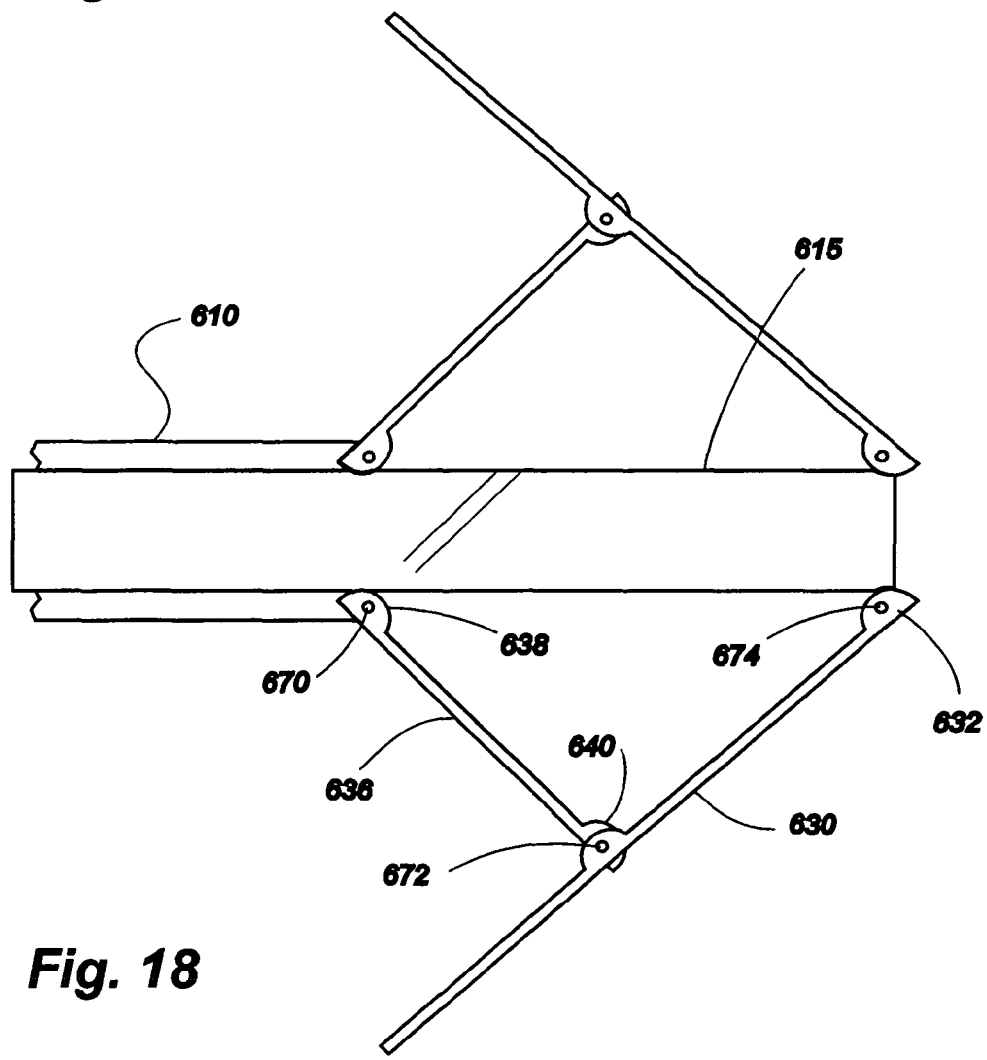

FIGS. 17 and 18 are schematic views illustrating the radial implant support arms 630 and the radial support struts 636 of the implant/delivery system array 600. In FIG. 17, a radial support strut 636 is pivotably attached at its proximal end 638 at a first pivotable joint 670 to the actuation catheter 610. The radial support strut 636 is attached at its distal end 640 to a second pivotable joint 672 at an intermediate point of a corresponding radial implant support arm 630. The radial implant support arm 630 is attached at its distal end 632 by a third pivotable joint 674 to the core catheter 620. FIG. 17 shows the assembly in a closed state. When the actuation catheter 610 is advanced distally over the core catheter 615, as shown by the arrows 676, the radial support strut 636 and the radial implant support arm 630 are extended by the motion at the first pivotable joint 670, the second pivotable joint 672, and the third pivotable joint 674, as shown by the arrow 678. This motion has the effect of expanding the deployment umbrella and folded implant (not shown in FIGS. 17 and 18), allowing it to achieve its greatest radial dimension, prior to engagement and implantation as previously discussed with reference to FIGS. 12-16.

Figure 19:
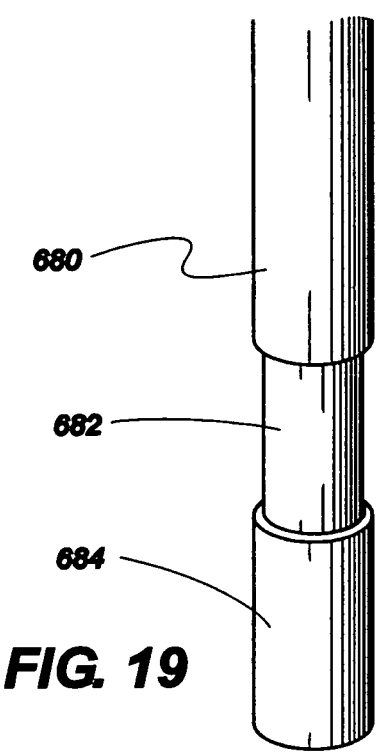
FIG. 19 is a perspective view of the lower end of a touchdown sensor of the implant of FIG. 12, showing the sensor in an uncompressed condition.
Figure 20:
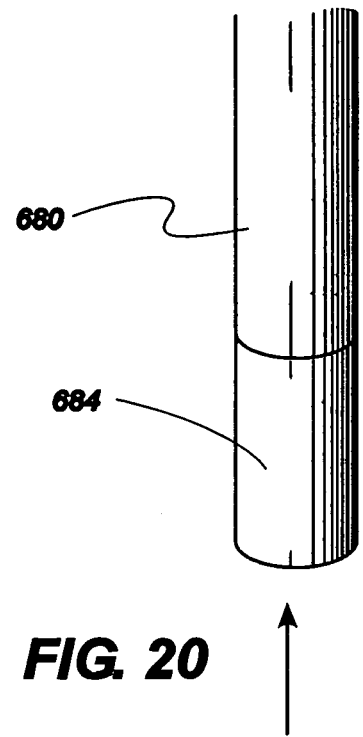
FIG. 20 is a perspective view of the lower end of the touchdown sensor of FIG. 19, showing the sensor in a compressed condition.

FIGS. 19 and 20 show further details of the touchdown sensors 648 shown previously in FIG. 12. The touchdown sensor 648 of FIGS. 19 and 20 includes a distal segment 680, an intermediate segment 682, and a proximal segment 684. The distal segment 680 is spring-mounted, so that it is capable of slidable, telescoping displacement over the intermediate segment 682 to achieve a seamless junction with the proximal segment 684 upon maximal displacement. When the touchdown sensor 648 is in its normal condition, the spring extends the proximal segment such that the sensor assumes the orientation shown in FIG. 19. When the implant 645 (FIG. 12) is seated against the periphery of an anatomical opening, the proximal segment 684 of the sensor 648 is compressed against the distal segment 680, as shown in FIG. 20. The distal segment 680 and the proximal segment 684 are both constructed of, are sheathed by, or otherwise covered with a radio-opaque material. However, the intermediate segment 682 is not constructed or coated with such a radio-opaque material. Therefore, when the distal segment 680 is at rest, it is fully extended from the proximal segment 684, and the gap represented by the exposed intermediate segment 682 is visible on radiographic examination. However, when the distal segment 680 is brought to maximum closeness with the proximal segment 684, no such radio-opaque gap is radiographically visible, and the touchdown sensor is said to be "activated". This embodiment allows radiographic monitoring of the position of the touchdown sensor 648 with respect to the degree of extension of the distal catheter segment 680. In the embodiment according to the present invention as shown, one or more touchdown detectors 648 are employed to ascertain that the delivery system for the prosthetic device is located in the proper position to deploy the implant into the mitral annulus. As this anatomic structure cannot be directly identified on fluoroscopy or standard radiographic procedures, such precise location could be otherwise difficult. At the same time, precise localization and engagement of the mitral annulus is critical for proper implant function and safety.

Touchdown detectors within the embodiments according to the present invention can have a multiplicity of forms, including the telescoping, spring-loaded, radio-opaque elements joined by a non-radio-opaque element as in the aforementioned examples. In embodiments employing magnetic resonance imaging, touchdown detectors according to the present invention may utilize metallic segments interposed by nonmetallic segments in a similar telescoping, spring-loaded array. Other embodiments include a visually-evident system with telescoping, spring-loaded elements with color-coded or other visual features for procedures in which direct or endoscopic observation would be possible. Still other embodiments of touchdown detectors according to the present invention include touchdown detectors provided with microswitches at their tips, such that momentary contact of sufficient pressure completes an electrical circuit and signals the activation of the touchdown detector to the operator. Still other touchdown detectors according to the present invention are provided with fiberoptic pathways for Rahmen laser spectroscopy or other spectral analytical techniques which are capable of detecting unique tissue qualities of the tissue at the desired site for implantation. In addition, still other embodiments according to the present invention include touchdown detectors containing electrodes or other electronic sensors capable of detecting and signaling the operator when a desired electrophysiologic, impedance, or other measurable quality of the desired tissue is detected for proper implantation. Such electrophysiologic touchdown detectors may include electrical circuits that produce visual, auditory, or other signals to the operator that the detectors are activated and that the implant is in the proper position for attachment.

In yet other embodiments according to the present invention, other intracardiac or extracardiac imaging techniques including, but not limited to, intravascular ultrasound, nuclear magnetic resonance, virtual anatomic positioning systems, or other imaging techniques may be employed to confirm proper positioning of the implant, obviating the need for the touchdown sensors as previously described.

Figure 21:
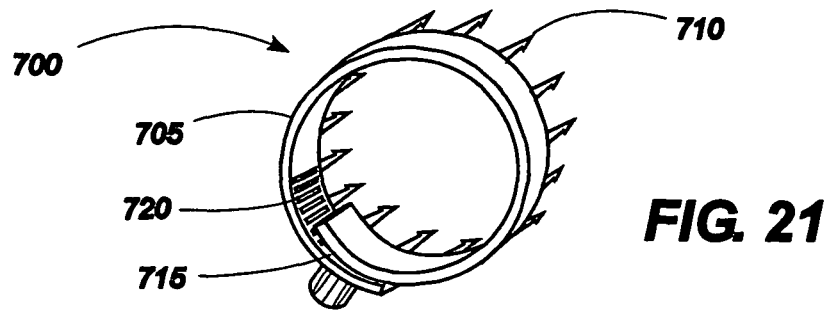
FIG. 21 is a perspective end view of a fourth embodiment of an implant for reducing the circumference of an anatomic orifice.
Figure 22:
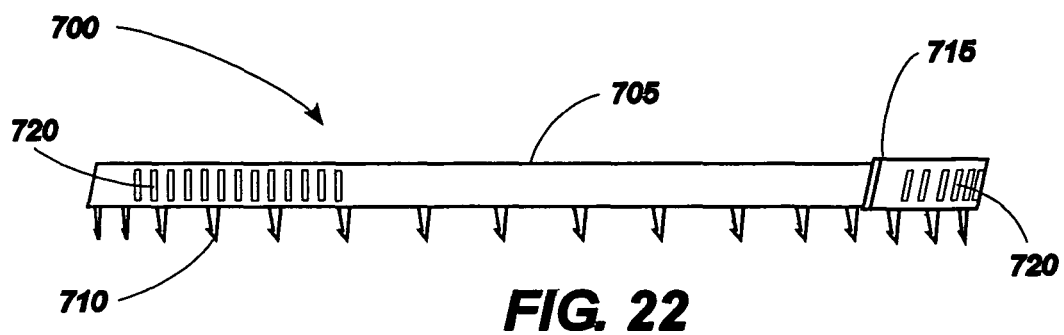
FIG. 22 is a side view of the implant of FIG. 21 with the implant opened up to show its full length.
Figure 23:
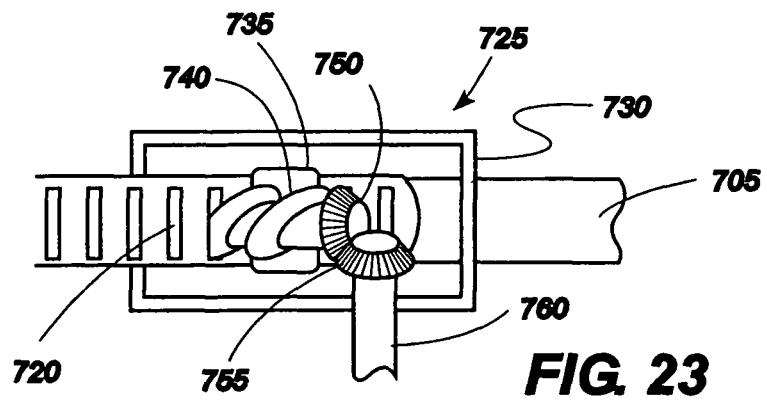
FIG. 23 is a side view of the adjustment mechanism of the implant of FIG. 21.

FIGS. 21-24 show an implant 700 according to one embodiment of the present invention. In this embodiment, the implant body 705 is bandlike and flexible. Through much of its length, the implant body 705 is provided with a series of retention barbs 710 which are oriented to facilitate placement, retention, and removal of the device. The implant body 705 is also provided with an adjustable section 715, which is provided in this example with a series of adjustment stops 720. The adjustment stops 720 may be slots, holes, detents, dimples, ridges, teeth, raised elements, or other mechanical features to allow measured adjustment of the implant 700 in use. In the embodiment shown in FIGS. 21-24, the adjustment stops 720 are engaged by a geared connector 725. FIG. 21 is an end view, showing the implant body 705 curved on itself, with the retention barbs 710 to the exterior, and with the adjustable section 715 passing through its engagement with the geared connector 725 and curving internally within the implant body 705 to form a closed, round structure. FIG. 23 shows details of an exemplary geared connector 725, in which a housing 730 is connected to the implant body 705. The housing 730 contains and supports a mechanical worm 740 with an attached first geared head 750 which mates with a second geared head 755. The second geared head 755 is attached to an adjustment stem 760 which is machined to receive a screwdriver-like adjustment element. The various embodiments according to the present invention may require a number of forms of adjustment elements. In the present example, the adjustment element is provided as a finely coiled wire with a distal tip machined to be received by a receiving slot in the adjustment stem 760 (not shown). The relationship between the distal tip of the adjustment element and the adjustment stem 760 is mechanically similar to a screwdriver bit and screwhead, such that torsion imparted to the adjustment means by the operator will result in the turning of the adjustment stem 760 and second geared bead 755 allows motion of the first geared head 750 and worm 740, which creates motion of the adjustable implant section 715 as the worm engages with the series of adjustment tops 725. Excess length of the adjustable section 715 passes though a band slot 735 (FIG. 23), thus allowing the band to move concentrically inside the closed implant body 705. The adjustment element in this embodiment may be designed to remain in place after the deployment umbrella has been retracted and withdrawn. The connection between the adjustment element's distal tip and the adjustment stem 760 may be a simple friction connection, a mechanical key/slot formation, or may be magnetically or electronically maintained.

Figure 24:
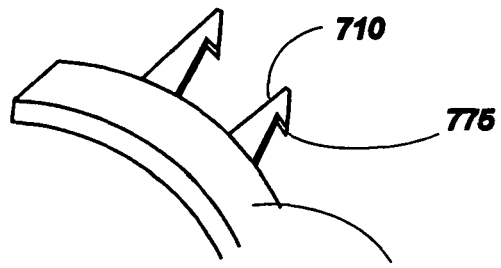
FIG. 24 is a close-up view of two of the retention barbs of the implant of FIG. 21.

As further shown in FIG. 21, the exemplary embodiment employs unidirectional retention barbs 710 which are attached to the outer perimeter of the implant body 705. The retention barbs 710 are oriented in a consistent, tangential position with respect to the implant body 705 such that rotational motion of the implant body will either engage or release the retention barbs 710 upon contact with the desired tissue at the time of deployment. This positioning of the retention barbs 710 allows the operator to "screw in" the implant 700 by turning the implant 700 upon its axis, thus engaging the retention barbs 710 into the adjacent tissue. As shown in FIG. 24, the retention barbs 710 may each be further provided with a terminal book 775 at the end which would allow for smooth passage through tissue when engaging the retention barbs 710 by rotating the implant 700, without permitting the implant 700 to rotate in the opposite direction, because of the action of the terminal books 775 grasping the surrounding tissue (much like barbed fish books). The terminal books 775 thus ensure the seating of the implant 700 into the surrounding tissue.

Figure 25:
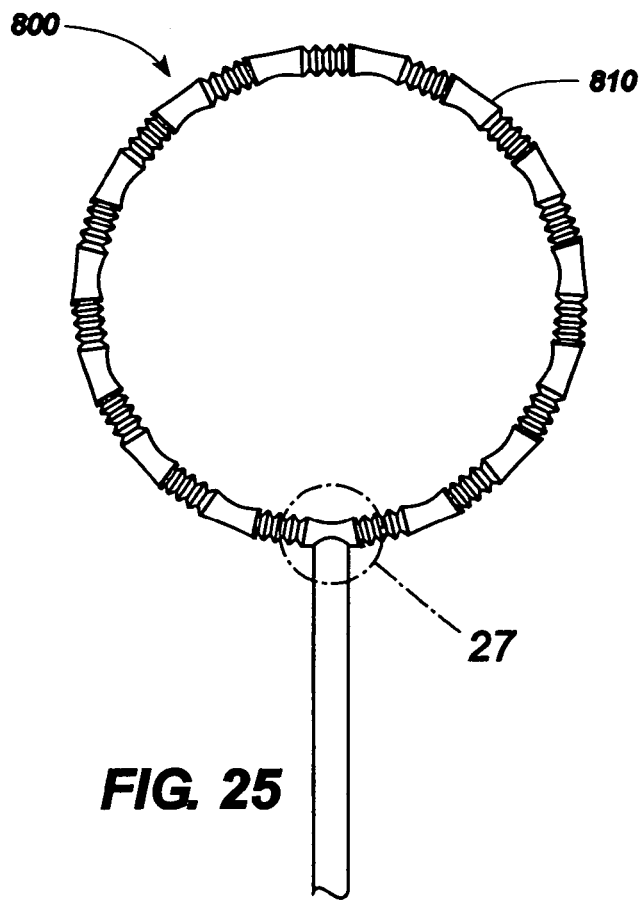
FIG. 25 is a front view of a fifth embodiment of an implant for reducing the circumference of an anatomic orifice, with the implant shown in its expanded configuration.
Figure 26:
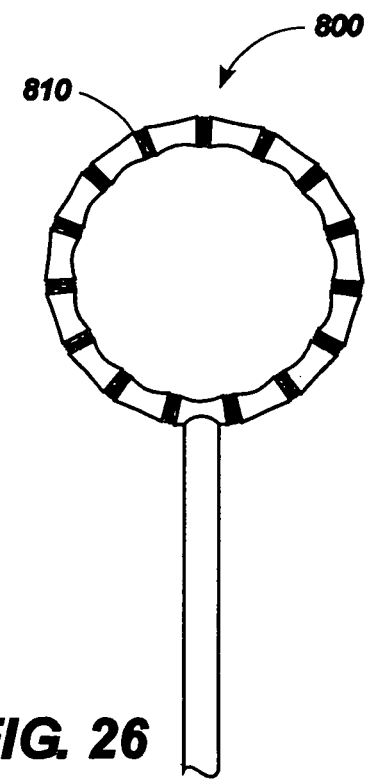
FIG. 26 is a front view of the implant of FIG. 25, with the, implant shown in its contracted configuration.
Figure 27:
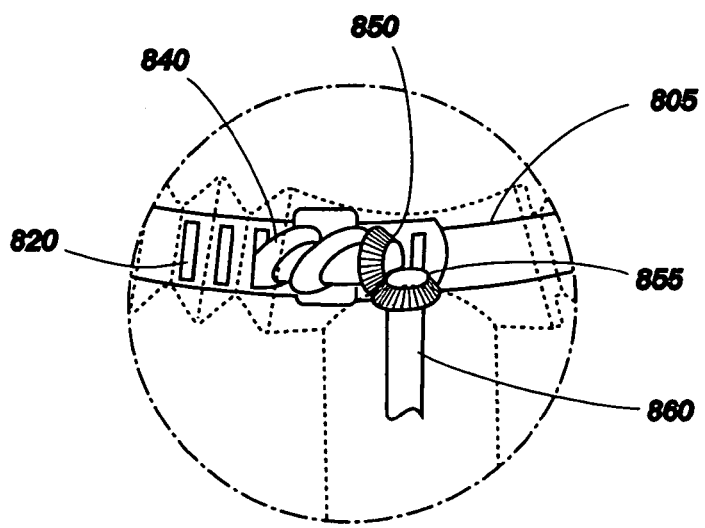
FIG. 27 is an enlarged view of the area indicated by the circle 27 in FIG. 25, with the outer body removed to show interior detail.

FIGS. 25-27 illustrate another embodiment of an implant 800 as contemplated according to the present invention. The implant 800 includes a band 805 (FIG. 27), but the retention barbs of the previous example have been eliminated in favor of an outer fabric implant sheath 810. The fabric sheath 810 can be sutured or otherwise affixed to the anatomic tissue in a desired location. The circumference of the implant body 800 is adjusted through a geared connector 825 similar to the geared connector of the bandlike implant array shown in FIG. 23. More specifically, adjustment stops 820 on the band are engaged by a mechanical worm 840 with an attached first geared bead 850. The first geared head 850 mates with a second geared head 855. The second geared bead 855 is attached to an adjustment stem 860 which is machined to receive a screwdriver-like adjustment element.

Figure 28:
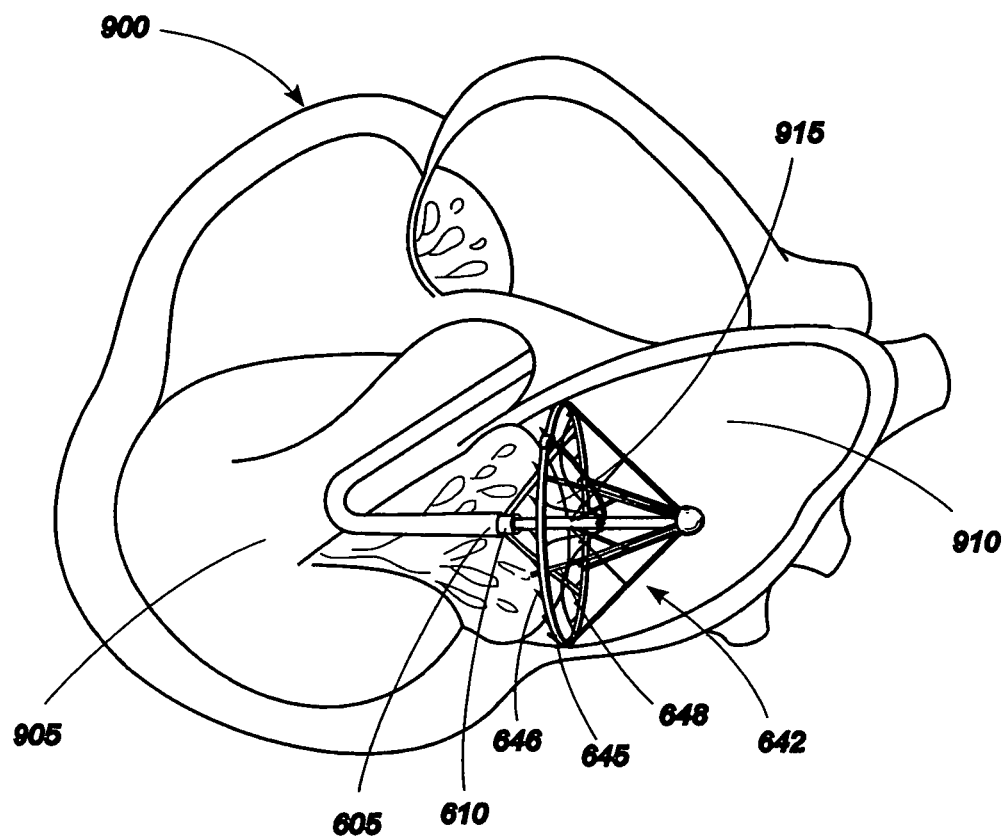
FIG. 28 is a schematic view showing the implant of FIG. 12 anatomically positioned at the mitral annulus in a heart with the implant in a fully expanded state.

FIG. 28 illustrates an example of the method of use of an implant/delivery system array 600 for positioning an implant 645 in a patient with ischemic annular dilatation and mitral regurgitation. Peripheral arterial access is obtained via conventional cutdown, arterial puncture, or other standard access techniques. After access to the arterial system is attained; guidewire placement is per-formed and intravascular access to the heart, 900 is obtained using fluoroscopic, ultrasound, three-dimension ultrasound, magnetic resonance, or other real-time imaging techniques. The guidewire, deployment device, and implant are passed through the aortic valve in a retrograde fashion into the left ventricle 905 and then into the left atrium 910. At this point, the operator retracts the housing sheath 605, thus unsheathing the collapsed deployment umbrella 642 and implant 645. The deployment umbrella 642 is then distended by the distal motion of the actuation catheter, causing the radial support arms and struts to fully distend. At this point, the touchdown detectors 648 are not in contact with any solid structures, and are fully extended with their radiolucent gaps visible on the imaging system. Once the deployment umbrella is distended, the entire assembly is pulled back against the area of the mitral valve 915. At least two touchdown detectors 648 are employed in a preferred embodiment according to the present invention. When all touchdown detectors show the disappearance of their intermediate, non-opaque, intermediate segments and are thus activated, then the deployment umbrella must be in contact with the solid tissue in the region of the mitral annulus/atrial tissue, and further implant deployment and adjustment may proceed. However, if any one touchdown sensor is not activated, and a radiolucent gap persists, then the device is not properly positioned, and must be repositioned before further deployment. Thus, the touchdown sensor system may assist in the deployment and adjustment of prosthetic devices by the delivery system according to the present invention. Once properly positioned, the operator rotates the actuation catheter in a prescribed clockwise or counterclockwise manner to engage the retention barbs on the implant into the tissue in the region of the mitral annulus/atrial tissue. Should re-positioning be required, a reverse motion would disengage the retention barbs from the annular/atrial tissue, and repositioning may be performed, again using the touchdown detectors for proper placement. Once firmly seated, the adjustment element(s) are operated to achieve the desired degree of annular reduction. Real-time trans esophageal echocardiography, intravascular echocardiography, intracardiac echocardiography, or other modalities for assessing mitral function may then be employed to assess the physiologic effect of the repair on mitral function, and additional adjustments may be performed. Once a desired result has been achieved, the release elements are activated to detach the implant from the deployment umbrella. The operator then retracts the actuation catheter and extends the housing sheath, collapsing the deployment umbrella, and covering the components for a smooth and atraumatic withdrawal of the device from the heart and vascular system.

If desired, the adjustment elements may be left in position after the catheter components are withdrawn for further physiologic adjustment. In yet other embodiments according to the present invention, a catheter-based adjustment elements may subsequently be re-inserted though a percutaneous or other route. Such an adjustment element may be steerably operable by the operator, and may be provided with magnetic, electronic, electromagnetic, or laser-guided systems to allow docking of the adjustment element with the adjustable mechanism contained within the implant. In still other embodiments, the adjustment mechanism may be driven by implanted electromechanical motors or other systems, which may be remotely controlled by electronic flux or other remote transcutaneous or percutaneous methods.

In the case of pulmonic valve repair, initial catheter access is achieved through a peripheral or central vein. Access to the pulmonary valve is also achieved from below the valve once central venous access is achieved by traversing the right atrium, the tricuspid valve, the right ventricle, and subsequently reaching the pulmonic valve.

In yet other embodiments according to the present invention, catheter access to the left atrium can be achieved from cannulation of central or peripheral veins, thereby achieving access to the right atrium. Then a standard atrial trans-septal approach may be utilized to access the left atrium by creation of an iatrogenic atrial septal defect (ASD). In such a situation, the mitral valve may be accessed from above the valve, as opposed to the retrograde access described in Example 1. The implant and a reversed deployment umbrella may be utilized with implant placement in the atrial aspect of the mitral annulus, with the same repair technique described previously. The iatrogenic ASD may then be closed using standard device methods. Access to the aortic valve may also be achieved from above the aortic valve via arterial access in a similar retrograde fashion.

Figure 29:
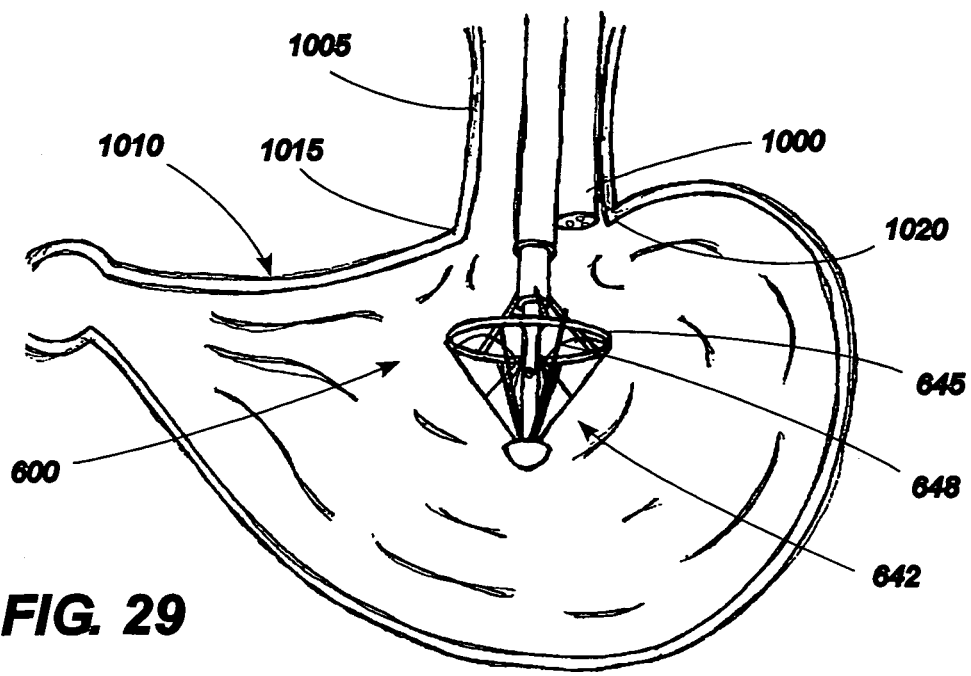
FIG. 29 is a schematic view showing the implant of FIG. 12 anatomically positioned at the gastroesophageal opening with the implant in a fully expanded state.
Figure 30:
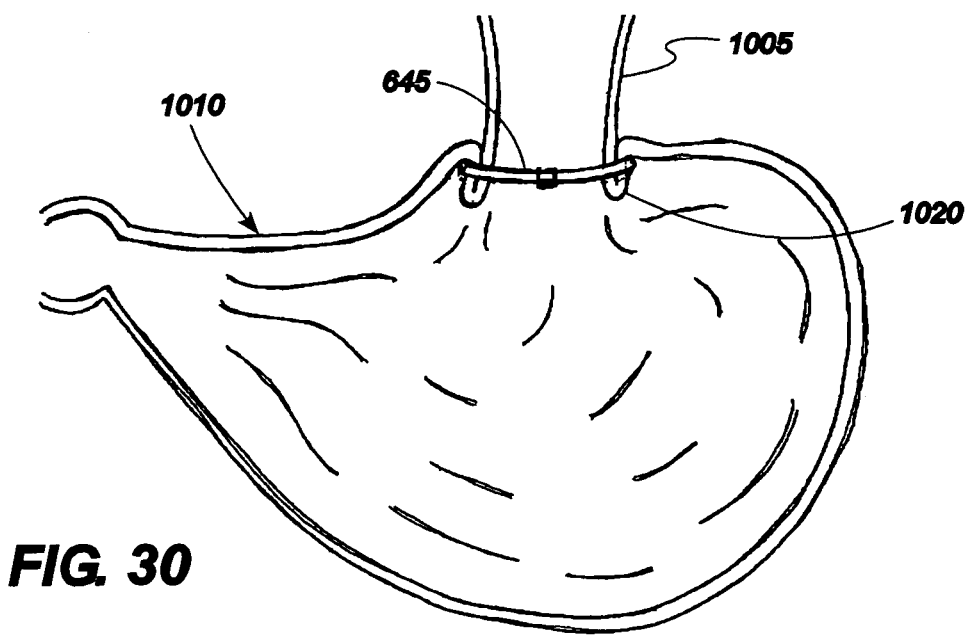
FIG. 30 is a schematic view showing the implant of FIG. 29 implanted to reduce the circumference of the gastroesophageal opening.

Other embodiments of the adjustable implant and methods according to the present invention include gastrointestinal disorders such as gastroesophageal reflux disease (GERD), a condition in which the gastro-esophageal (GE) junction lacks adequate sphincter tone to prevent the reflux of stomach contents into the esophagus, causing classic heartburn or acid reflux. This not only results in discomfort, but also may cause trauma to the lower esophagus over time that may lead to the development of pre-cancerous lesions (Barrett's esophagus) or adenocarcinoma of the esophagus at the GE junction. Surgical repair of the GE junction has historically been achieved with the Nissen Fundoplication, an operative procedure with, generally good results. However, the Nissen procedure requires general anesthesia and a hospital stay. Utilizing the devices and methods according to the present invention, an adjustable implant would obviate the need for a hospital stay and be performed in a clinic or gastroenterologist's office. Referring now to FIGS. 29 and 30, an umbrella deployment device 600 with implant 645 is passed under guidance of an endoscope 1000, through the patient's mouth, esophagus 1005, and into the stomach 1010, where the deployment device 600 is opened with expansion of the implant 645 and touchdown detectors 648 with a color-coded or otherwise visible gap. The touchdown detectors are then engaged onto the stomach around the gastroesophageal junction 1015 under direct endoscopic control until all touchdown detectors 648 are visually activated. The implant is then attached to the stomach wall, 1020 the umbrella 642 is released and withdrawn, leaving behind the implant 645 and the adjustment elements. The implant is then adjusted until the desired effect is achieved, i.e., minimal acid reflux either by patient symptoms, pH monitoring of the esophagus, imaging studies, or other diagnostic means. If the patient should suffer from gas bloat, a common complication of gastroesophageal junction repair in which the repair is too tight and the patient is unable to belch, the implant can be loosened until a more desirable effect is achieved.

In various embodiments anticipated by the present invention, the implant body may be straight, curved, circular, ovoid, polygonal, or some combination thereof. In various embodiments anticipated by the present invention the implant may be capable of providing a uniform or non-uniform adjustment of an orifice or lumen within the body. The implant body may further completely enclose the native recipient anatomic site, or it may be provided in an interrupted form that encloses only a portion of the native recipient anatomic site. In still other embodiments of the present invention, the implant body may be a solid structure, while in yet other embodiments the implant body may form a tubular or otherwise hollow structure. In one embodiment of the present invention, the body may further be a structure with, an outer member, an inner member, and optional attachment members. In such an embodiment, the outer member of the implant body may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or non-woven configuration. The outer member in such an embodiment also serves to house the inner member. In this embodiment, the inner member provides an adjustment means that, when operated by an adjustment mechanism, is capable of altering the shape and/or size of the outer member in a defined manner.

In alternate embodiments according to the present invention, the adjustment means may be located external to or incorporated within the outer member. In yet additional alternate embodiments contemplated by the present invention, the implant body may consist of an adjustment means without a separate outer member covering said adjustment means.

In various embodiments according to the present invention, the adjustment means may include a mechanism which may be threaded or nonthreaded, and which may be engaged by the action of a screw or worm screw, a friction mechanism, a friction-detent mechanism, a toothed mechanism, a ratchet mechanism, a rack and pinion mechanism, or such other devices to permit discreet adjustment and retention of desired size a desired position, once the proper size is determined.

In yet other embodiments according to the present invention, the adjustment means may comprise a snare or purse string-like mechanism in which a suture, a band, a wire or other fiber structure, braided or non-braided, monofilament or multifilament, is capable of affecting the anatomic and/or physiologic effects of the implant device on a native anatomic recipient site upon varying tension or motion imparted to said wire or fiber structure by a surgeon or other operator. Such an adjustment means may be provided as a circular or non-circular structure in various embodiments. Changes in tension or motion may change the size and/or shape of the implant.

In various embodiments according to the present invention, the adjustment means may be a metallic, plastic, synthetic, natural, biologic, or any other biologically-compatible material, or combination thereof. Such adjustment means may further be fabricated by extrusion or other molding techniques, machined, or woven. Furthermore, in various embodiments of the present invention, the adjustment means may be smooth or may include slots, beads, ridges, or any other smooth or textured surface.

In various embodiments of the present invention, the implant body may be provided with one or more attachment members such as grommets or openings or other attachment members to facilitate attachment of the implant to the native recipient site. In alternate embodiments, the implant body may attach to or incorporate a mechanical tissue interface system that allows a sutureless mechanical means of securing the implant at the native recipient site. In still other alternate embodiments, sutures or other attachment means may be secured around or through the implant body to affix the implant body to the native recipient site. In yet other embodiments of the present invention, mechanical means of securing the implant body to the native recipient site may be augmented or replaced by use of fibrin or other biologically-compatible tissue gives or similar adhesives.

In additional various embodiments according to the present invention, the adjustable implant may be employed to adjustably enlarge or maintain the circumference or other dimensions of an orifice, ostium, lumen, or anastomosis in which a disease process tends to narrow or constrict such circumference or other dimensions.

In various embodiments according to the present invention, an adjustment mechanism may be provided to interact with the adjustment means to achieve the desired alteration in the size and/or position of the adjustment means. Such an adjustment mechanism may include one or more screws, worm-screw arrays rollers, gears, frictional stops, a friction-detent system, ratchets, rack and pinion arrays, micro-electromechanical systems, other mechanical or electromechanical devices or some combination thereof.

In some embodiments as contemplated by the present invention, an adjustment too] may be removably or permanently attached to the adjustment mechanism and disposed to impart motion to the adjustment mechanism and, in turn, to the adjustment means to increase or decrease the anatomic effect of the implant on the native recipient site.

In alternate embodiments according to the present invention, micromotor arrays with one or more micro-electromechanical motor systems with related electronic control circuitry may be provided as an adjustment means, and may be activated by remote control through signals convey by electromagnetic radiation or by direct circuitry though electronic conduit leads which may be either permanently or removably attached to said micromotor arrays.

In still other various embodiments according to the present invention, the adjustment mechanism may be provided with a locking mechanism disposed to maintain the position of the adjustment means in a selected position upon achievement of the optimally desired anatomic and/or physiologic effect upon the native recipient site and the bodily organ to which it belongs. In other embodiments, no special locking mechanism may be necessary due to the nature of the adjustment means employed.

In yet other alternate embodiments according to the present invention, the adjustment means and/or the outer member structure may be a pliable synthetic material capable of rigidification upon exposure to electromagnetic radiation of selected wavelength, such as ultraviolet light. In such embodiments, exposure to the desired electromagnetic radiation may be achieved by external delivery of such radiation to the implant by the surgeon, or by internal delivery of such radiation within an outer implant member using fiberoptic carriers placed within said outer member and connected to an appropriate external radiation source. Such fiberoptic carriers may be disposed for their removal in whole or in part from the outer implant member after suitable radiation exposure and hardening of said adjustment means.

The present invention also provides methods of using an adjustable implant device to selectively alter the anatomic structure and/or physiologic effects of tissues forming a passageway for blood, other bodily fluids, nutrient fluids, semi-solids, or solids, or wastes within a mammalian body. Various embodiments for such uses of adjustable implants include, but are not limited to, open surgical placement of said adjustable implants at the native recipient site through an open surgical incision, percutaneous or intravascular placement of said implants under visual control employing fluoroscopic, ultrasound, magnetic resonance imaging, or other imaging technologies, placement of said implants through tissue structural walls, such as the coronary sinus or esophageal walls, or methods employing some combination of the above techniques. In various embodiments as contemplated by the present invention, adjustable implants may be placed and affixed in position in a native recipient anatomic site by trans-atrial, trans-ventricular, trans-arterial, trans-venous (i.e., via the pulmonary veins) or other routes during beating or non-beating cardiac surgical procedures or endoscopically or percutaneously in gastrointestinal surgery.

Furthermore, alternate methods for use of an adjustable implant device may provide for the periodic, post-implantation adjustment of the size of the anatomic structure receiving said implant device as needed to accommodate growth of the native recipient site in a juvenile patient or other changes in the physiologic needs of the recipient patient.

Adjustment of the adjustable implants and the methods for their use as disclosed herein contemplates the use by the surgeon or operator of diagnostic tools to provide an assessment of the nature of adjustment needed to achieve a desired effect. Such diagnostic tools include, but are not limited to, transesophageal echocardiography, echocardiography, diagnostic ultrasound, intravascular ultrasound, virtual anatomic positioning systems integrated with magnetic resonance, computerized tomographic, or other imaging technologies, endoscopy, mediastinoscopy, laparoscopy, thoracoscopy, radiography, fluoroscopy, magnetic resonance imaging, computerized tomographic imaging, intravascular flow sensors, thermal sensors or imaging, remote chemical or spectral analysis, or other imaging or quantitative or qualitative analytic systems.

In one aspect, the implant/delivery system of the present invention comprises a collapsible, compressible, or distensible prosthetic implant and a delivery interface for such a prosthetic implant that is capable of delivering the prosthetic implant to a desired anatomic recipient site in a collapsed, compressed, or non-distended state, and then allowing controlled expansion or distension and physical attachment of such a prosthetic implant by a user at the desired anatomic recipient site. Such a system permits the delivery system and prosthetic implant to be introduced percutaneously through a trocar, sheath, via Seldinger technique, needle, or endoscopically through a natural bodily orifice, body cavity, or region and maneuvered by the surgeon or operator to the desired anatomic recipient site, where the delivery system and prosthetic implant may be operably expanded for deployment. When desirable, the implant/delivery system according to the present invention is also capable of allowing the user to further adjust the size or shape of the prosthetic implant once it has been attached to the desired anatomic recipient site. The delivery system according to the present invention is then capable of detaching from its interface with the prosthetic implant and being removed from the anatomic site by the operator. The delivery system and prosthetic implant may be provided in a shape and size determined by the anatomic needs of an intended native recipient anatomic site within a mammalian patient. Such a native recipient anatomic site may be a heart valve, the esophagus near the gastro-esophageal junction, the anus, or other anatomic sites within a mammalian body that are creating dysfunction that might be relieved by an implant capable of changing the size and shape of that site and maintaining a desired size and shape after surgery.

In various embodiments contemplated by the present invention, the delivery system may be a catheter, wire, filament, rod, tube, endoscope, or other mechanism capable of reaching the desired recipient anatomic site through an incision, puncture, trocar, or through an anatomic passageway such as a vessel, orifice, or organ lumen, or trans-abdominally or trans-thoracically. In various embodiments according to the present invention, the delivery system may be steerable by the operator. The delivery system may further have a delivery interface that would retain and convey a prosthetic implant to the desired recipient anatomic site. Such a delivery interface may be operably capable of distending, reshaping, or allowing the independent distension or expansion of such a prosthetic implant at the desired recipient anatomic site. Furthermore, such a delivery interface may provide an operable means to adjust the distended or expanded size, shape, or physiologic effect of the prosthetic implant once said implant has been attached in situ at the desired recipient anatomic site. In various embodiments according to the present invention, such adjustment may be carried out during the procedure in which the implant is placed, or at a subsequent time. Depending upon the specific anatomic needs of a specific application, the delivery interface and the associated prosthetic implant may be straight, curved, circular, helical, tubular, ovoid, polygonal, or some combination thereof. In still other embodiments of the present invention, the prosthetic implant may be a solid structure, while in yet other embodiments the prosthetic implant may form a tubular, composite, or otherwise hollow structure. In one embodiment of the present invention, the prosthetic implant may further be a structure with an outer member, an inner member, and optional attachment members. In such an embodiment, the outer member of the prosthetic implant may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or non-woven configuration. The outer member in such an embodiment also serves to house the inner member. In this embodiment, the inner member provides an adjustment means that, when operated by an adjustment mechanism, is capable of altering the shape and/or size of the outer member in a defined manner.

In some embodiments according to the present invention, at least some portions of the adjustable inner or outer member may be elastic to provide an element of variable, artificial muscle tone to a valve, sphincter, orifice, or lumen in settings where such variability would be functionally valuable, such as in the treatment of rectal incontinence or vaginal prolapse.

In various embodiments according to the present invention, the delivery interface would have an attachment means to retain and convey the prosthetic implant en route to the native anatomic recipient site and during any in situ adjustment of the prosthetic implant once it has been placed by the operator. Such an attachment means would be operably reversible to allow detachment of the prosthetic implant from the delivery interface once desired placement and adjustment of the prosthetic implant has been accomplished.

Figure 31:
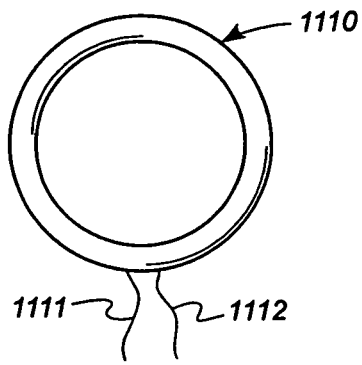
FIG. 31 is a plan view of a first embodiment of a drawstring implant in its normal state.
Figure 32:
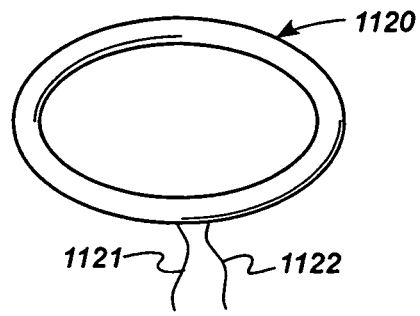
FIG. 32 is a plan view of the implant of FIG. 31 in a cinched state.
Figure 33:
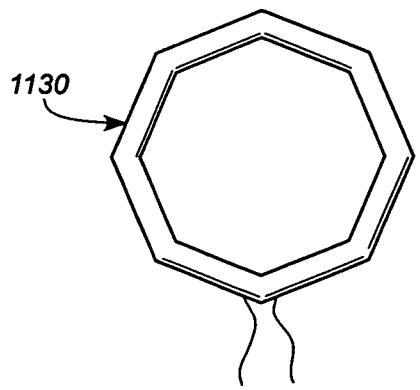
FIG. 33 is a plan view of a second embodiment of a drawstring implant in its normal state.
Figure 34:
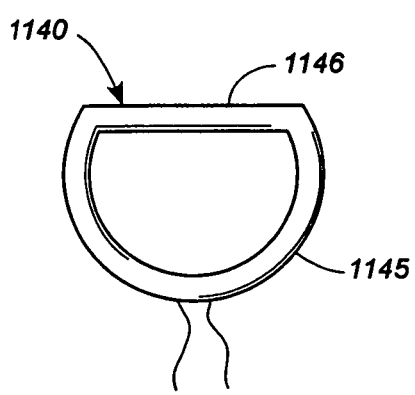
FIG. 34 is a plan view of a third embodiment of a drawstring implant in its normal state.
Figure 35:
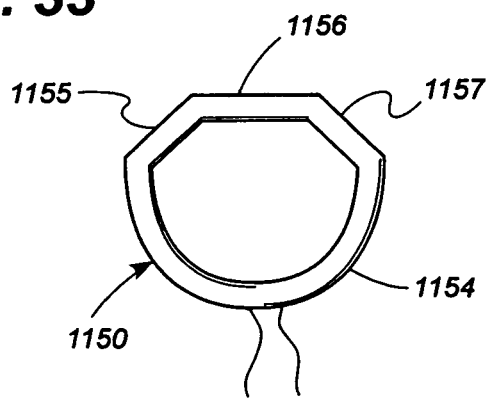
FIG. 35 is a plan view of a fourth embodiment of a drawstring implant in its normal state.
Figure 36:
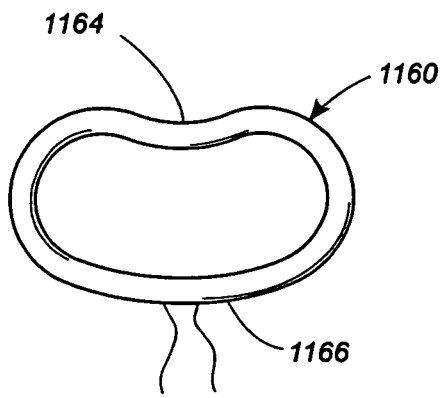
FIG. 36 is a plan view of a fifth embodiment of a drawstring implant in its normal state.
Figure 37:
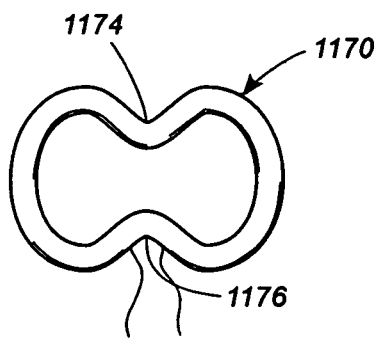
FIG. 37 is a plan view of a sixth embodiment of a drawstring implant in its normal state.
Figure 38:
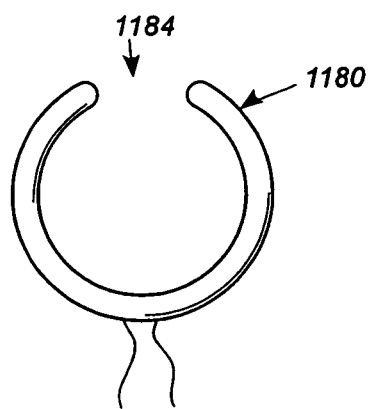
FIG. 38 is a plan view of a seventh embodiment of a drawstring implant in its normal state.
Figure 39:
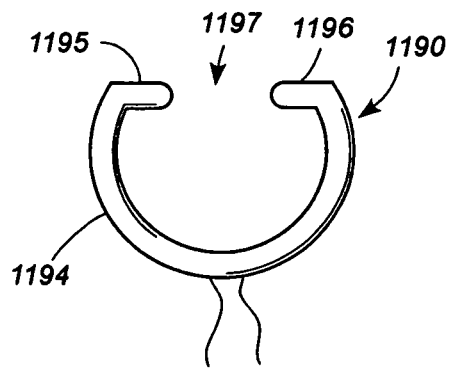
FIG. 39 is a plan view of an eighth embodiment of a drawstring implant in its normal state.
Figure 44:
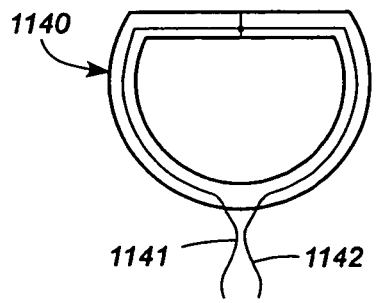
FIG. 44 is a schematic view of the drawstring implant of FIG. 34 showing the drawstring and internal attachment locations.
Figure 45:
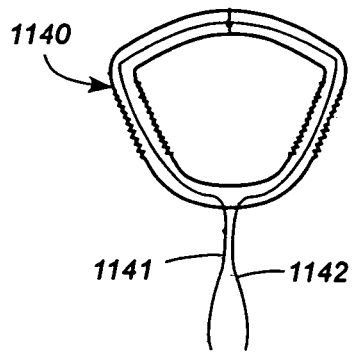
FIG. 45 is a schematic view of the drawstring implant of FIG. 44 in a cinched state.

FIGS. 31-39 illustrate various embodiments of a ring in its relaxed condition. FIG. 31 illustrates a circular ring 1110 having drawstrings 1111, 1112 extending from a lower portion thereof. FIG. 32 illustrates an oval ring 130 having drawstrings 1121, 1122. FIG. 33 depicts a hexagonal ring 1130. FIG. 34 illustrates a ring 1140 in the shape of a partial circle 1145 with a straight leg 1146 connecting the two ends of the partial circle. FIG. 35 shows a ring 1150 comprising an arcuate portion 1154 and three-straight leg portions 1155-1157 connecting the two ends of the arc. FIG. 36 shows a curvilinear ring 1160 having a convex portion 1164 on one side and a concave portion 1166 on the other. FIG. 37 depicts a curvilinear ring 1170 which is concave on both sides 1174, 1176. FIG. 38 illustrates a ring 1180 which is generally circular in shape and has an opening 1184 in its upper end. FIG. 39 shows a ring comprising an arcuate portion 1194 and straight legs 1195, 1196 extending toward one another but leaving an opening 1197 there between.

FIGS. 40 and 41 show the ring 1110 cut away to show the drawstrings 1111, 1112. The drawstrings 1111, 1112 or anchored at a location 1113 opposite the exit location 1114 of the drawstrings. When the drawstrings are tensioned, as shown in FIG. 41, the entire ring 10 is adjusted smaller.

Optionally, the drawstrings 1111, 1112 can be freely slidable within the ring 1110, rather than anchored, with largely the same effect.

In contrast to the fully adjustable ring 1110 of FIGS. 40 and 41, the ring 1110A of FIGS. 42 and 43 is only partially adjustable. The ends of the drawstrings 1111A, 1112A do not meet but rather are anchored at locations 1113A, 1113B around the ring 1110A. When the drawstrings 1111A, 1112A are tensioned, the segments 1117A, 1117B through which the drawstrings extend are the sections which are most adjusted. In contrast, the section 1118A, through which no portion of either drawstring extends, receives relatively little adjustment.

FIGS. 44-47 illustrate the effect of internal reinforcement on the adjustability of a ring. In FIGS. 1144 and 1145, a ring 1140 has no internal reinforcement. Consequently, when the drawstrings 1141, 1142 are tensioned, the entire ring 1140 adjusts. In contrast, the ring 1140A of FIGS. 46 and 47 has a reinforcing element 1144A extending through the straight leg 1146A of the ring. In the disclosed embodiment the reinforcing element 1144A is a hollow tube. However, it will be appreciated that the reinforcing element 1144A can assume other configurations, including a solid rod of suitable cross-section. Also, in the disclosed embodiment the drawstrings 1141A, 1142A are anchored to the ends of the reinforcing element 1144A. However, it will be understood that the drawstrings can extend through the tube, either to be anchored at a common location inside the tube or to be freely slidable within the tube. In the alternative, the drawstrings can extend alongside the reinforcing element 1144A, either to be anchored at a common location alongside the reinforcing element or to be freely slidable alongside the reinforcing element.

FIGS. 48-51 illustrate the use of internal shaping members operatively associated with the drawstrings such that when the drawstrings are tensioned, the shaping members cause the ring to assume a predetermined configuration. Referring first to FIGS. 48 and 49, a generally circular ring 1200 has a plurality of wedge-shaped shaping members 1201 disposed within the ring. The left drawstring 1202 is connected to the right-most shaping number 1201A, and the right drawstring 1203 is connected to the left-most shaping number 1201B when the drawstrings 1202, 1203 are tensioned, the right-most shaping member 1201 A and the left-most shaping member 1201 B are drawn toward one another. This movement of the outermost shaping members causes the wedge surfaces of each shaping number 1201 to confront the wedge surfaces of the adjacent shaping members, forcing the group of shaping members to assume the concave configuration illustrated in FIG. 49.

While the shaping members 1201 of the embodiment of FIGS. 48 and 49 are configured to assume a concave configuration when the drawstrings are cinched, it will be appreciated that the configuration of the shaping members may be designed such that the group forms a convex configuration, a straight line, a serpentine configuration with both convex and concave portions, or any other desired geometric shape.

Referring now to FIGS. 50 and 51, a generally circular ring 1210 has two groups 1212, 1213 of wedge-shaped shaping members 1211. The ring 1210 comprises four drawstrings, a pair of drawstrings being associated with each of the two groups 1212, 1213 of wedge-shaped shaping members 1211. The first drawstring 1214 extends around the ring 1210 in a clockwise direction and is connected to the uppermost member 1211A of the first group 1212 of shaping members 1211. The second drawstring 1215 extends around the ring 1210 in a counterclockwise direction and is connected to the lowermost member 1211B of the first group 1212 of shaping members 1211. Similarly, the third drawstring 1216 extends around the ring 1210 in a clockwise direction and is connected to the lowermost member 1211C of the second group 1213 of shaping members 1211, while the fourth drawstring 1217 extends around the ring in a counterclockwise direction and is connected to the uppermost member 1211D of the second group 1213 of shaping members.

When the four drawstrings 1214-1217 are cinched, the first group 1212 of shaping members 1211 is drawn together, and the second group 1213 of shaping members is drawn together. The two groups 1212, 1213 of members 1211 assume predetermined geometric shapes, causing the ring 1210 to assume the ovoid configuration shown in FIG. 51.

While the two groups of shaping members in the embodiment of FIGS. 50 and 51 form identical geometric shapes, it will be understood that the configuration of the shaping members may be designed such that each group forms a different shape. Similarly, while the two groups of shaping members in the embodiment of FIGS. 50 and 51 form convex geometric shapes, it will be appreciated that the shaping members can be configured to assume a concave shape, a straight line, or a serpentine shape comprising both convex and concave sections, or any combination of these and other shapes.

All of the devices of FIGS. 31 through 51 lie in essentially a single plane when in their relaxed state and further lie in essentially a single plane when the drawstrings are tensioned. FIGS. 52 through 55 illustrate embodiments in which internal shaping members are configured to adjust the ring to a more three-dimensional shape.

Figure 52:
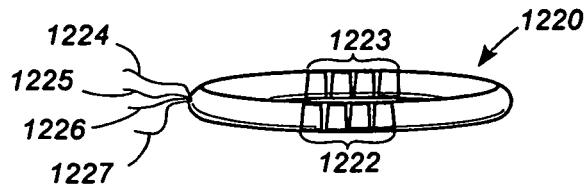
FIG. 52 is a schematic view of a third embodiment of a drawstring implant comprising internal shaping members depicting the implant in its normal state.
Figure 53:
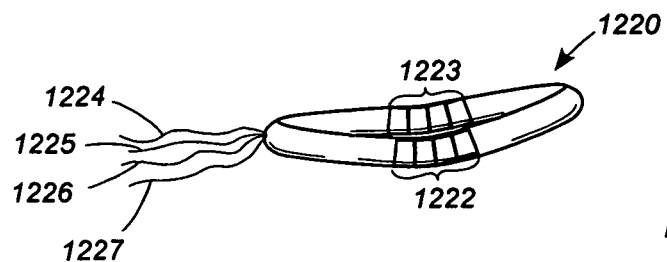
FIG. 53 is a schematic view of the drawstring implant of FIG. 52 depicting the implant in its cinched state.

Looking first at FIG. 52, a ring 1220 comprises a plurality of shaping members 1221 formed into two groups 1222, 1223. With the ring lying flat, the shaping members are narrower at the top than at the bottom. Thus, when the drawstrings 1224-1227 are cinched, the ring bows upward into the saddle-shaped configuration depicted in FIG. 53.

Figure 54:
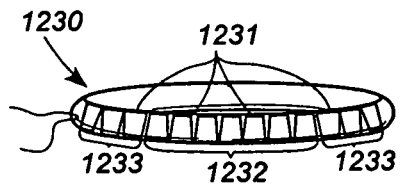
FIG. 54 is a schematic view of a fourth embodiment of a drawstring implant comprising internal shaping members depicting the implant in its normal state.
Figure 55:
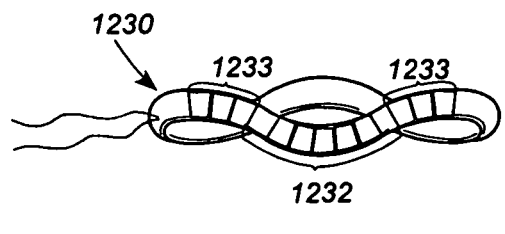
FIG. 55 is a schematic view of the drawstring implant of FIG. 54 depicting the implant in its cinched state.

FIGS. 54 and 55 illustrate an embodiment of a ring 1230 comprising a variety of differently configured shaping members 1231. Only some of the shaping members 1231 are shown in FIGS. 54 and 55 for clarity of illustration. The shaping members 1231 are arranged in alternating groups 1232 of shaping members narrower at the top than at the bottom and groups 1233 of shaping members narrower at the bottom than at the top. Utilizing the principles previously explained, it will be seen that, by having some shaping members narrower at the top that the bottom and some shaping members narrower at the bottom than at the top, complex three-dimensional configurations can be achieved.

Figure 46:
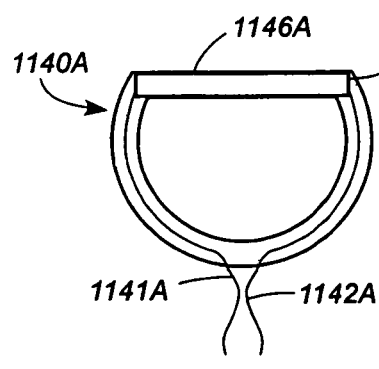
FIG. 46 is a schematic view of a variation on the drawstring implant of FIG. 34 showing the drawstring and internal attachment locations.
Figure 47:
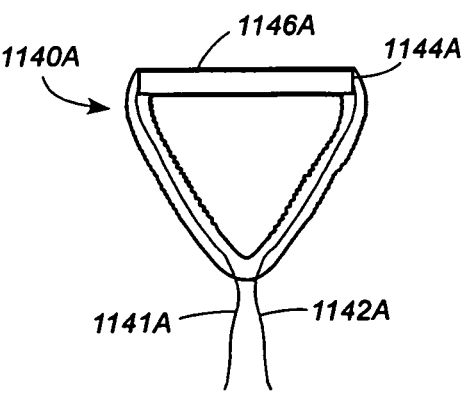
FIG. 47 is a schematic view of the drawstring implant of FIG. 46 in a cinched state.

From the foregoing examples it will be apparent that the rings can be curvilinear (FIGS. 31, 32, and 36-38), rectilinear (FIG. 33), or a combination of straight and curved segments (FIGS. 34, 35, and 39). The ring can be either entirely closed (FIGS. 31-37) or partially closed (FIGS. 38 and 39). The rings can be fully adjustable (FIGS. 40, 41, 44, and 45) or partially adjustable (FIGS. 42, 43, 46, and 47). The rings can be unreinforced (FIGS. 31-45) or reinforced (FIGS. 46 and 47). The rings can contain shaping members that assume a specific geometric configuration in two dimensions (FIGS. 48-51) or three dimensions (FIGS. 52-55).

Figure 56:
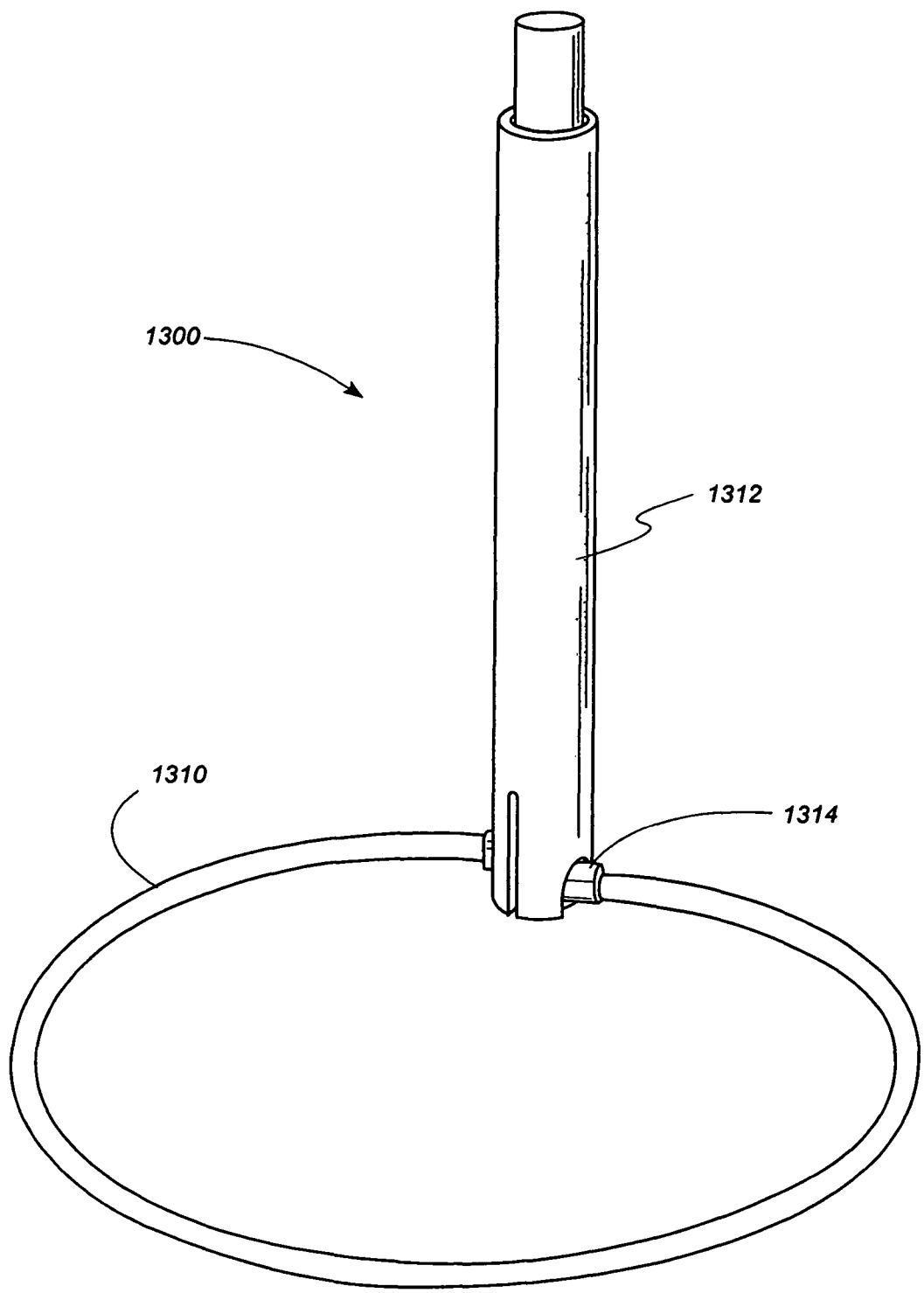
FIG. 56 is an isometric view of an implant and associated apparatus for adjusting the circumference of the implant from a remote location.

The embodiments of FIGS. 31-55 all employ drawstrings as a means for adjusting the circumference of the implants. A different approach is taken in the embodiment of FIGS. 56-70, in which an adjustable implant employs a winch to take up or to let out the circumference of the ring. Looking first at FIG. 56, a system 1300 for adjusting the configuration of a mitral valve annulus includes an adjustable ring 1310, a drive unit 1312, and a winch 1314 (largely hidden within the lower end of the drive unit 1312 in FIG. 56). Each of these components will now be discussed in more detail.

Figure 57:
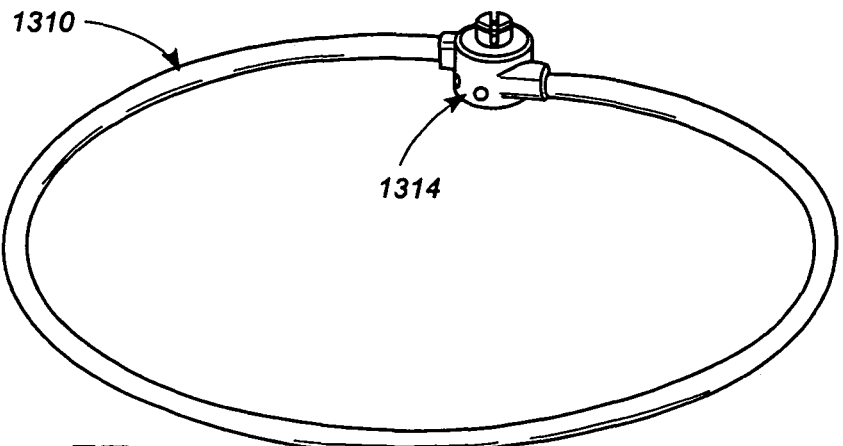
FIG. 57 is an isometric view of the implant of FIG. 56.
Figure 58:
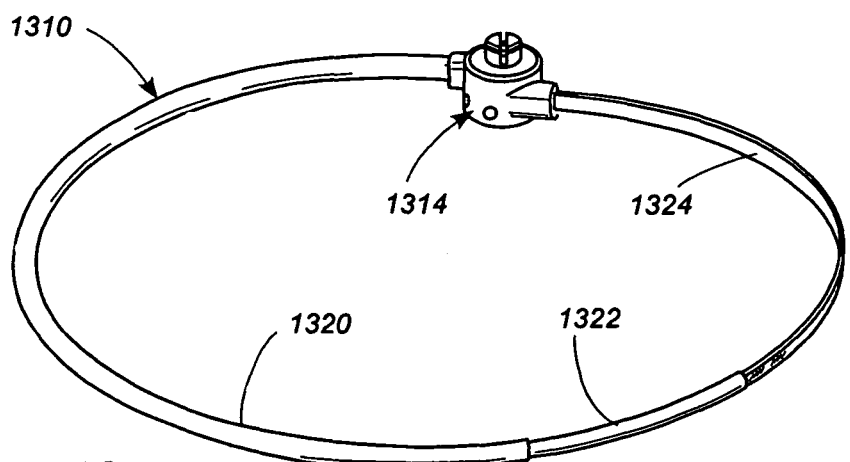
FIG. 58 is an isometric view of the implant of FIG. 56 partially cut away to reveal interior detail.
Figure 59:
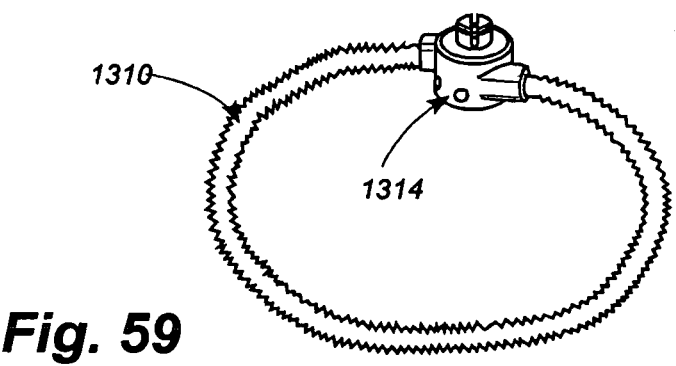
FIG. 59 is an isometric view of the implant of FIG. 56 in a cinched condition.

Referring to FIG. 57, the ring 1310 is at its maximum circumference and is coupled to the winch 1314 at each end. The ring 1310 comprises an outer layer 1320 of Dacron. In FIG. 58, the ring 1310 is cut away to reveal an intermediate layer 1322 and a band 1324 of nitinol or other suitable flexible, nonextensible material. FIG. 59 shows the ring 1310 in a contracted state.

Figure 60:
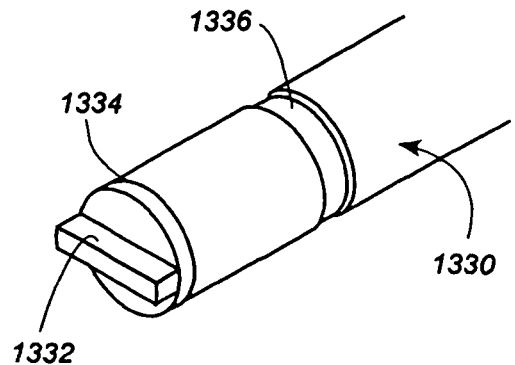
FIG. 60 is a partial isometric view of a drive shaft of the apparatus of FIG. 56 for adjusting the circumference of an implant.

FIG. 60 illustrates the distal portion of a drive shaft 1330 of the drive unit 1310. The drive shaft 1330 is of indeterminate length but is advantageously long enough to extend to a location outside the patient, while at the same time being as short as possible to facilitate transmission of torque along the length of the shaft 1330. The drive shaft 1330 is preferably a solid, flexible rod of circular cross-section, but it will be understood that other suitable shapes, including hollow tubes, or rods of cross-section other than circular, can be employed.

The drive shaft has a winch-engaging member 1332 at its distal end 1334. In the disclosed embodiment the wench-engaging member 1332 takes the form of a flat-blade screwdriver tip. However, it will be understood that other suitable tip configurations can be used to cooperatively engage the wench 1314, including, but not limited to, a Philips head tip, a hex head tip, a wrench socket, and the like. Spaced proximally up the drive shaft 1330 from the distal end 1334 is a circumferential groove 1336.

Figure 61:
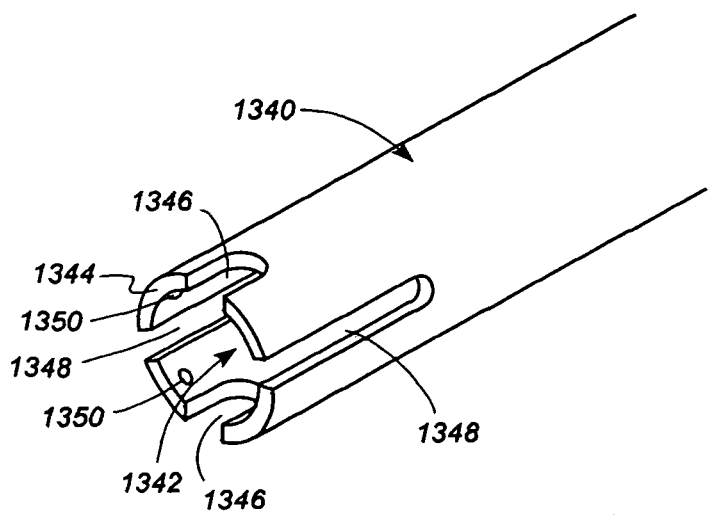
FIG. 61 is a partial isometric view of an inner tube of the apparatus of FIG. 56 for adjusting the circumference of an implant.

FIG. 61 depicts the distal portion of an inner tube 1340 of the drive unit 1310. The inner tube at 1340 is comprised of a flexible material. The inner tube 1340 has a lumen 1342 slightly larger than the outer diameter of the drive shaft 1330 such that the drive shaft can rotate freely within the inner tube 1340. At the distal end 1344 of the inner tube 1340 are a pair of openings 1346 dimensioned to clear portions of the winch 1320. Also at the distal end 1344 of the inner tube 1340 are a pair of axially-extending slots 1348, which permit the distal end 1344 of the inner tube 1340 to expand slightly.

Spaced around the periphery of the lumen, 1342 just proximal of the distal end 1344 of the inner tube 1340 are a plurality of inwardly projecting protrusions 1350. Just proximal of the proximal ends of the slots 1348 is an inwardly extending annular ring 1352 (not shown in FIG. 61; see FIGS. 69, 70).

Figure 62:
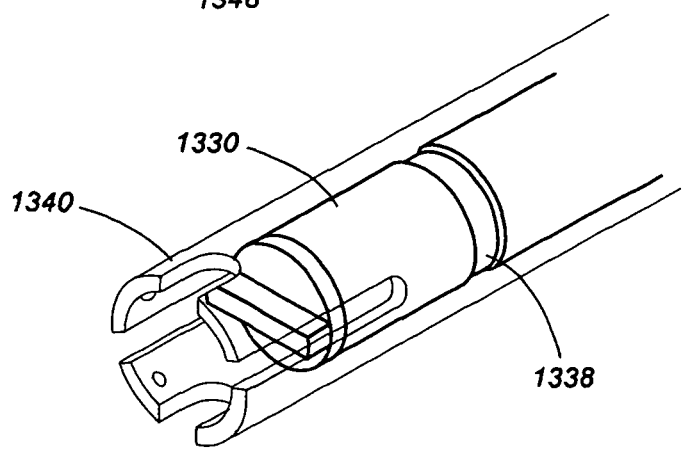
FIG. 62 is a partial isometric view of the drive shaft of FIG. 60 telescopically received within the inner tube of FIG. 61.

FIG. 62 shows the drive shaft 1330 disposed within the inner tube 1340. The distal end of the drive shaft 1330 is recessed within the distal end of the inner tube 1340. The annular ring 1352 (FIGS. 69, 70) of the inner tube 1340 engages the circumferential groove 1336 of the drive shaft 1330 to retain the drive shaft and inner tube in predetermined axial relation.

The final component of the drive unit 1310 is an outer tube 1360 (FIGS. 69, 70) of a flexible, resilient material. The outer rube 1360 has a lumen dimensioned to receive the inner tube 1340 there within, for a purpose which will be explained herein below.

FIGS. 63-65 illustrate a spindle 1370 of the winch 1320. The spindle 1370 has an upper end 1372, a lower end 1374, and a disk 1376 intermediate the upper and lower ends. The upper end 1372 of the spindle 1370 comprises a drive-shaft engagement means 1378, which in the disclosed embodiment comprises a pair of transverse slots 1380 dimensioned to receive the flat-blade screwdriver tip 1332 of the drive shaft 1330 (FIG. 60). The portions of the spindle 1370 between the slots 1380 are beveled to form facets 1382 which direct the flat-blade screwdriver tip 1332 of the drive shaft into the slots.

Below the disk is a generally cylindrically shaped body 1384. In the disclosed embodiment the cylindrical body 1384 is hollow to save material, but it will be understood that a solid cylindrical body is also suitable. At the lower end 1374 of the spindle 1370, slots 1386 are formed to extend in a generally axial direction.

The upper surface of the disk 1376 comprises a plurality of recesses 1398, the purpose of which will be explained below.

FIG. 66 shows a section of the band 1324 of the ring 1310 received within the slots 1386 and wrapped around the cylindrical body 1384 of the spindle 1370.

Figure 67:
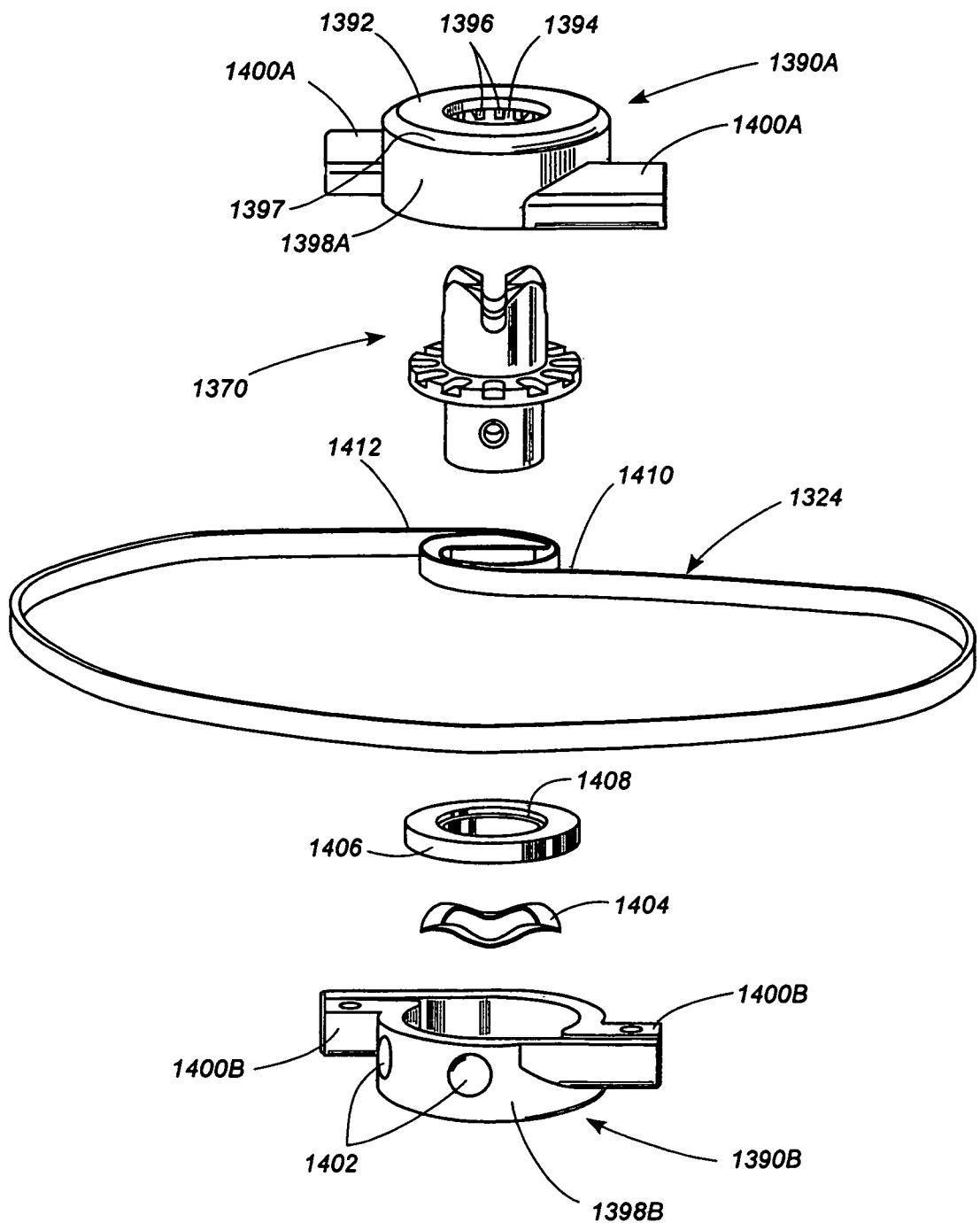
FIG. 67 is an exploded isometric view of the implant of FIG. 56.
Figure 68:
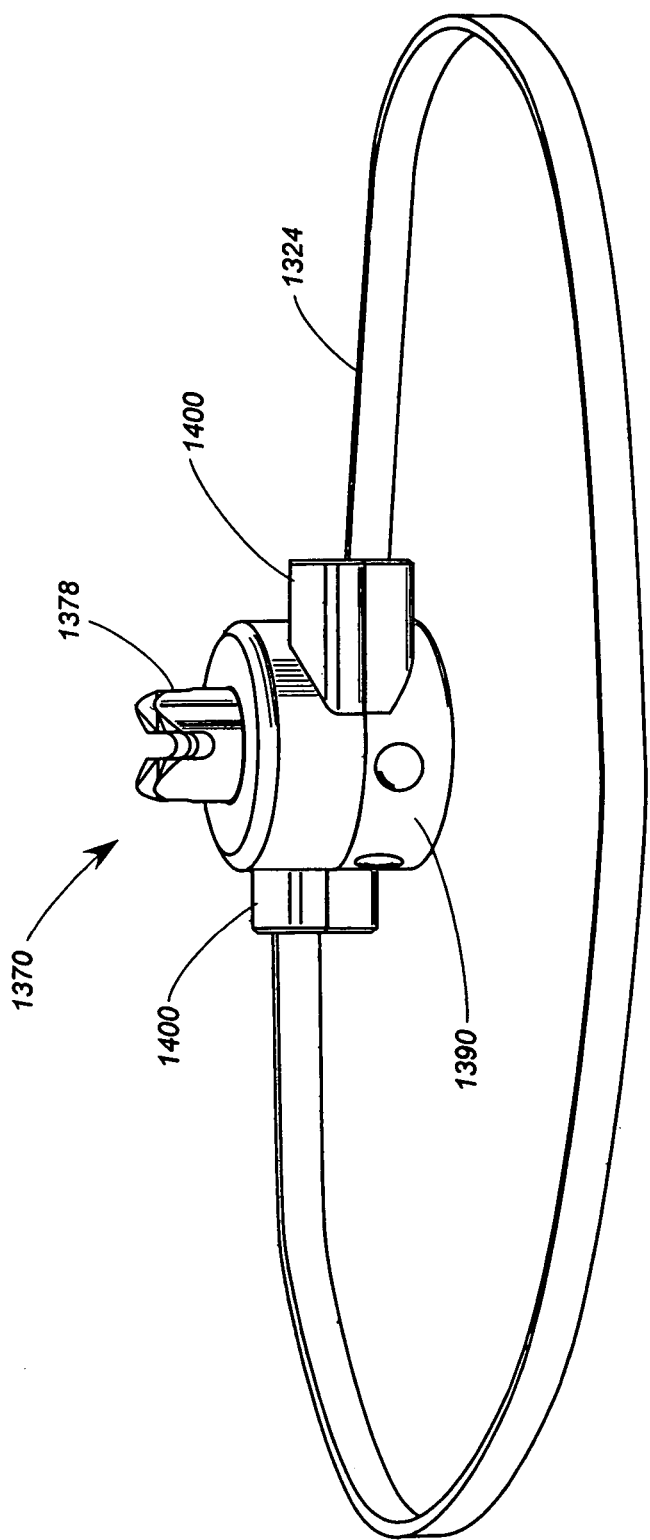
FIG. 68 is an isometric view of the winch and band of the implant of FIG. 56.

The winch 1312 will now be described with reference to FIGS. 67 and 68. The winch 1312 comprises a housing 1390 consisting of upper and lower housing halves 1390A, 1390B. The upper and lower housing halves 1390A, 1390B are preferably formed with cooperating pins and holes to facilitate in aligning and mating the housing halves. In the upper end 1392 of the upper housing half 1390A, a circular opening 1394 is formed. Surrounding the circular opening 1394 and protruding downward from the inner surface of the upper housing half 1390A are a plurality of teeth 1396. The edges 1397 of the upper surface 1392 are beveled. The upper and lower housing halves 1390A, 1390B each comprise a generally cylindrical portion 1398A, 1398B and tangentially extending sleeve portions 1400A, 1400B.

The outer periphery of the lower housing half 1390B has a plurality of dimples 1402 formed therein. Seated within the lower housing half 1390B is a wave spring 1404. A washer 1406 with an annular recess 1408 formed in its upper surface sits atop the wave spring 1404. A portion of the band 1324 of the ring 1310 is received within the slots 1386 in the lower end 1374 of the spindle 1370, and the lower end 1374 of the spindle rests within the annular recess 1408 in the upper surface of the washer 1406. Portions 1410, 1412 of the band 1324 adjacent the spindle 1370 are seated within the tangentially extending-sleeve portions 1400B of the lower housing half. The upper housing half 1390A is then assembled onto the lower housing half 1390B. As can be seen in FIG. 68, the upper end 1372 of the spindle 1370 extends through the circular opening 1394 in the upper housing half 1390A such that the drive-shaft engagement means 1378 resides outside the housing 1390. The band 1324 exits the housing 1390 through the tangentially extending sleeves 1400 such that the major portion of the band resides outside the winch housing.

Figure 69:
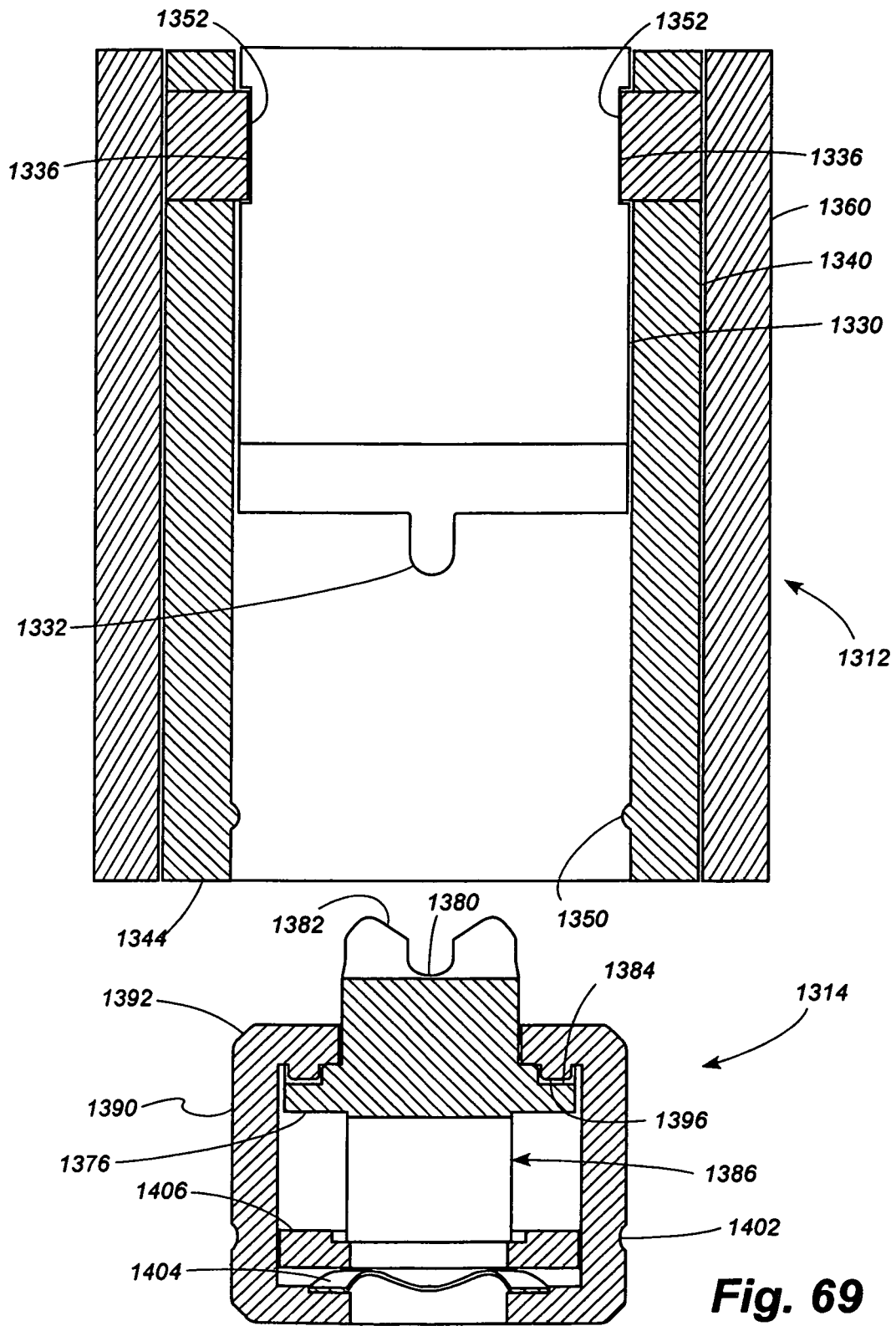
FIG. 69 is a side cut away view of the drive unit of the apparatus positioned to engage the winch of the implant of FIG. 56.
Figure 70:
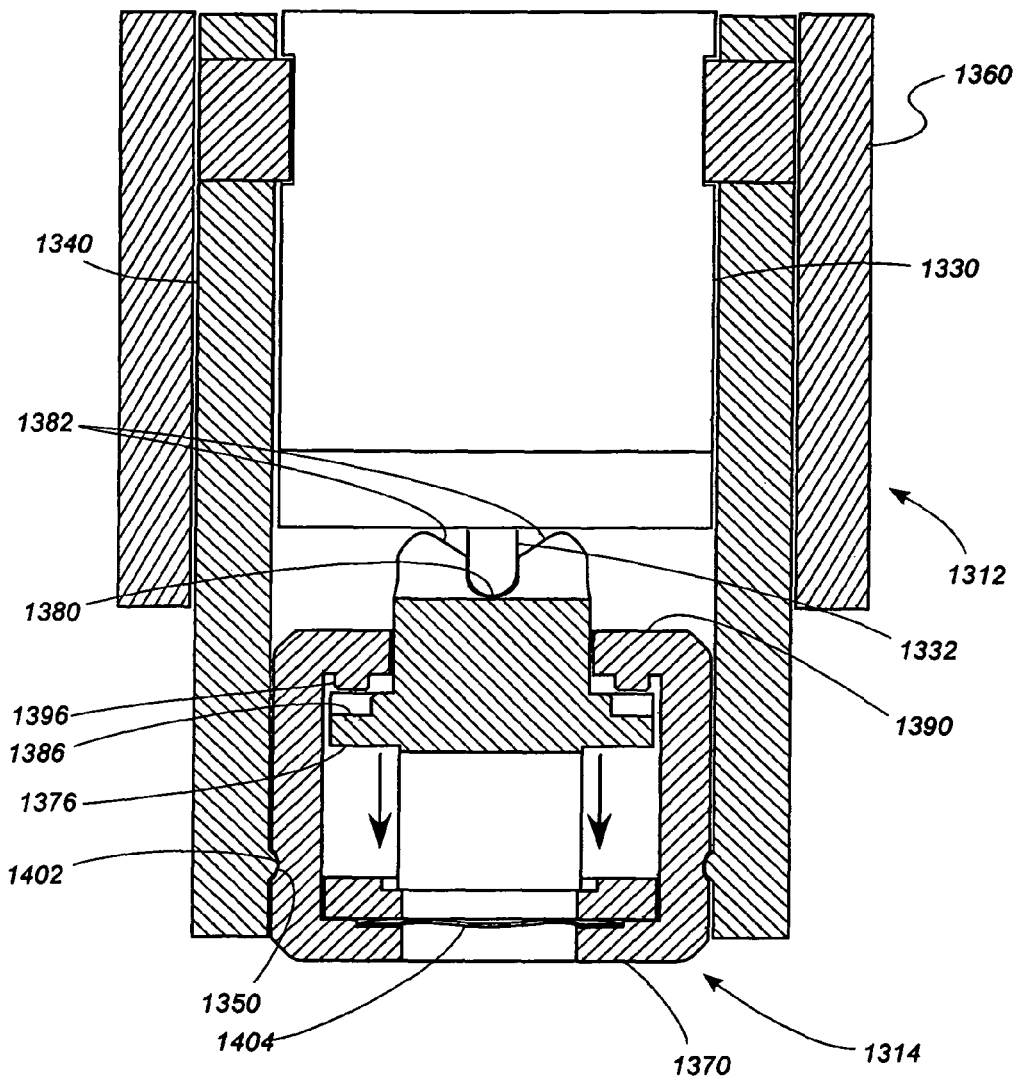
FIG. 70 is a side cut away view of the drive unit and winch FIG. 69 depicting the drive unit engaged with the winch.

FIGS. 69 and 70 illustrate the engagement of the drive unit 1312 with the winch 1314. Referring first to FIG. 69, the winch 1314 is in a self-locked state. This state is achieved by the wave spring 1404 urging the washer 1406 upward, which in turn forces the spindle 1370 upward against the top interior surface of the winch housing 1390. In this position, the teeth 1396 extending downward from the top interior surface of the housing engage the recesses 1386 in the upper surface of the disk 1376 of the spindle 1370, preventing rotation of the spindle.

As the drive unit 1312 is advanced down over the winch, the inner edges of the distal end 1344 of the inner tube 1340 confront the beveled outer edges of the upper end 1392 of the housing 1390 and spread the distal end of the inner tube. As the drive unit 1312 is advanced further, the tangential sleeves 1400 (FIG. 68) of the winch housing 1390 are received within the openings 1346 (FIG. 61) in the distal end 1344 of the inner tube 1340. Finally, the inwardly projecting protrusions 1350 within the distal end 1344 of the inner tube engage the dimples 1402 in the lower outer portion of the winch housing 1390 to lock the drive unit 1312 to the winch 1314.

Referring now to FIG. 70, as the drive unit 1312 engages the winch 1314, the blade 1332 of the drive shaft 1330 confronts the beveled facets 1382 and is directed into one of the slots 1380. As the drive unit 1312 is locked into position, the spindle 1370 is forced downward, flattening the wave spring 1404 and disengaging the recesses 1386 in the upper surface of the disk 1376 of the spindle from the teeth 1396 on the interior upper surface of the winch housing 1390. The spindle can now be turned. The band (not shown in FIGS. 69-70) wraps around the spindle 1370 as the drive shaft 1330 is turned, shortening the length of the band outside the winch housing 1390.

When the band 1370 has been adjusted to the desired length, the drive unit 1312 is disengaged from the winch 1314. The outer tube 1360 is advanced until it confronts the tangential sleeves 1400 (FIG. 68) of the winch housing 1390. The outer tube 1360 is then used to hold the winch 1314 and ring 1310 in place while the inner tube 1340 is retracted. The protrusions 1350 within the distal end 1344 of the inner tube disengage from the dimples 1,402 in the lower outer portion of the winch housing 1390. Simultaneously, the drive shaft 1330 releases its downward pressure on the spindle 1370. The wave spring 1404 returns to its normal, uncompressed condition, biasing the spindle 1370 upward so that the teeth 1396 on the interior upper surface of the winch housing 1390 once again engage the cooperating recesses 1386 in the upper surface of the disk 1376. The spindle 1370 is now prevented from rotating, thereby locking the winch 1314 and fixing the exposed length of the ring 1310.

With the mechanics of the winch 1314, ring 1310, and drive unit 1312 having thus been explained, the use of the device 1300 to reconfigure a mitral valve annulus will now be described. With the patient on bypass, the heart is opened, and the ring 1310 is sutured around the mitral valve annulus, placing stitches through the fabric outer layer 1320 and the adjacent tissue. Once the ring 1310 has been sutured in place, the drive unit 1312 is coupled to the winch 1314, and preliminary adjustment of the ring is effected. Leaving the drive unit engaged with the winch, the heart is now closed, and the patient is taken off bypass. With the heart beating, final adjustment of the ring can be effected via the drive unit, checking for reflux by suitable medical visualization means.

Once final adjustment of the ring has been achieved, the drive unit is uncoupled from the winch and removed without having to once again place the patient on bypass.

Figure 71:
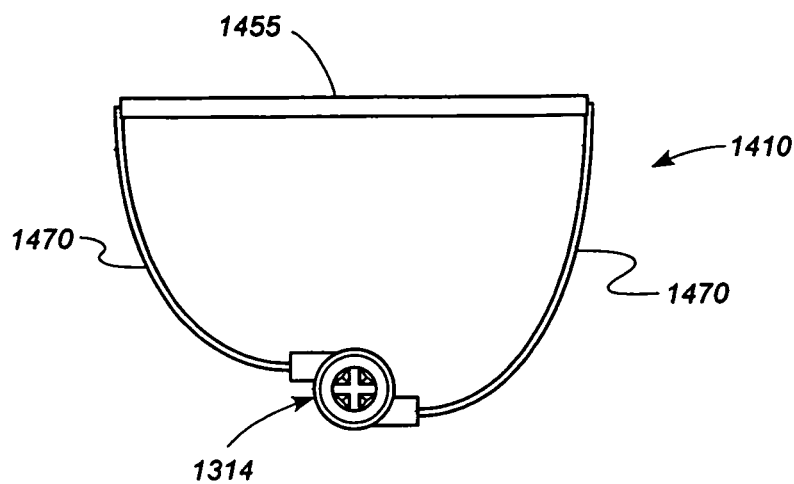
FIG. 71 is a top view of a second embodiment of a winch-adjustable implant.

FIG. 71 illustrates an alternate embodiment of a winch-adjustable ring 1410 which is D-shaped. The ring 1410 is partially adjustable and consists of a combination of straight and curved sections. In the ring 1410, a band 1470 is split, and a straight, relatively rigid section 1455 interconnects the free ends of the band. The band 1470 is wound around the winch 1314 and is taken up and let out in the same manner described above.

Figure 72:
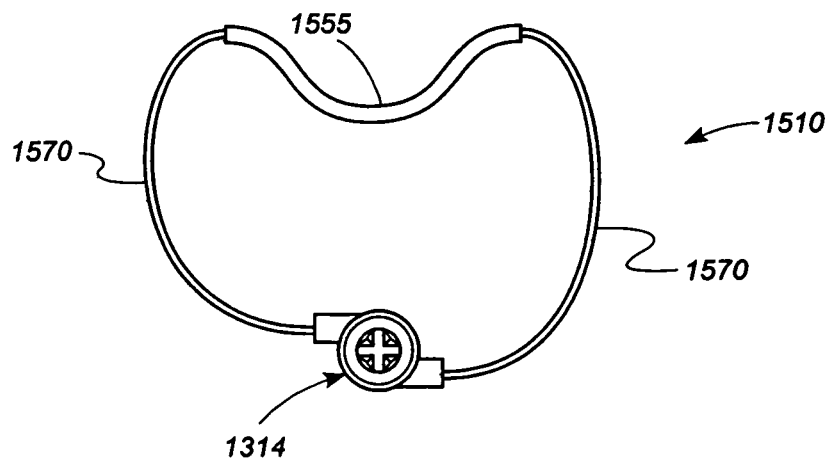
FIG. 72 is a top view of a third embodiment of a winch-adjustable implant.

FIG. 72 illustrates another alternate embodiment of a winch-adjustable ring 1510 which is partially adjustable and which is concave on one side. Again, a band 1570 is split, and a curved, relatively rigid section 1555 is connected between the free ends of the band. The band 1570 is wound around the winch 1314 and is taken up and let out in the same manner described above.

Figure 73:
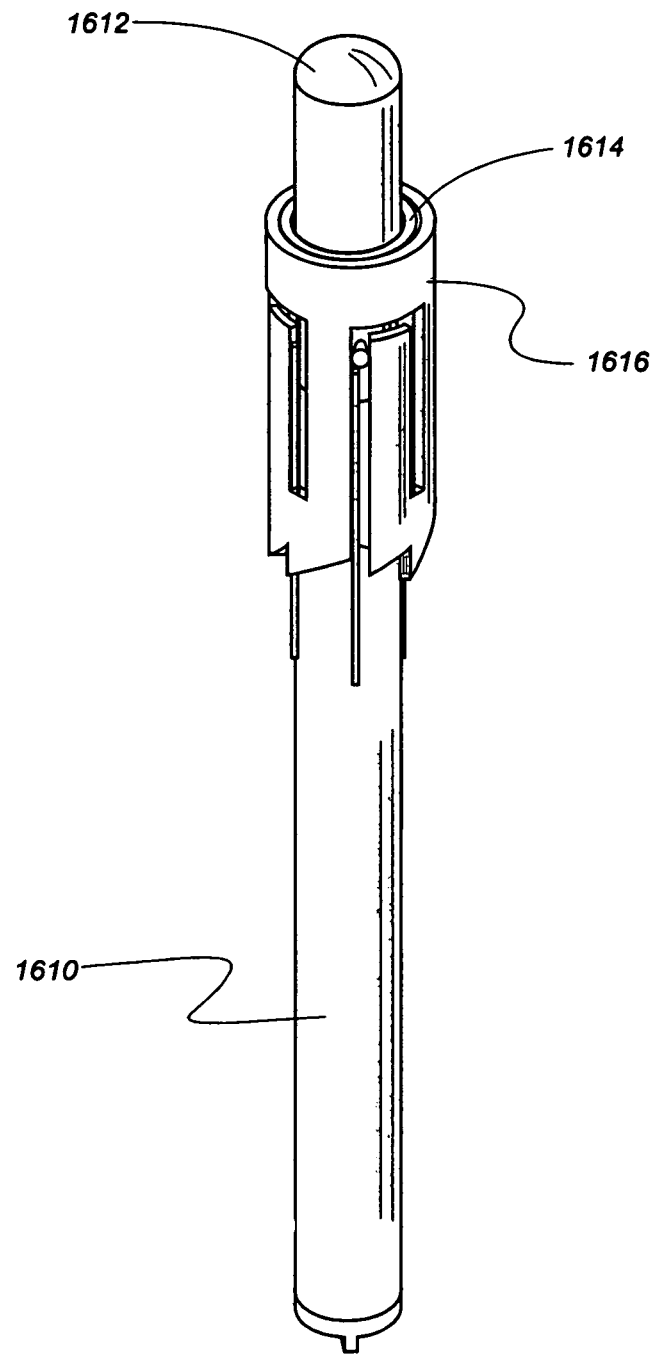
FIG. 73 is an isometric view of an alternate embodiment of a drive unit for rotating the winch on a winch-adjustable implant.

FIG. 73 illustrates a drive unit 1600 for remotely rotating the winch 1314 of the rings 1310, 1410, and 1510. Whereas the drive unit 1312 previously described transmits rotational force exerted by the user to the winch, the drive unit 1600 converts axial movement of the user into rotational movement of the winch. As shown in FIG. 43, the drive unit 1600 includes a drive shaft 1610, an actuator button 1612, an inner cam sleeve 1614, and an outer cam sleeve 616. Each of these components will now be discussed in more detail.

Referring first to FIGS. 74 and 75, the drive shaft 1610 includes an elongated shaft member 1620 having an upper end 1622 and a lower end 1624. A winch-engaging member 1626 in the form of a flat-head screwdriver blade is formed at the lower end 1624 of the shaft 1620. At the upper end 1622 of the shaft 1620 a plurality of longitudinally extending ribs 1628 are formed. In the disclosed embodiment there are four ribs 1628 spaced equidistant around the perimeter of the shaft 1620.

Referring now to FIGS. 76 and 77, the actuator button 1612 has a rounded upper end 1630 and a lower end 1632. Adjacent the lower end 1632 of the actuator button, a plurality of pins project radially outward. The pins 1634 are preferably wider at their outer ends, tapering inwardly as the pins approach the body of the actuator button 1612. In the disclosed embodiment there are four pins 1634 spaced equidistant around the periphery of the actuator button 1612.

A plurality of downwardly extending protrusions 1636 are formed on the lower end 1632 of the actuator button 1612. In the disclosed embodiment, there are eight such protrusions 1636 spaced equidistant around the perimeter of the button 1612. As can be seen in FIG. 77, the protrusions 1636 are slightly angularly offset with respect to the pins 1634.

FIGS. 78 and 79 illustrate the inner cam sleeve 1614. The inner cam sleeve 1614 has an upper end 1640, a lower end 1642, and a vertical bore 1644. The bore 1644 is dimensioned to receive the upper end of the drive shaft 1610 and the lower end of the actuator button slidably there within.

A plurality of generally vertical slots 1646 are formed in the wall of the sleeve 1614 and extend through the lower end 1642 of the sleeve. In the disclosed embodiment there are four such slots 1646 formed at 90* intervals around the sleeve. Also at the lower end 1642 of the sleeve 1614, a plurality of angled teeth 1648 are formed. In the disclosed embodiment, the teeth 1648 are generally vertical on the right side and slanted on the left side. There are eight such teeth 1648 in the disclosed embodiment, spaced equidistant around the perimeter of the sleeve 1614.

FIGS. 80 and 81 illustrate the outer cam sleeve 1616, which is similar in configuration to the inner cam sleeve 1614 except the teeth 1652 are angled in the opposite direction, that is, the left side of each tooth 1652 is generally vertical and the right side of each tooth 1652 is slanted. The bore 1654 of the outer cam sleeve 1616 is dimensioned to receive the inner cam sleeve 1614 slidably there within. The outer cam sleeve 1616 has a plurality of generally vertical slots 1656 formed in the wall of the sleeve at 90° intervals.

Figure 82:
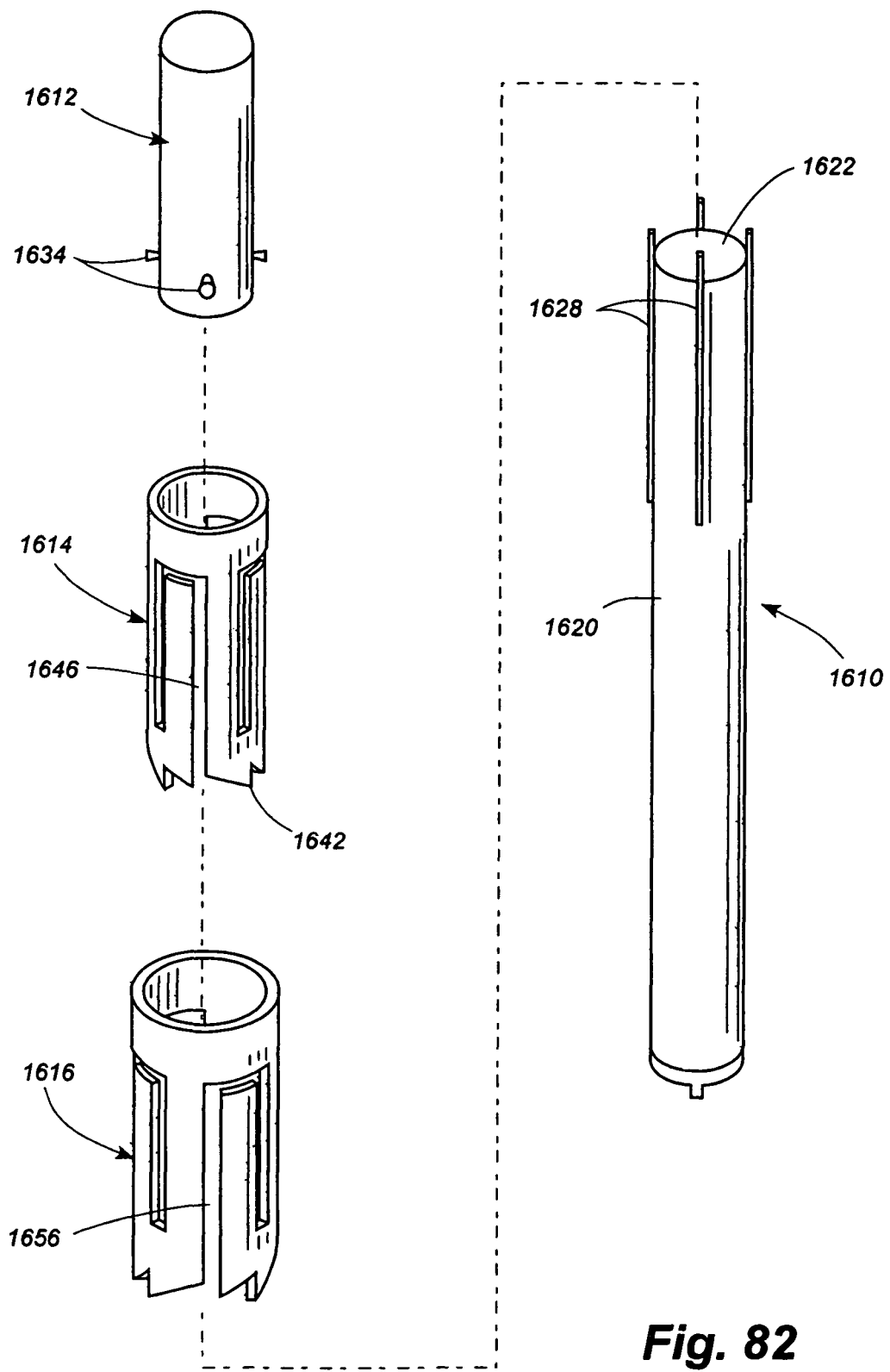
FIG. 82 is an exploded view of the drive unit of FIG. 73.

Assembly of the drive unit 1600 will now be explained with reference to the exploded view of FIG. 82. The inner and outer cam sleeves 1614, 1616 are nested and rotated relative to one another so that the vertical slots 1646, 1656 are aligned. The actuator button 1612 is then inserted into the inner cam sleeve 1614 from the lower end 1642, with the pins 1634 of the actuator button 1612 riding within the vertical slots 1646, 1656 of the inner and outer cam sleeves 1614, 1616. The upper end 1622 of the drive shaft 1610 is then inserted into the lower end 1642 of the inner cam sleeve 16142 with the ribs 1628 at the upper end 1622 of the shaft 1620 fitting within the vertical slots 1646, 1656 of the inner and outer cam sleeves 1614, 1616.

Figures 83, 84:
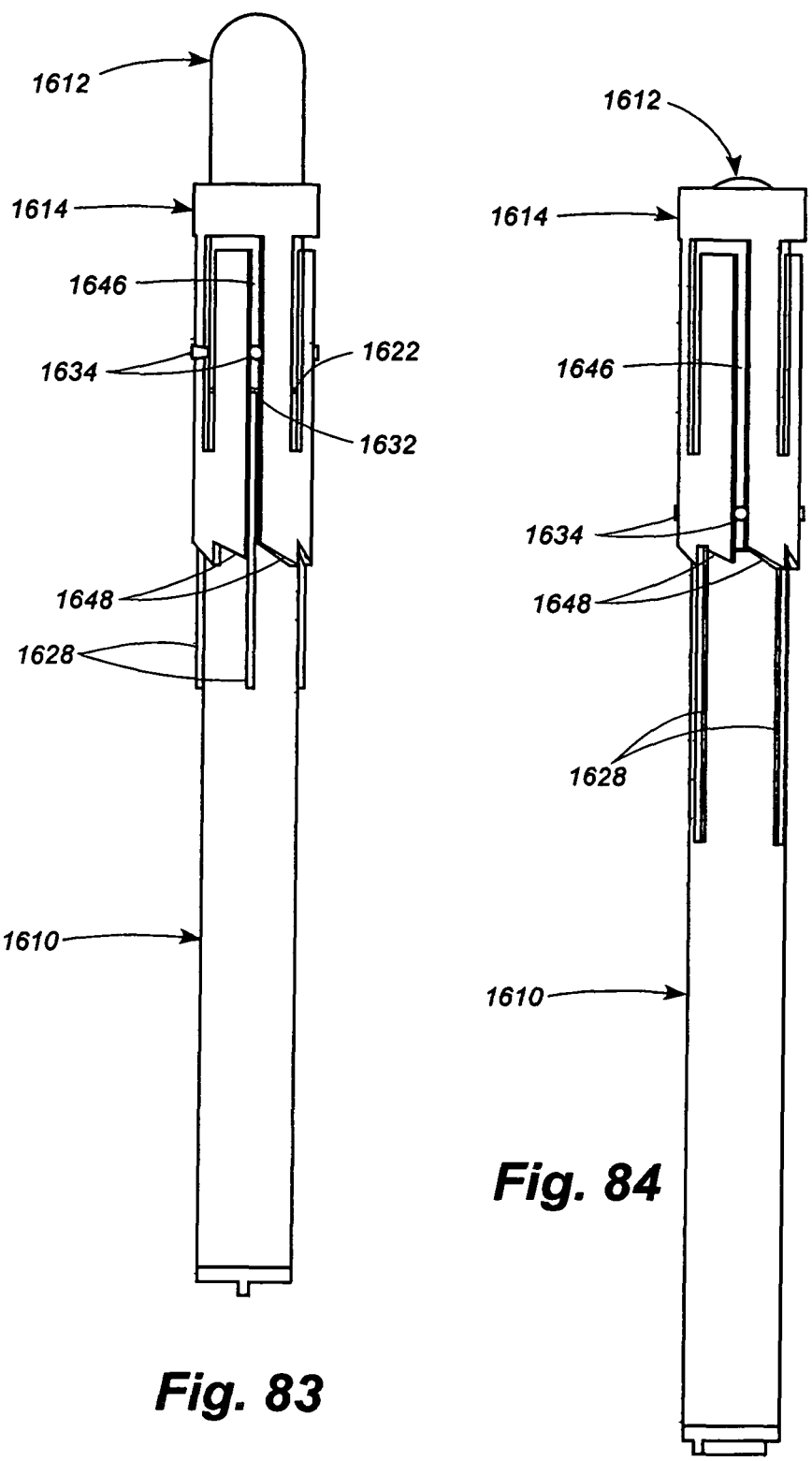
FIG. 83 is a side view of the drive unit of FIG. 73 showing the actuator button in its normal position.
FIG. 84 is a side view of the drive unit of FIG. 83 showing the actuator button in its depressed condition.

Operation of the drive unit 1600 will now be explained with reference to FIGS. 83 and 84, in which the outer cam sleeve 1616 has been removed for clarity of illustration. Referring first to FIG. 83, the actuator button 1612 is in the "up" position. The pins 1634 of the actuator button 1612 are located within the upper portions of the vertical slots 1646 of the inner cam sleeve 1614. The drive shaft is in its upper or "retracted" position, with the ribs 1628 at the upper end 1622 of the shaft 1620 fitting within the vertical slots 1646 of the inner cam sleeve 1614.

As the user presses down on the actuator button 1612, the lower end 1632 of the actuator button bears against the upper end 1622 of the drive shaft 1610, forcing it downward. The protrusions 1636 (FIGS. 76 and 77) on the lower end 1632 of the actuator button 1612 bear against the upper ends of the ribs. However, since the protrusions are angularly offset, they tend to bias the ribs toward the left (as seen in FIGS. 82 and 83). Thus, as the actuator button 1612 is depressed sufficiently for the ribs 1628 at the upper end 1622 of the shaft 1620 to clear the lower end of the slots 1646, the ribs are biased to the left. When the actuator button is released, the drive shaft 1610 is biased upward by a spring. The upper ends of the ribs 1628 engage the angled surface of the corresponding teeth 1648 and ride along the angled surface until confronting the vertical surface of the adjacent teeth.

The effect of this interaction between the ribs 1628 at the upper end of the drive shaft 1610 and the slots 1646 and teeth 1648 at the lower end of the inner cam sleeve 1614 is that the drive shaft is extended and rotated one-eight of a turn in the clockwise direction (as viewed from the upper end of the drive unit 1600). The extension of the drive shaft 1610 depresses the spindle 1370 of the winch 1314 (similar to FIG. 70), disengaging the teeth 1396 in the roof of the winch housing 1390 from the recesses 1386 in the spindle. The spindle 1370 is then rotated one-eighth of a turn in the clockwise direction, taking up the band 1324.

Subsequent depression of the actuator button 1612 moves the ribs into contact with the next adjacent teeth, rotating the spindle 1370 another one-eighth of a turn. This time, as the ribs 1628 move up the angled surface of the corresponding teeth 1648, the ribs are directed back into the slots 1646 in the 5 wall of the inner cam sleeve 1614.

To take in the band 1324, the inner cam sleeve 1614 is advanced down the shaft 1610 until the teeth 1648 in the lower end of the inner cam sleeve clear the lower end of the outer cam sleeve 1616. Thus, as the actuator button 1612 is depressed and released, the ribs 1628 interact with the lower end of the inner cam sleeve 1614. To let out the band, the outer cam sleeve 1616 is advanced with respect to the inner cam sleeve until the teeth 1652 clear the lower end of the inner cam sleeve 1614. Thus, as the actuator button 1612 is depressed and released, the ribs 1628 interact with the lower end of the outer cam sleeve 1616. Since the teeth 1652 at the lower end of the outer cam sleeve 1616 are angled in the opposite direction from the teeth 1648 at the lower end of the inner cam sleeve 1614, rotational movement of the drive shaft 1610 is reversed, and the spindle rotates in a counterclockwise direction (as seen from the top). Thus, with the lower end of the outer cam sleeve 1616 extended, the winch 1370 is loosened one-eighth of a turn for every actuation of the button 1612.

The drive unit 1600 makes possible the adjustment of an implant 1310, 1410, 1510 from a location spaced apart from the implant. This feature makes it possible to effect open-heart surgery to place the implant, close the heart, go "off pump," restart the heart, and then adjust the circumference of the implant (and thereby the mitral valve annulus) while the heart is actually beating.

While this approach presents great strides over current methods of adjusting the circumference of a mitral valve annulus, it suffers one drawback in that the patient's heart rate and blood pressure are lower as a result of the anesthesia. Thus while the implant may be adjusted so that no reflux occurs at this lower heart rate and blood pressure, it is possible that leaks may occur once the heart rate and blood pressure have returned to normal.

To overcome this drawback, it is possible to bring the patient's heart rate and blood pressure back up to normal while still in the operating room by using well-accepted drugs, for example, epinephrine. Once the patient's heart rate and blood pressure have been brought up to normal levels, the circumference of the implant can be adjusted.

Figure 85:
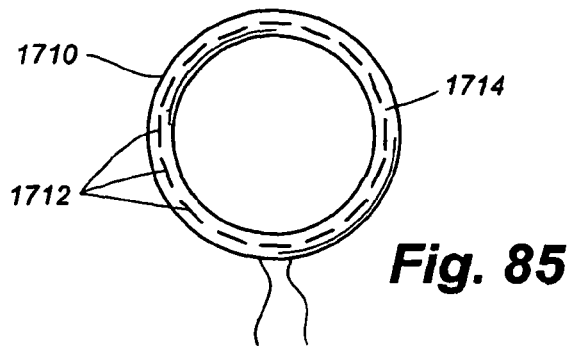
FIGS. 85-89 illustrate various embodiments of the present invention with the deployment of anchoring clips for affixing the implant to the tissue.

Referring now to FIGS. 84-88, an implant 1710 comprises deployable anchoring clips for affixing the implant to the tissue surrounding an annulus whose circumference is desired to be adjusted. The implant 1710 comprises a plurality of clips 1712 of nitinol or other resilient, shape memory material. In the case of an implant for adjusting the circumference of a mitral valve annulus, the clips may be from approximately 4 mm to approximately 10 mm in length. In their retracted state as shown in FIG. 84, the clips 1712 are straight and lie flush against (or possibly recessed within) the lower face 1714 of the implant 1710. The center of each clip 1712 is anchored to the underlying implant by stitching, adhesive, heat fusion, eyelets, by being woven into the implant, or by other suitable means. When released from their retracted state, the clips 1712 assume their normal configuration as shown in FIG. 85, that is, the free ends of the clips curve into overlapping barbs.

Figure 86:
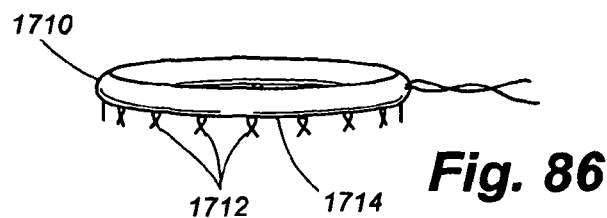
Figure 87:
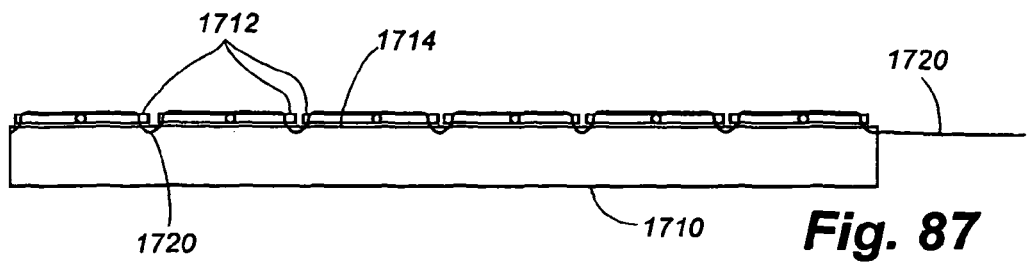
Figure 88:
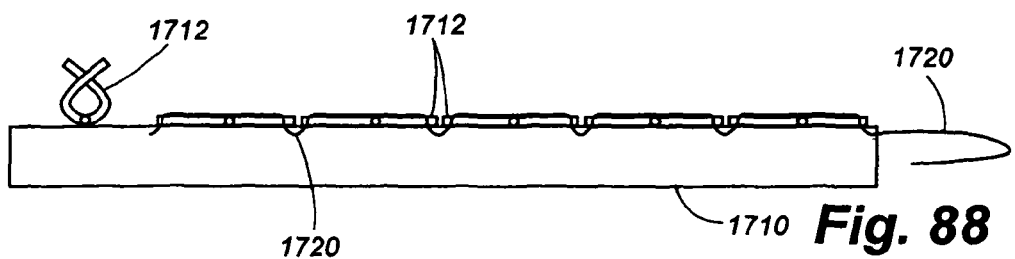

FIGS. 86-89 illustrate the deployment of the clips 1712. The clips 1712 are initially straight and lie flush against the underlying lower face 1714 of the implant 1710. Referring first to FIG. 86, a deployment suture 1720 extends upward through one free end of a first clip, along the clip, and then downward through the opposite free end of the first clip and into the underlying substrate. The suture 1720 then extends upward through the first free end of a second clip, etc., until all clips are secured to lie flush against the bottom face of the implant 1710.

Figure 89:
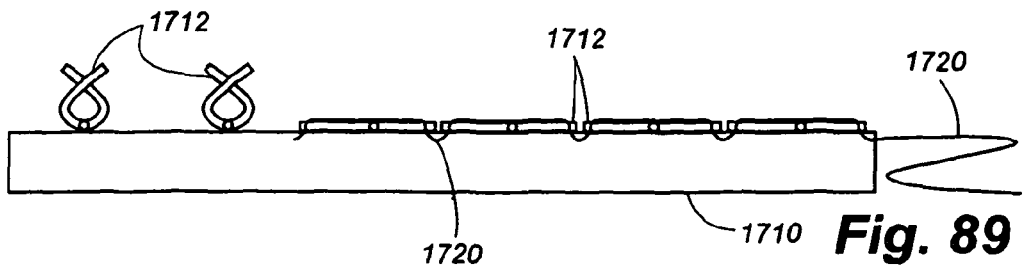

As shown in FIG. 89, to deploy the clips, the deployment suture 1720 is pulled. As the suture releases the first clip, the clip assumes its normal configuration of overlapping barbs, anchoring itself into the underlying tissue. As the suture is pulled further, the second clip is released, curling itself into overlapping barbs and anchoring itself into the underlying tissue. This procedure is continued until all clips are released and have anchored themselves into the underlying tissue.

Figure 90:
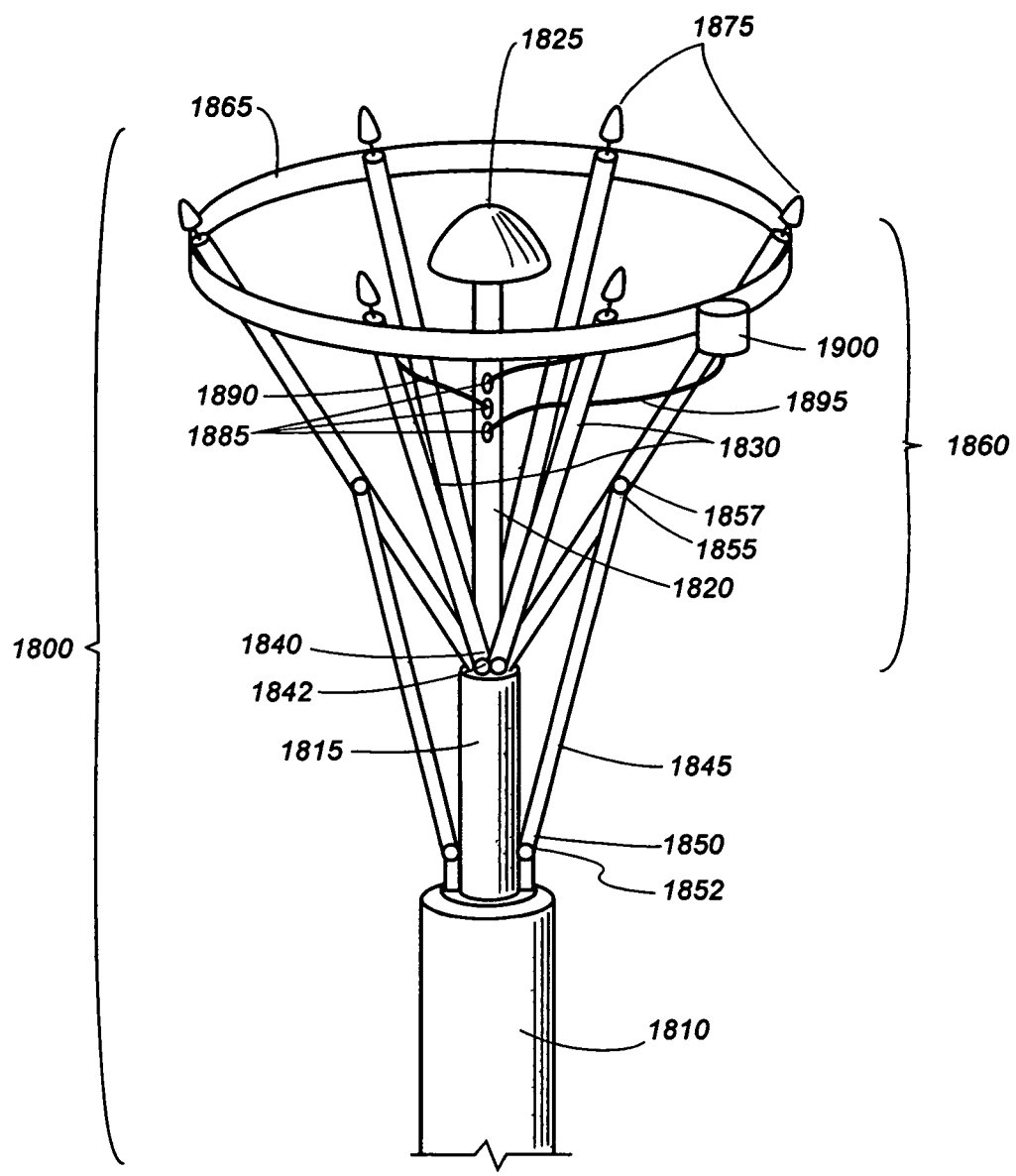
FIG. 90 is a perspective view of an alternate embodiment of an implant according to the present invention showing the implant attached to an inverted delivery umbrella protruding from a coaxial cannula.
Figure 96:
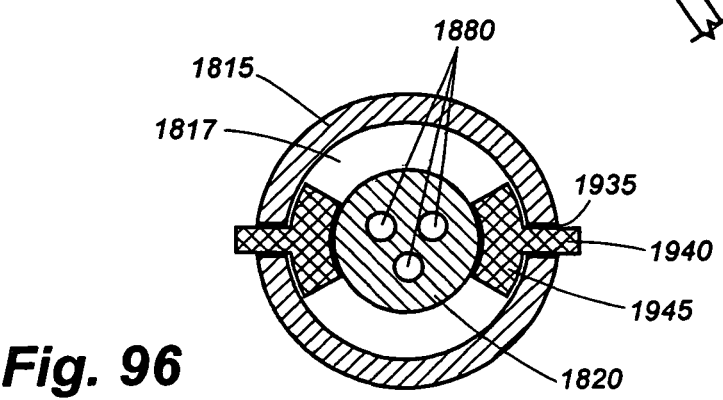
FIG. 96 is a cross sectional view of the delivery apparatus.

FIGS. 90 96 show another embodiment of a minimally invasive annuloplasty device according to the present invention, in which an implant is housed in a coaxial catheter and inserted from a minimally invasive surgical entry through the left atrium to treat a dilated and regurgitant mitral valve.

Referring now to FIG. 90, an implant/delivery system array 1800 includes a housing sheath 1810, an actuating catheter 1815 coaxially slidably disposed within the housing sheath 1810, and a core catheter 1820 coaxially slidably located within the actuating catheter 1815. The core catheter 1820 has one or more central lumens 1822 (see FIG. 96). The actuating catheter 1815 and core catheter 1820 may be separate structures as shown in FIG. 96, or in alternate embodiments, the actuating and core catheters may be a combined or continuous structure.

The implant/delivery system array 1800 includes a distal tip 1825 at the forward end of the core catheter 1820. One or more radial implant support arms 1830 have distal ends 1835 and proximal ends 1840. The proximal ends 1840 of the radial implant support arms 1830 are pivotably or bendably mounted to the core catheter 1820 at a pivot point 1842. The distal ends 1835 of the radial implant support arms 1830 normally extend along the core catheter 1820 but are capable of being displaced outward away from the core catheter.

One or more radial support struts 1845 have proximal ends 1850 pivotably or bendably mounted to the distal end of the actuating catheter 1815 at a pivotable Joint 1852. The distal end 1855 of each radial support strut 1845 is pivotably or bendably attached to a pivotable joint 1857 at a midpoint of a corresponding radial implant support arm 1830. As the actuating catheter 1815 is advanced with respect to the core catheter 1820, the radial support struts 1845 force the radial implant support an ns 1830 upward and outward in the fashion of an umbrella frame. Thus the actuating catheter 1815, core catheter 1820, radial support struts 1845, and radial support arms 1830 in combination form a deployment umbrella 1860.

A foldable or expandable prosthetic implant 1865 is releasably attached to the distal ends 1835 of the radial implant support arms 1830. One or more of the radial implant support arms 1830 comprise touchdown sensors 1875 whose distal ends extend beyond the implant 1865. Extending through one or more central lumens 1822 (see FIG. 96) of the core catheter 1820 in the exemplary embodiment 1800 and out lateral ports 1885 spaced proximally from the distal tip 1825 are one or more release elements 1890, which serve to release the implant 1865 from the delivery system, and one or more adjustment elements 1895 which serve to adjust the implant's deployed size and effect. In the exemplary embodiment in FIG. 90, the adjustment elements 1895 act on a winch system 1900 that serves to affect the circumference of the implant 1865 through mechanical action on a band or other member contained within said implant similar to those previously described herein in this disclosure. Because the release elements 1890 and adjustment elements 1895 extend through the proximal end of the core catheter 1820. as seen in FIGS. 91-93 and 99-104, these elements can be directly or indirectly instrumented or manipulated by the physician from a location outside the patient.

A delivery interface 1905 is defined in this example by the interaction of the deployment umbrella 1860, the release elements 1890, and the implant 1865. In the disclosed embodiment, the release elements 1890 may be a suture, fiber, or wire in a continuous loop that passes through laser drilled holes in the implant 1865 and in the radial implant support arms 1830, and then passes through the length of the core catheter 1820. In such an embodiment, the implant 1865 may be released from the delivery system at a desired time by severing the release element 1890 at its proximal end, outside the patient, and then withdrawing the free end of the release element 1890 through the core catheter 1820.

Figure 91:
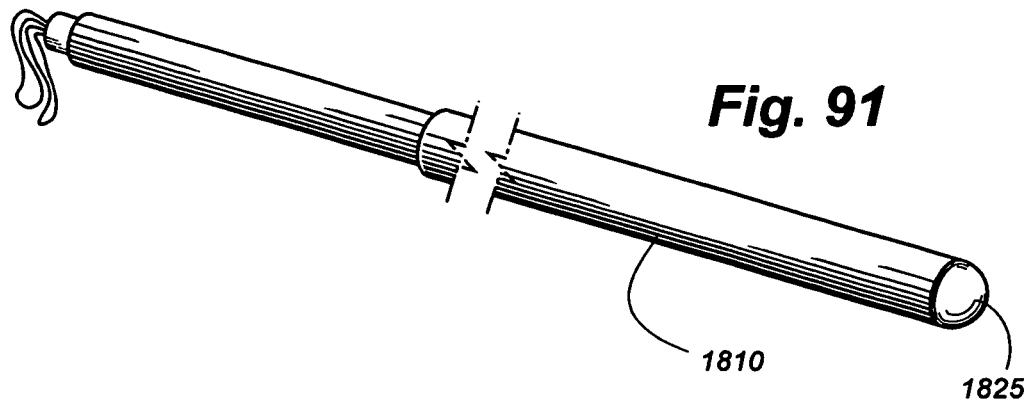
FIG. 91 is a perspective view of the implant of FIG. 90 showing the outer cannula extended to cover the implant.
Figure 92:
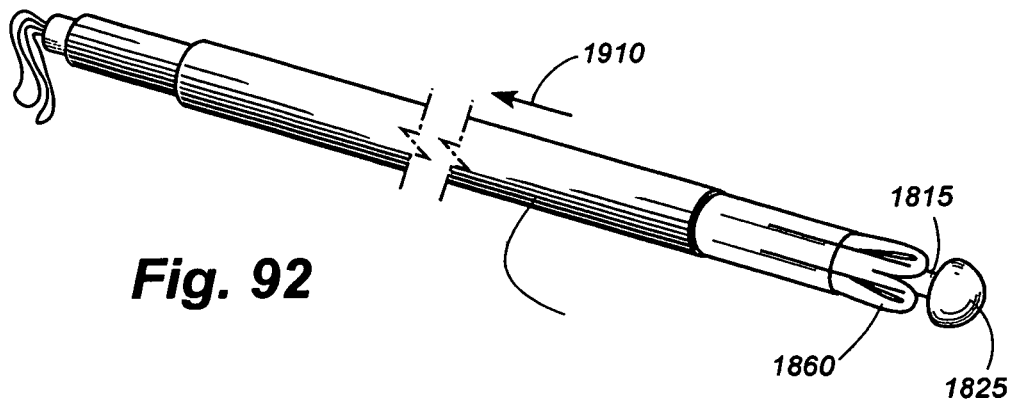
FIG. 92 is a perspective view of the implant of FIG. 90 showing the outer cannula retracted to expose the implant.
Figure 93:
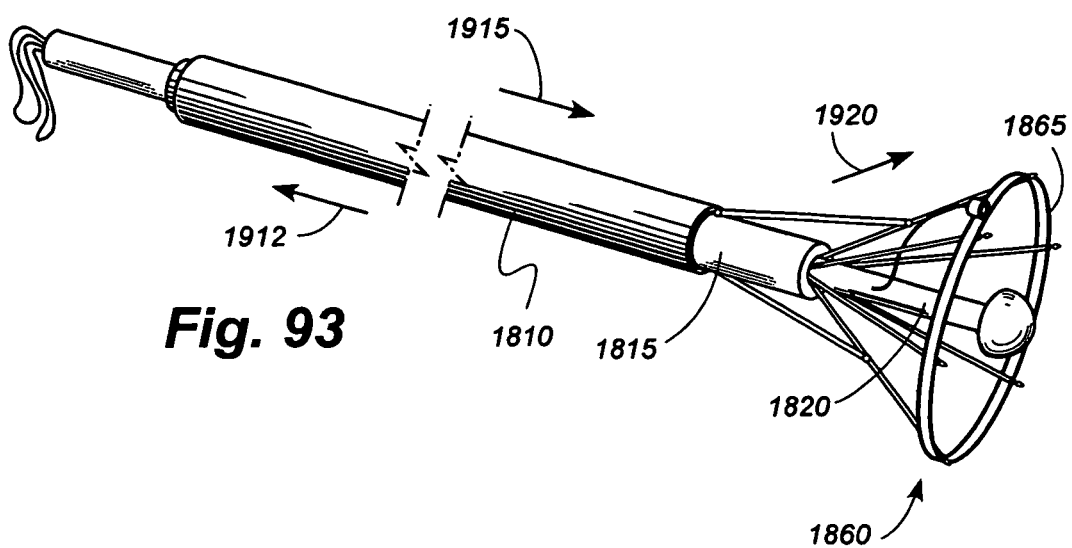
FIG. 93 is a perspective view of the implant of FIG. 90 showing the middle cannula extended to unfold the implant.

FIGS. 91 93 show the operation of the implant/delivery system array 1800, in which an umbrella like expansion of the prosthetic implant 1965 is achieved by sliding movement of the housing sheath 1810, the actuating catheter 1815, and the core catheter 1820. Referring first to FIG. 91, the housing sheath 1810 is shown in an extended position in which it covers the forward ends of the actuating catheter 1815 and core catheter 1820 for intravascular insertion of the implant/delivery system array 1800. From this starting position, the housing sheath 1810 is retracted in the direction indicated by the arrow 1910 in FIG. 92. In FIG. 93, the housing sheath 1810 has been retracted to expose the forward end of the actuating catheter 1815 and the collapsed deployment umbrella 1860. From this position the actuating catheter 1815 is advanced in the direction indicated by the arrows 1912, causing the deployment umbrella 1860 to expand in the directions indicated by the arrows 1920, After the implant 1865 has been positioned and adjusted to the proper size, the housing sheath 1810 is advanced in the direction indicated by the arrows 1915 to collapse and to cover the deployment umbrella 1860 for withdrawal of the device from the patient.

Figure 94:
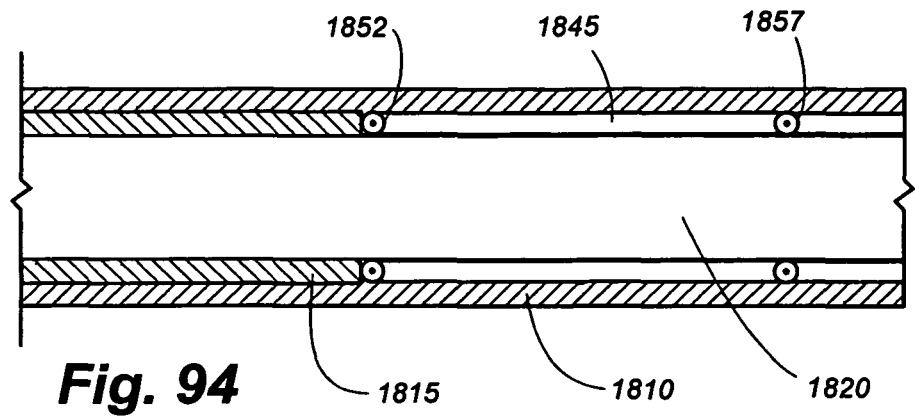
FIG. 94 is a schematic view illustrating the delivery apparatus in its closed configuration.
Figure 95:
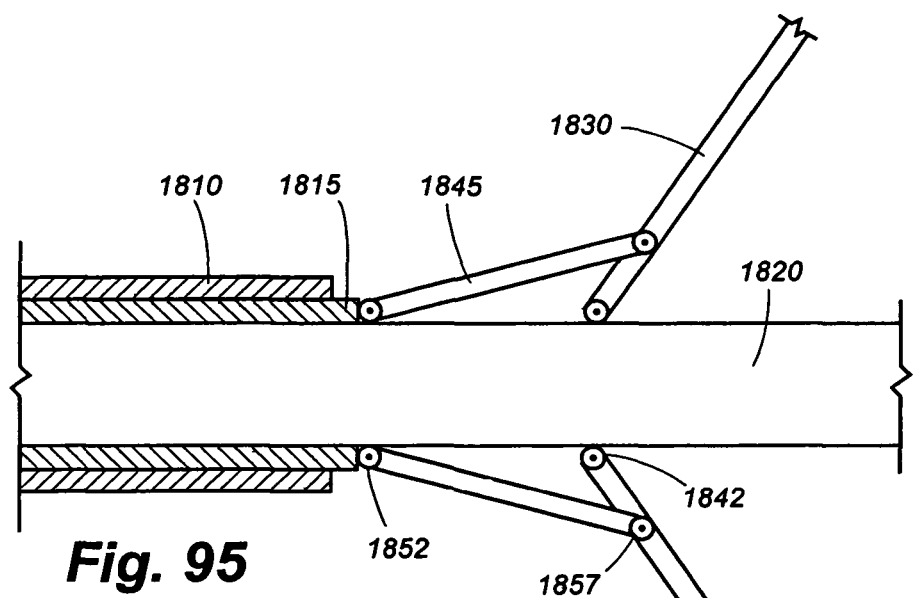
FIG. 95 is a schematic view illustrating the delivery apparatus in its open configuration.

FIGS. 94 and 95 are schematic views illustrating the radial implant support arms 1830 and the radial support struts 1845 of the implant/delivery system array 1800. FIG. 94 shows the assembly in a closed state. When the housing sheath 1810 is retracted proximally over the core catheter 1810, as shown by the arrow 1925 in FIG. 95, the radial support strut 1845 and the radial implant support arm 1830 are extended by the motion at the first pivotable joint 1852, the second pivotable joint 1857, and the third pivotable joint 1842, as shown by the arrow 1930. This motion has the effect of expanding the inverted deployment umbrella 1860 and folded implant (not shown in FIGS. 94 and 95) allowing it to achieve its greatest radial dimension, prior to engagement and implantation as previously discussed with reference to FIGS. 91-93.

FIG. 96 shows a cross section detail showing the relationship between the actuation catheter 1815 and the core catheter 1820. Attachment tabs 1940 are slidably operable within longitudinal slots 1935 in the walls of actuation catheter 1815. These attachment tabs 1940 are the site of attachment of the first pivotable joint 1852 where the radial support strut 1845 is pivotably attached at its proximal end 1850. Within the lumen 1817 of the actuation catheter 1815, slidable retention tabs 1945 serve to retain the attachment tabs 1940 in the slots 1935. The core catheter 1820 is shown to contain one or more central lumens 1880 which serve to contain release elements 1890 or adjustment elements 1895 (not shown in FIG. 96).

FIGS. 97 and 98 show further details of the touchdown sensors 1975 shown previously in FIG. 90. The touchdown sensor 1875 of FIGS. 97 and 98 includes a distal segment 1950, an intermediate segment 1960, and a proximal segment 1965. The distal segment 1950 is further provided with a distal tip 1955, which is preferably blunted in the exemplary embodiment shown, but may be provided in other configurations in alternate embodiments. The distal segment 1950 is spring mounted, so that it is capable of slidable, telescoping displacement over the intermediate segment 1960 to achieve a seamless junction with the proximal segment 1965 upon maximal displacement. When the touchdown sensor 1875 is in its normal condition, the spring extends the proximal segment such that the sensor assumes the orientation shown in FIG. 97. When the implant 1865 (FIG. 90) is seated against the periphery of an anatomical opening, the proximal segment 1965 of the sensor 1875 is compressed against the distal segment 1950, as shown in FIG. 98. The distal segment 1950 and the proximal segment 1965 may both be constructed of, are sheathed by, or otherwise covered with a radio opaque material. However, the intermediate segment 1960 is not constructed or coated with such a radio-opaque material. Therefore, when the distal segment 1950 is at rest, it is fully extended from the proximal segment 1965, and the gap represented by the exposed intermediate segment 1960 is visible on radiographic examination. However, when the distal segment 1950 is brought to maximum closeness with the proximal segment 1965, no such radio opaque gap is radiographically visible, and the touchdown sensor is said to be "activated". This embodiment allows radiographic monitoring of the position of the touchdown sensor 1875 with respect to the degree of extension of the distal catheter segment 1950. In the embodiment according to the present invention as shown, at least three or more touchdown detectors 1875 are employed to provide certain positioning against the tissue surrounding the desired anatomic opening. In various embodiments according to the present invention, activation of the touchdown sensors may also be monitored through visual sensor indicators located outside the surgical incision that may be operated by mechanical or electrical stimulation to provide an operator visual indication that each touchdown sensor has been properly activated prior to implant release.

Figure 99:
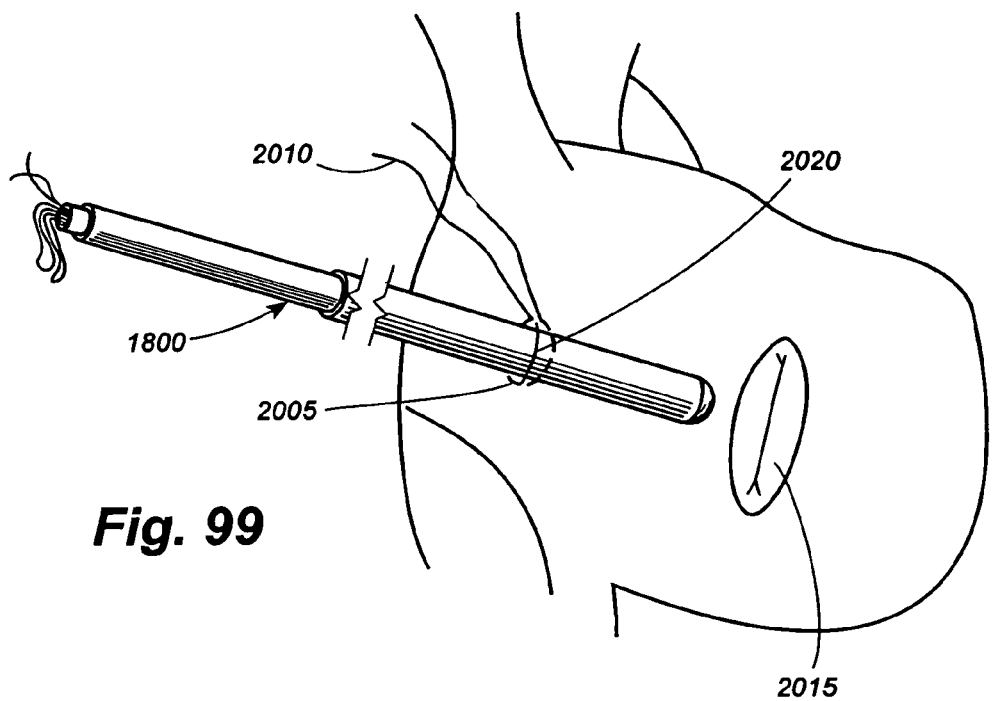
FIG. 99 is a perspective view of a procedure for the transatrial placement of the implant of FIG. 85 into the left atrium of a beating heart, where the implant is shown being introduced within a closed coaxial cannula placed through an incision or trocar wound controlled by a purse string suture.

Referring now to FIGS. 99-104, an exemplary surgical procedure is shown using an embodiment according to the present invention. In this example, a small thoracotomy has been performed by a surgeon, and the anterior wall of the left atrium of a patient's beating heart has been exposed. FIG. 99 shows a purse string suture 2005 which has been placed in the wall of the left atrium to effect a Rommel tourniquet 2010. A blade or sharp trocar (not shown) has been used to create an entry wound 2020 into the left atrium. An implant/delivery system array 1800 according to the present invention is introduced through the entry wound 2020 into the left atrium, directly over the mitral valve opening 2015, and the Rommel tourniquet 2010 is secured for homeostasis.

Figure 100:
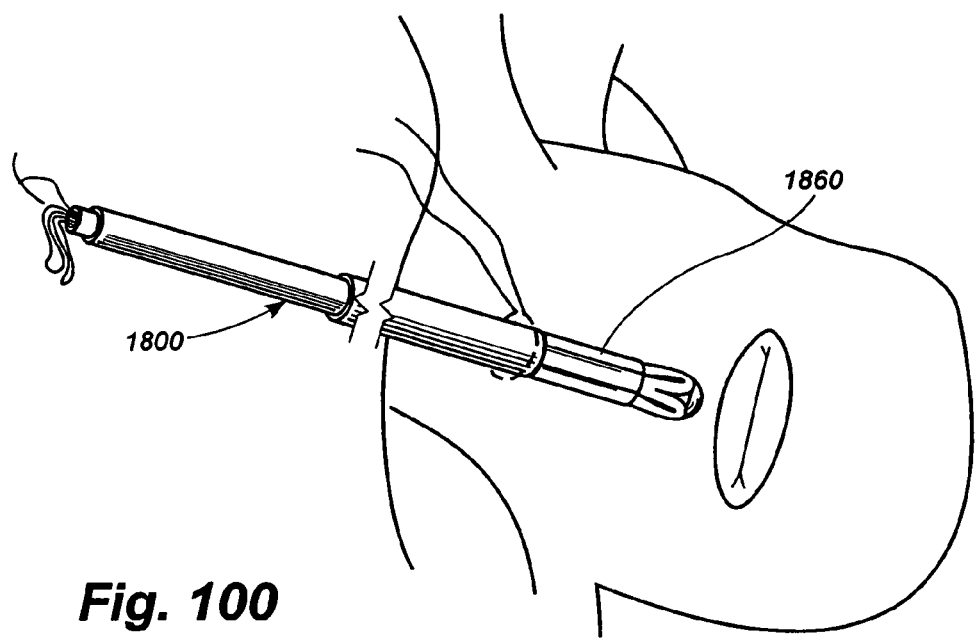
FIG. 100 is a perspective view of a subsequent step of the procedure of FIG. 99, where the outer cannula covering the implant is shown being retracted to partially expose the folded implant.

As shown in FIG. 100, the housing sheath is then retracted, exposing the deployment umbrella 1860 and attached folded implant.

Figure 101:
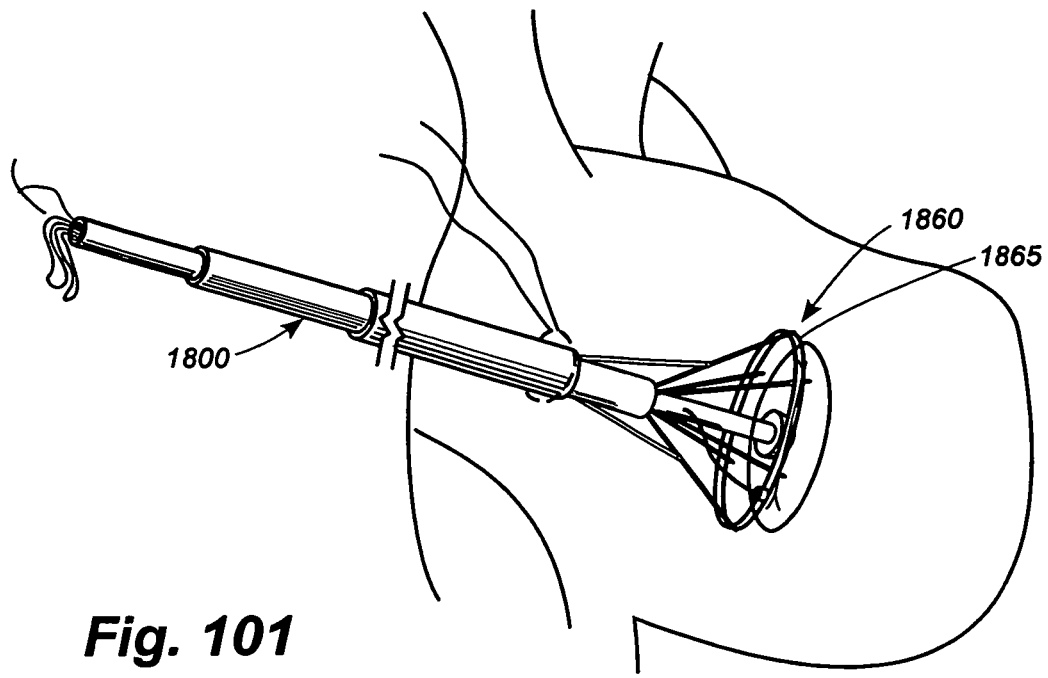
FIG. 101 is a perspective view of a subsequent step of the procedure of FIG. 99, where the outer cannula is shown in a fully retracted position and with extension of the inverted delivery umbrella, fully unfolding the implant, and with touchdown sensors in an undepressed state.
Figure 102:
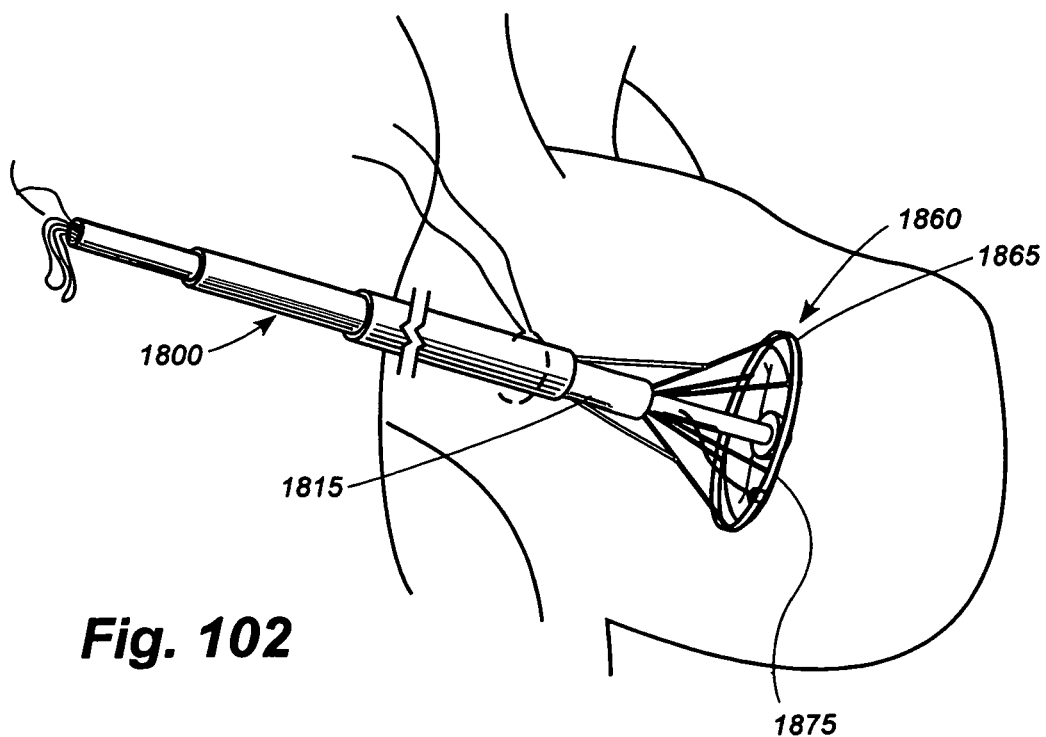
FIG. 102 is a perspective view of a subsequent step of the procedure of FIG. 99, where the outer cannula is shown in a fully retracted position and with extension of the inverted delivery umbrella, fully unfolding the implant, and with all touchdown sensors in an compressed state, indicating placement over the mitral annulus.

Referring now to FIG. 101, the activation catheter 1815 has been advanced, expanding the deployment umbrella 1860 and unfolding the implant 1865. The implant/delivery system array 1800 is then advanced under transesophageal echo, fluoroscopy, cardiac ultrasound, or other real time visualization techniques, and/or using visual sensor indicators as previously described until at least three touchdown sensors 1875 are confirmed to be activated, as shown in FIG. 102.

Figure 103:
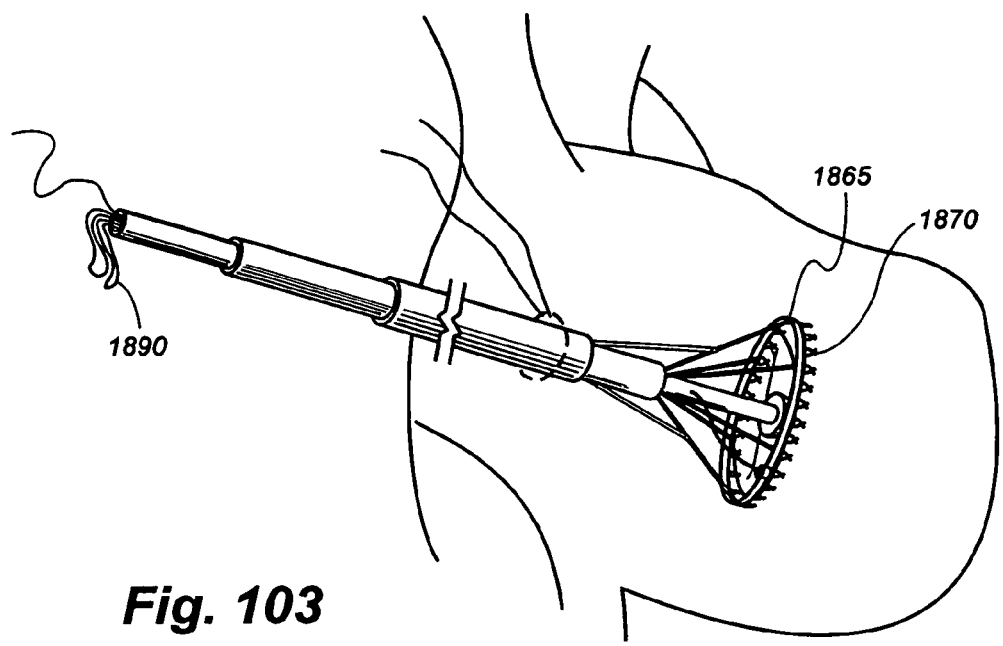
FIG. 103 is a perspective view of a subsequent step of the procedure of FIG. 99, where a control suture has been cut and withdrawn from the implant, causing deployment of the anchoring clips therein within the anryulus of the valve.

Referring now to FIG. 103, within the prosthetic implant 1865 and extending proximally there from when released are a plurality of tensioned attachment clips 1870. In the exemplary implant/delivery system array 1800 shown in FIG. 104, the suture loop that serves as the release element 1890 for the tensioned attachment clips 1870 in the implant 1865 is cut and removed by the operator, releasing the tensioned attachment clips 1870 which extend upon their release and engage the desired tissue on contact.

Figure 104:
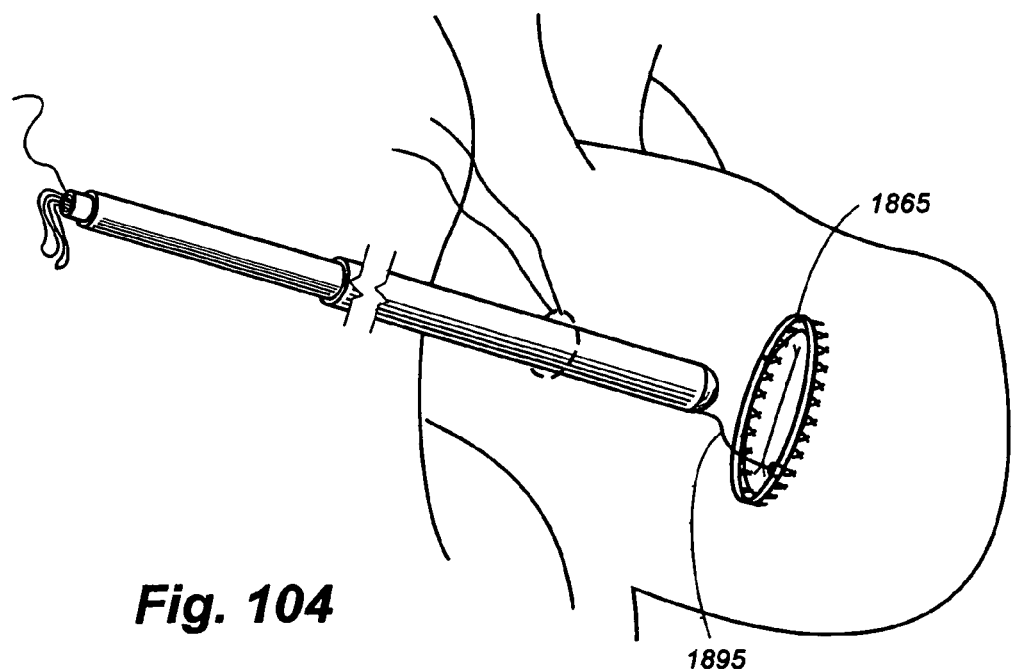
FIG. 104 is a perspective view of a subsequent step of the procedure of FIG. 99, where the inverted delivery umbrella has been detached from the implant and is retracted into the outer cannula for removal from the heart.

FIG. 104 shows the similar cut and release of the release element 1890 for detaching the deployment umbrella 1860 from the implant 1865 after implantation, and extension of the housing sheath 1810 to collapse the deployment umbrella (no longer visible in FIG. 104), leaving the adjustment element 1895 attached to the implant 1865.

Figure 105:
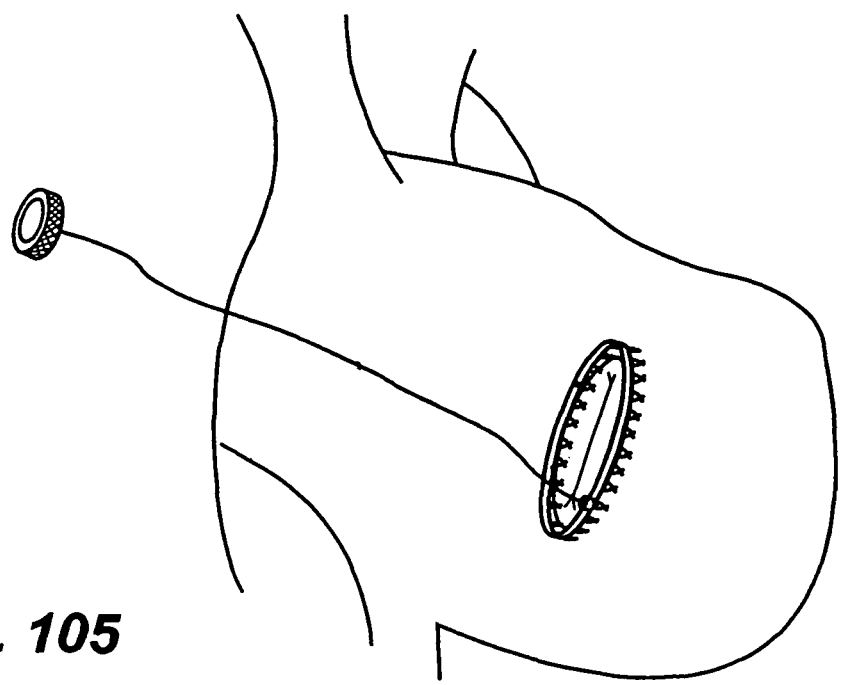
FIG. 105 is a perspective view of a subsequent step of the procedure of FIG. 99, where the inverted delivery umbrella has been removed from the heart, leaving an adjustment element for adjustment of the implant's size and effect.
Figure 106:
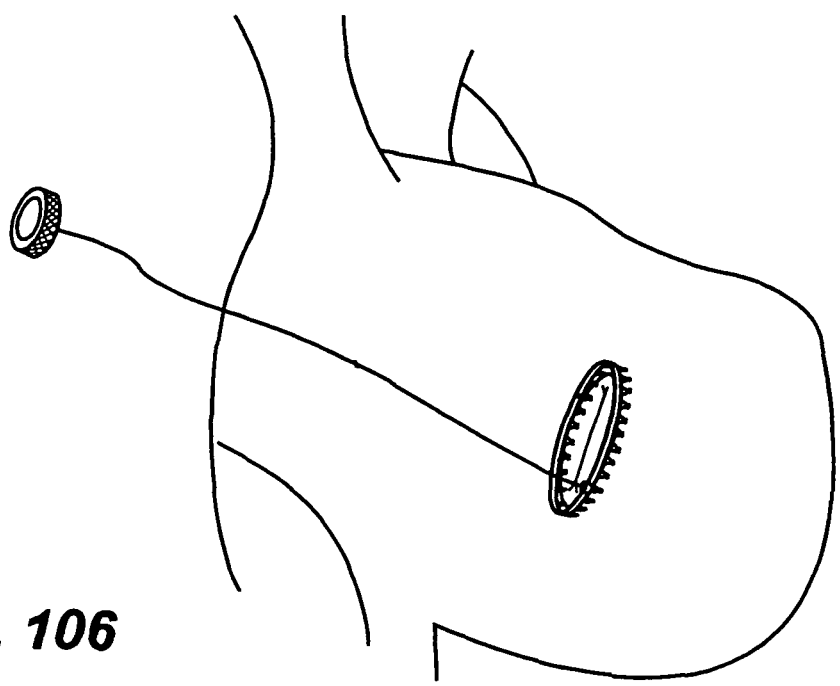
FIG. 106 is a perspective view of a subsequent step of the procedure of FIG. 99, where adjustment of the implant's size and physiologic effect has been accomplished, and the remaining adjustment element is ready to be removed.

Referring now to FIG. 105, using trans esophageal echo or other diagnostic techniques capable of quantitatively monitoring valvular regurgitation or insufficiency, an operator may adjust the circumference of the implanted implant 1865 using the adjustment element 1895, after the implant/delivery system array 1800 has been removed from the operative field. When optimal correction of the regurgitant valve has been achieved, as shown in FIG. 106, the adjustment element 1895 may be removed from the field, and the purse string suture 2005 closed for final homeostasis.

Figure 107:
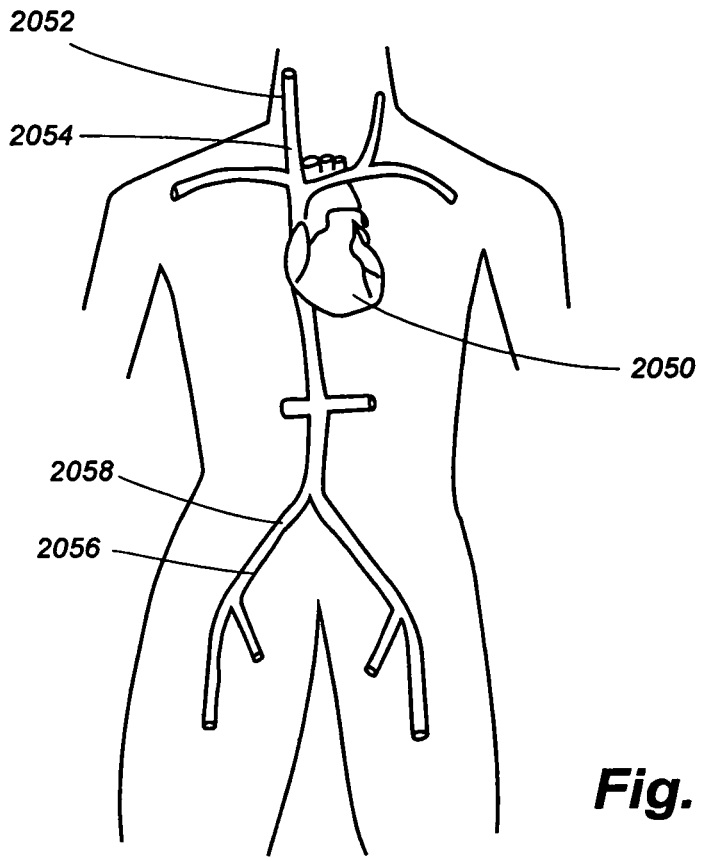
FIG. 107 is a schematic view of an alternate embodiment of a delivery apparatus.
Figure 108:
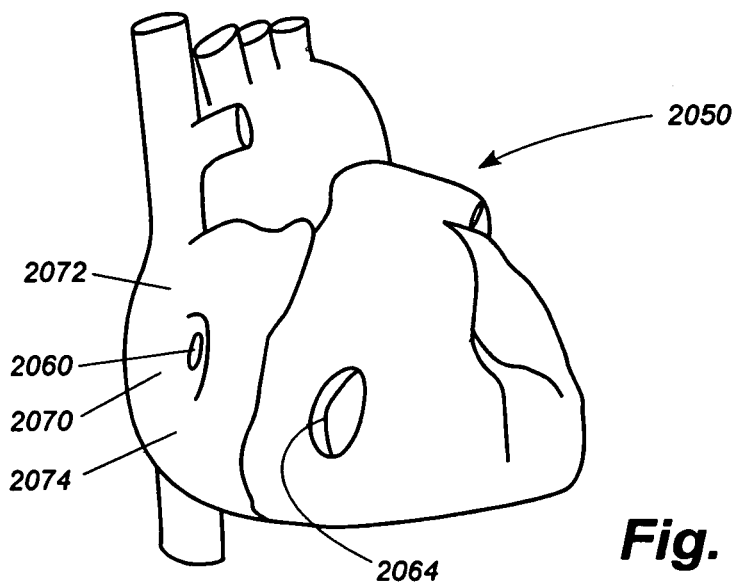
FIG. 108 is a schematic view of a portion of the vascular system of a human body showing two possible entry points for percutaneous implantation of an apparatus for treating mitral valve regurgitation.

The implant delivery systems 1800, 2000 can also be employed to position an implant percutaneously. FIG. 107 shows two prospective entry locations for percutaneous access to the heart 2050, the first 2052 in the right internal jugular vein 2054, and the second 2056 in the right femoral vein 2058. FIG. 108 shows the heart 2050 with an opening 2060 formed by the surgeon in the atrial septum. The mitral annulus is shown at 2064, the right atrium is shown at 2070, the superior vena cava at 2072, and the inferior vena cava at 2074.

Figure 109:
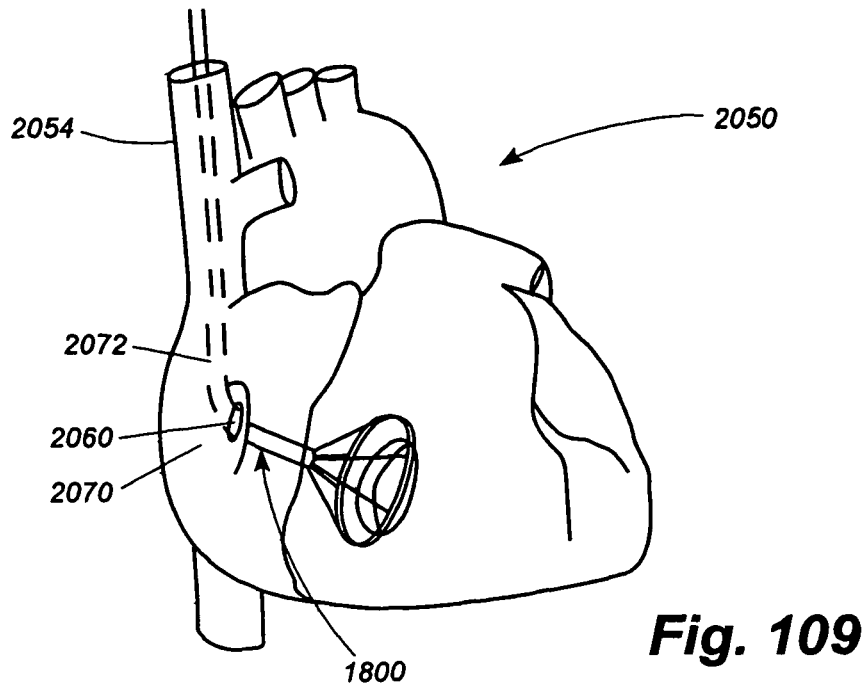
FIG. 109 is a schematic view of the human heart showing the mitral annulus and an entry wound in the left atrium.

In the percutaneous procedure shown in FIG. 109, the implant delivery system 1800 has been introduced through the right internal jugular vein access point 2052 (FIG. 107) and advanced through the right internal jugular vein 2054 to the heart 2050. The implant delivery system 1800 enters the right atrium 2070 via the superior vena cava 2072. The system then traverses the atrial septum through the opening 2060.

Figure 110:
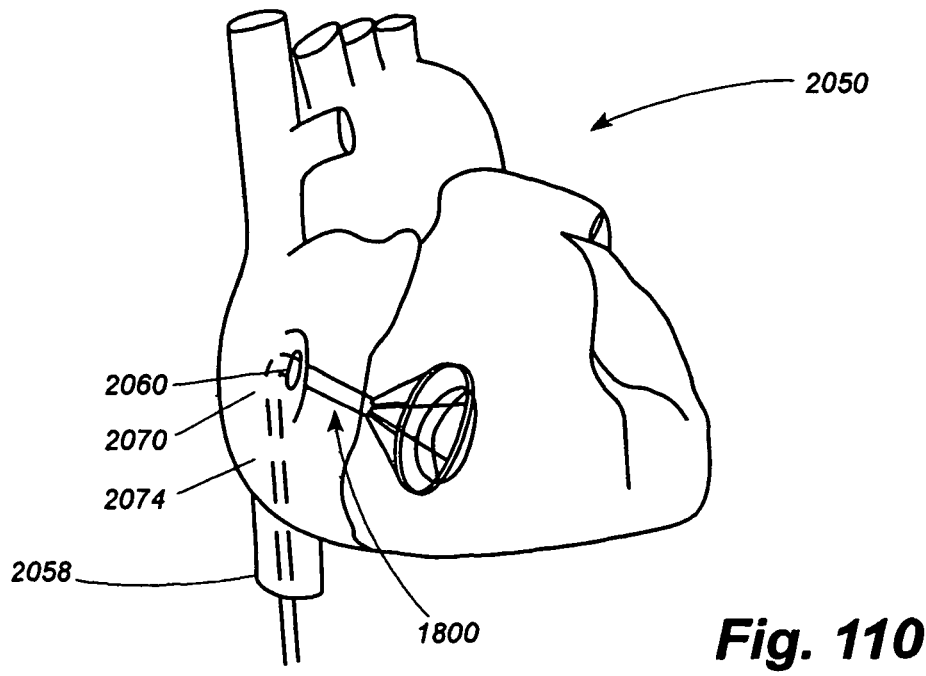
FIG. 110 is a schematic view of the heart of FIG. 109 showing a delivery device entering the heart through the right internal jugular vein traversing the left atrium through the entry wound, and positioning the implant around the mitral annulus.

In the percutaneous procedure shown in FIG. 110, the implant delivery system 1800 has been introduced through the right femoral vein access point 2056 (FIG. 107) and advanced through the right femoral vein 2058 to the heart 2050. The implant delivery system 1800 enters the right atrium 2070 via the inferior vena cava 2074. The system then traverses the atria] septum through the opening 2060.

Figure 111:
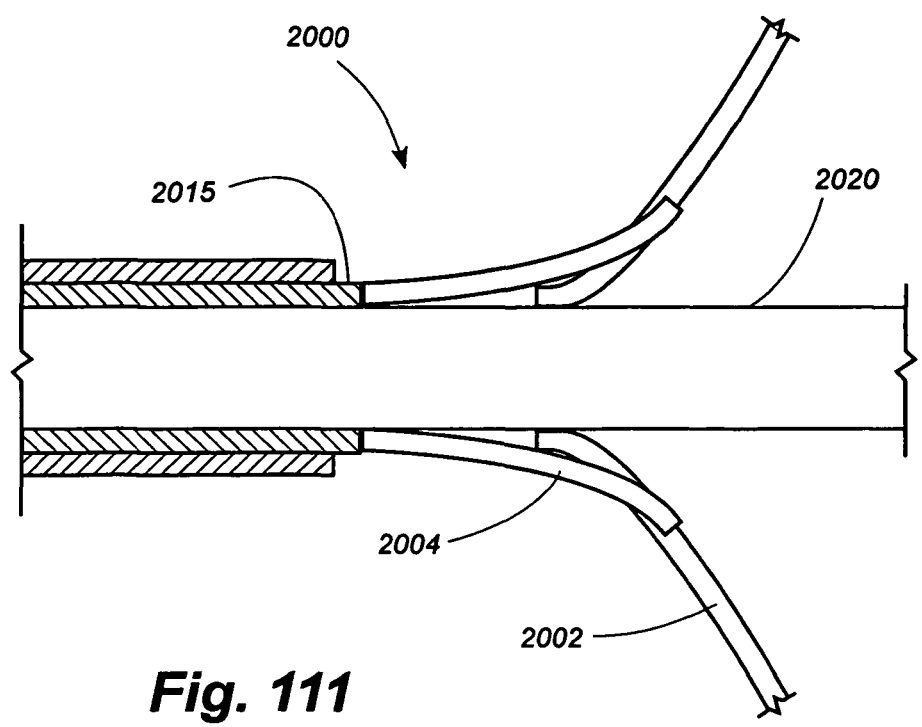
FIG. 111 is a schematic view of the heart of FIG. 109 showing a delivery device entering the heart through the right femoral vein, traversing the left atrium through the entry hound, and positioning the implant around the mitral annulus.

FIG. 111 shows an alternate embodiment of an implant/delivery system array 2000 in which the radial implant support arms 2002 and radial support struts 2004 are fixedly, rather than pivotably, mounted to their respective structures. More specifically, the proximal ends of the radial implant support arms 2002 are fixedly mounted to the core catheter 2020, and the radial support struts are fixedly mounted to the distal end of the actuating catheter 2015. Rather than the radial implant support arms 2002 and radial support struts 2004 pivoting with respect to the structures to which they are mounted. these elements are comprised of a flexible, resilient material which bends to effect opening and closing of the umbrella structure.

FIGS. 112-115 show an alternative means of achieving attachment of an implant or a surgical anastomosis or closure according to the present invention.

Figure 112:
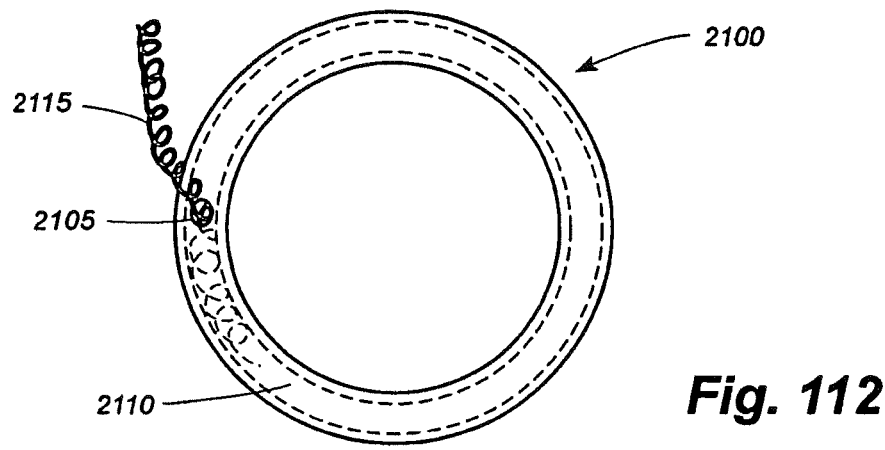
FIG. 112 is a top view of an implant for controlling the circumference of an internal orifice or lumen, wherein the implant comprises a spiral coil affixation device.
Figure 113:
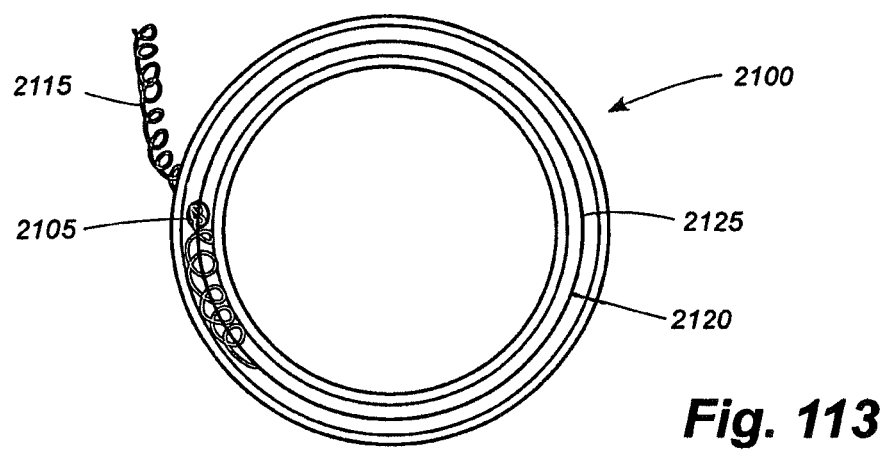
FIG. 113 is a bottom view of the implant of FIG. 112.
Figure 114:
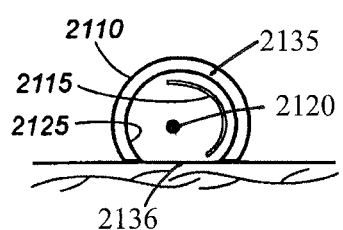
FIG. 114 is a transverse cross section of the implant of FIG. 112 prior to the spiral coil affixation device being inserted through the underlying tissue.
Figure 115:
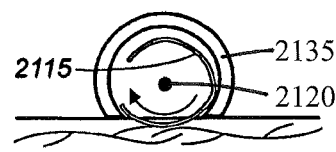
FIG. 115 is a transverse cross section of the implant of FIG. 112 subsequent to the spiral coil affixation device being inserted through the underlying tissue.

In FIGS. 112 and 113, an exemplary implant according to the present invention is shown as a generally circular implant body 2100, with an outer surface 2110, one or more closure portals 2105 capable of receiving a closure coil 2115, an inner surface 2125, and a closure track 2120. As shown in FIGS. 114 and 115, the implant of this example is semi tubular, with contoured implant body walls 2135 that incompletely form a tube leaving a closure gap 2135 on the inner surface 2125 of the implant 2100. The closure track 2120 functions to guide a coil 2115 such that, when said coil 2115 is introduced and rotated through a closure portal 2105, the coil follows the contours of the implant body walls 2135, and will follow a substantially spiral path that will continue through the closure gap 2136. Thus, when such an implant 2100 is pressed against a desired anatomic tissue 2140 as shown in FIGS. 114 and 115, sufficient advancement of a coil 2115 in the coursing of said coil 2115 into and through the underlying desired anatomic tissue 2140 until the coil 2115 has been advanced for the desired length.

Figure 116:
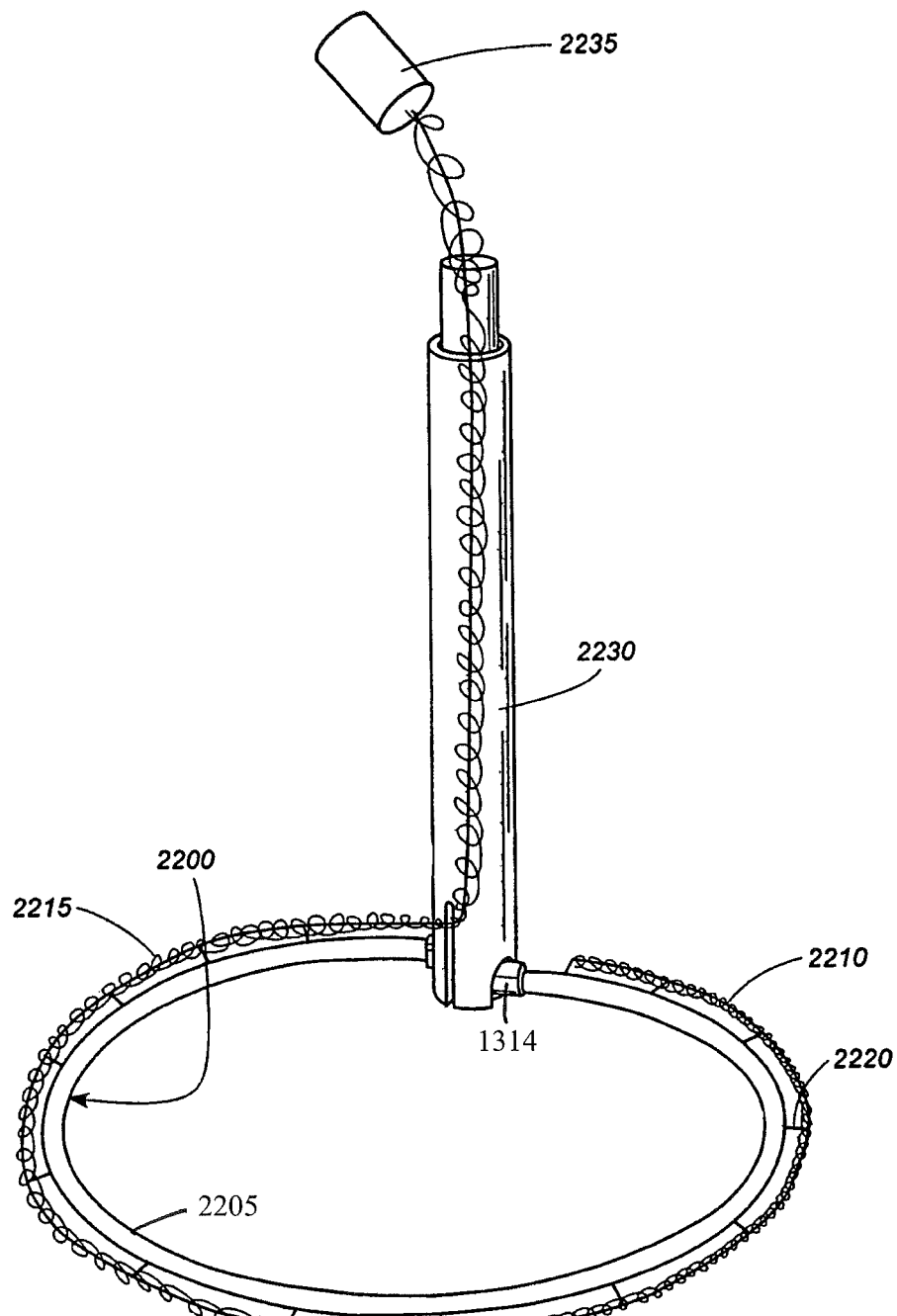
FIG. 116 is a schematic view illustrating the actuation of a spiral coil affixation device of an alternate embodiment.

FIG. 116 shows an alternate embodiment according to the present invention, in which a generally circular implant 2200 comprises an implant body 2205. A track 2210 is supported around the periphery of the implant body 2205 by track carriers 2220. A coil 2215 may be advanced on the track carriers 2220. In the example shown in FIG. 116, the coil 2215 is advanced through a delivery housing 2230 and may be supplied by a coil spool 2235. In yet other embodiments, an attachment coil may be attached to or introduced over a guide wire. In such an exemplary embodiment, the coil may be advanced by the manual action of an operator, or may be advanced using micromotors, mechanical geared systems, or other means of turning or advancing the coil 2215. In various such alternate embodiments, the delivery housing 2230 may incorporate or be incorporated within a handle or other ergodynamically favorable operational device or tool.

Figure 117:
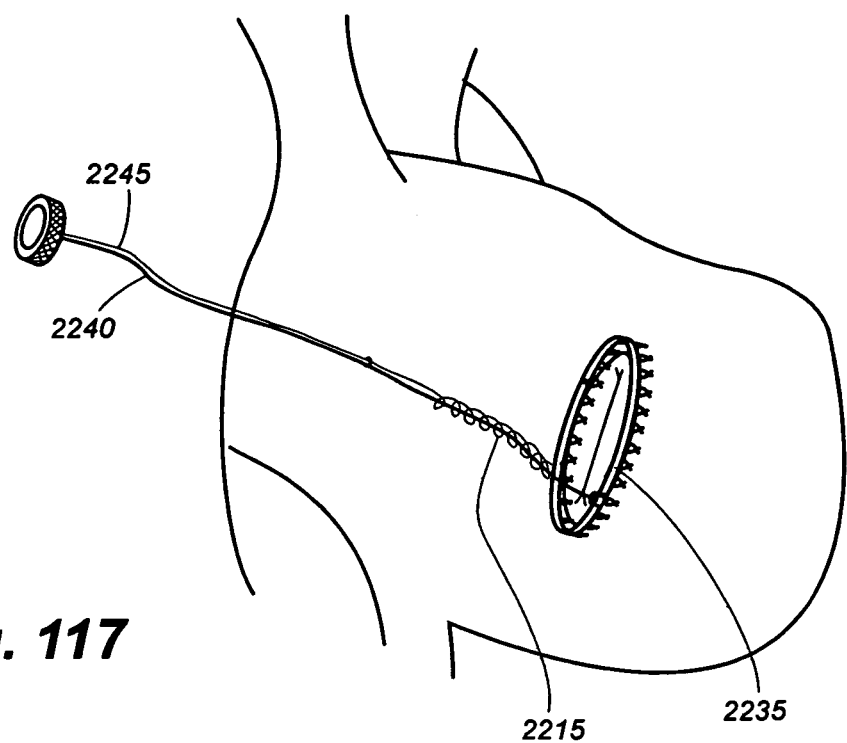
FIG. 117 is a schematic view of an alternate embodiment of an implantation device in which a coil attachment according to the present invention is used to attach an adjustable mitral annuloplasty implant in a minimally-invasive approach to a beating heart

Referring now to FIG. 117, an alternate embodiment is shown, in which a coil attachment 2215 according to the present invention is used to attach an adjustable mitral annuloplasty implant 2235 in a minimally-invasive approach to a beating heart, following an implantation procedure similar to that described previously in this disclosure. In the example shown in FIG. 117, the coil 2215 is advanced over a guide wire 2240, configured to allow detachment of the guide wire 2240 from the coil 2215 after the coil 2215 had been fully deployed, similar to the method of detaching an adjustment element 2245 according to the present invention after the desired post implantation adjustment is achieved.

In the example shown in FIGS. 113 117, circumferential or near circumferential deployment of a coil would be desirable to affix the implant to the underlying tissue. However, in various embodiments according to the present invention, such a coil attachment is used to attach implants, accomplish luminal anastomoses, or close surgical or other wounds. Exemplary applications amenable to the coil attachment according to the present invention include, but are not limited to, affixing cardiac valves or annuloplasty devices, vascular anastamosis, gastrointestinal or genitourinary anastamoses, arterotomy closure, endoscopic or laparoscopic internal soft tissue closure following hysterectomy, cholecystectomy, or other procedures, or the layered or non-layered closure of soft tissue wounds. Depending upon the desired application, such closure is accomplished in a generally circular manner as shown in the exemplary FIGS. 113-117, or in a straight or other geometric configuration in other embodiments according to the present invention.

The coil attachment devices and methods according to the present invention offer secure, sutureless closure and seal, with the functional effect of a finely sutured closure and the ability to accomplish this closure in a minimally invasive or endoscopic procedure where suturing may be difficult. Moreover, even in open surgical procedures, coil closure according to the present invention offers a more rapid, reliable way to achieve implantation or closure than with conventional suture techniques. Moreover, the coil may be reversed and replaced, if there is any concern as to the adequacy or closure or accuracy of placement. Such coils according to the present invention may be fabricated of biologically inert stainless steel, titanium, other metals, metal alloys, plastics, other polymers, or other materials. In various embodiments, such coils may be fabricated of permanent or absorbable materials. In various embodiments, such coils may be advanced by hand or by machine, employing external or internal motors and/or gear arrays. The leading edge of a coil according to the present invention may be sharpened or blunted, depending upon the application and effect desired.

Finally, it will be understood that the preferred embodiment has been disclosed by way of example, and that other modifications may occur to those skilled in the art without departing from the scope and spirit of the appended claims.

Expected variations or differences in the results are contemplated in accordance with the objects and practices of the present invention. It is intended, therefore, that the invention be defined by the scope of the claims which follow and that such claims be interpreted as broadly as is reasonable.

The invention claimed is:

1. An implantable device for controlling at least one of a shape and size of an anatomical structure or lumen, comprising:
    an adjustable implantable device having an adjustable member configured to adjust the dimensions of the implantable device, the implantable device including an implant body;
    an adjustment tool configured to be removeably coupled to the adjustable member to actuate the adjustable member and provide for adjustment before, during or after the anatomical structure or lumen resumes normal physiologic function;
    an elongated track member arranged extending through an interior of the implant body or arranged encircling an exterior of the implant body; and
    a coil configured to fasten the implantable device to tissue around the anatomic structure or lumen, wherein the coil is provided in a spiral path arranged encircling the track member and having a portion adapted to extend into the tissue adjacent the implantable device around the anatomic structure or lumen.

2. The device of claim 1, wherein the implantable device includes at least a first closure portal to receive the coil.

3. The device of claim 1, wherein the implantable device includes at least a first closure portal to receive the coil and the track member.

4. The device of claim 1, wherein the implant body is semi-tubular formed by an incomplete tubular body providing a closure gap, the track member arranged extending within the tubular body, whereby a portion of the coil extends through the closure gap.

5. The device of claim 4, wherein the incomplete tubular body includes an inner wall defining the interior, and wherein the coil at least partially follows contours of the inner wall of the implantable device.

6. The device of claim 4, wherein in response to the implantable device being pressed against the anatomical structure or lumen sufficient advancement of the coil results in a coursing of the coil into the anatomical structure or lumen tissue through the closure gap until the coil is advanced for a desired length.

7. The device of claim 1, wherein the track member is supported around a periphery of the implantable device.

8. The device of claim 7, wherein the track member is supported by track carriers.

9. The device of claim 1, wherein the coil is advanceable by manual action of an operator.

10. The device of claim 1, wherein the coil is advanceable non-manually.

11. The device of claim 1, wherein the coil is configured to fasten the implantable device to a beating heart using a minimally-invasive approach.

12. The device of claim 1, wherein the implantable device has a circular shape.

13. An implantable device adapted for use as an annuloplasty ring, comprising:
    an adjustable implantable ring;
    an adjustment tool adapted to adjust the implantable ring;
    an elongated track member extending through an interior of the ring or arranged encircling an exterior of the implantable ring; and
    a coil configured to fasten the implantable ring to anatomical tissue, the coil arranged encircling the track member along a spiral path, wherein the coil is adapted to penetrate the anatomical tissue when spiraling the coil over the track member around the implantable ring adjacent the anatomical tissue or lumen.

14. The device of claim 13, wherein the coil follows the spiral path around the track member within the interior of the ring.

15. The device of claim 13, wherein the coil follows the spiral path around the track member external to the ring.

16. The device of claim 13, wherein the implantable ring is semi-tubular formed by an incomplete tubular body providing a closure gap, the track member arranged within the tubular body, whereby a portion of the coil extends through the closure gap.

17. The device of claim 13, wherein the ring has a gap through which a portion of the coil extends.

* * * * *